(12) United States Patent
Perazzo et al.

(10) Patent No.: US 10,336,477 B2
(45) Date of Patent: Jul. 2, 2019

(54) SYRINGE PACKAGING SYSTEM FOR HOSPITAL PHARMACIES

(71) Applicants: Nicholas J. Perazzo, Rosedale, MD (US); Robert A. Rosen, Owings Mills, MD (US); John G. Grosskopf, Jr., Ellicott City, MD (US); Mark Bennett, Ellicott City, MD (US); John M. Chopper, Pasadena, MD (US)

(72) Inventors: Nicholas J. Perazzo, Rosedale, MD (US); Robert A. Rosen, Owings Mills, MD (US); John G. Grosskopf, Jr., Ellicott City, MD (US); Mark Bennett, Ellicott City, MD (US); John M. Chopper, Pasadena, MD (US)

( * ) Notice: Subject to any disclaimer, the term of this patent is extended or adjusted under 35 U.S.C. 154(b) by 368 days.

(21) Appl. No.: 15/114,566

(22) PCT Filed: Jan. 28, 2015

(86) PCT No.: PCT/US2015/013217
§ 371 (c)(1),
(2) Date: Jul. 27, 2016

(87) PCT Pub. No.: WO2015/116637
PCT Pub. Date: Aug. 6, 2015

(65) Prior Publication Data
US 2016/0340066 A1 Nov. 24, 2016

Related U.S. Application Data

(60) Provisional application No. 61/932,318, filed on Jan. 28, 2014.

(51) Int. Cl.
*B65B 3/00* (2006.01)
*A61M 5/178* (2006.01)
(Continued)

(52) U.S. Cl.
CPC .......... *B65B 3/003* (2013.01); *A61M 5/1782* (2013.01); *B65B 3/12* (2013.01); *B65B 43/54* (2013.01)

(58) Field of Classification Search
CPC ......... B65B 3/003; B65B 3/12; A61M 5/1782
(Continued)

(56) References Cited

U.S. PATENT DOCUMENTS 5,431,201 A * 7/1995 Torchia ..................... A61J 1/20
141/100
5,479,969 A * 1/1996 Hardie ..................... B65B 3/003
141/103
(Continued)

*Primary Examiner* — Timothy L Maust
(74) *Attorney, Agent, or Firm* — Royal W. Craig; Gordon Feinblatt LLC

(57) ABSTRACT

A semi-automated system (100) suitable for use in a hospital setting for filling patient-specific liquid medication prescriptions from bulk medicine containers (104) into oral syringes (S) for administration on a just-in-time basis. The system enables hospital pharmacists to simplify and streamline their task, increasing the number of prescriptions mat can be filled in a day, improving patient safety and care by minimizing medication errors and the consequences that ensue. The present invention also includes a novel adapter cap for use in interfacing between bulk medicine containers (104) and syringes (S) having a Luer-lock fitting.

31 Claims, 54 Drawing Sheets

(51) Int. Cl.
*B65B 3/12* (2006.01)
*B65B 43/54* (2006.01)

(58) Field of Classification Search
USPC .................................................. 141/319, 329
See application file for complete search history.

(56) References Cited

U.S. PATENT DOCUMENTS

| | | | | |
|---|---|---|---|---|
| 7,258,052 | B1 * | 8/2007 | McLean | B26D 7/088 83/168 |
| 7,610,115 | B2 * | 10/2009 | Rob | A61J 1/20 700/245 |
| 7,681,606 | B2 * | 3/2010 | Khan | B65B 3/003 141/144 |
| 7,783,383 | B2 * | 8/2010 | Eliuk | A61J 1/20 141/1 |
| 8,271,138 | B2 * | 9/2012 | Eliuk | B66C 1/42 294/902 |
| 9,033,006 | B2 * | 5/2015 | Perazzo | A61J 7/0053 141/319 |
| 9,382,021 | B2 * | 7/2016 | Tribble | B65B 3/003 |
| 2004/0154690 | A1 * | 8/2004 | Osborne | B01F 13/1072 141/27 |
| 2012/0325365 | A1 * | 12/2012 | Strangis | B63C 9/0005 141/2 |
| 2014/0157731 | A1 * | 6/2014 | Perazzo | B65B 57/02 53/473 |

* cited by examiner

FIG 5
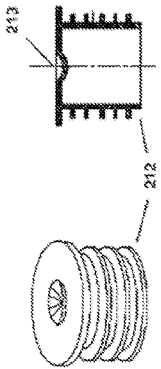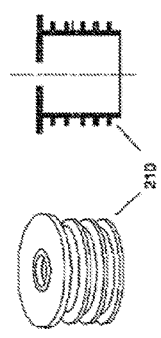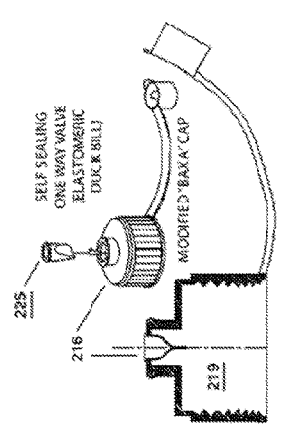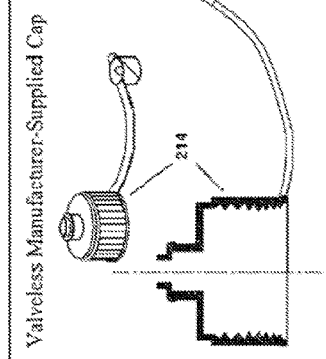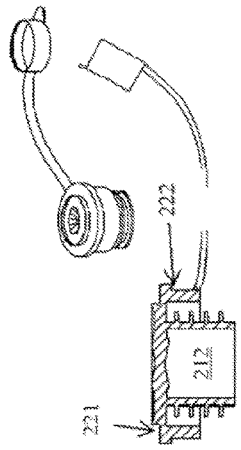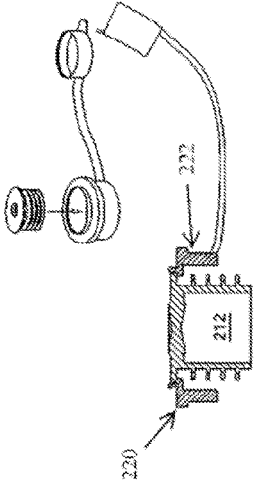

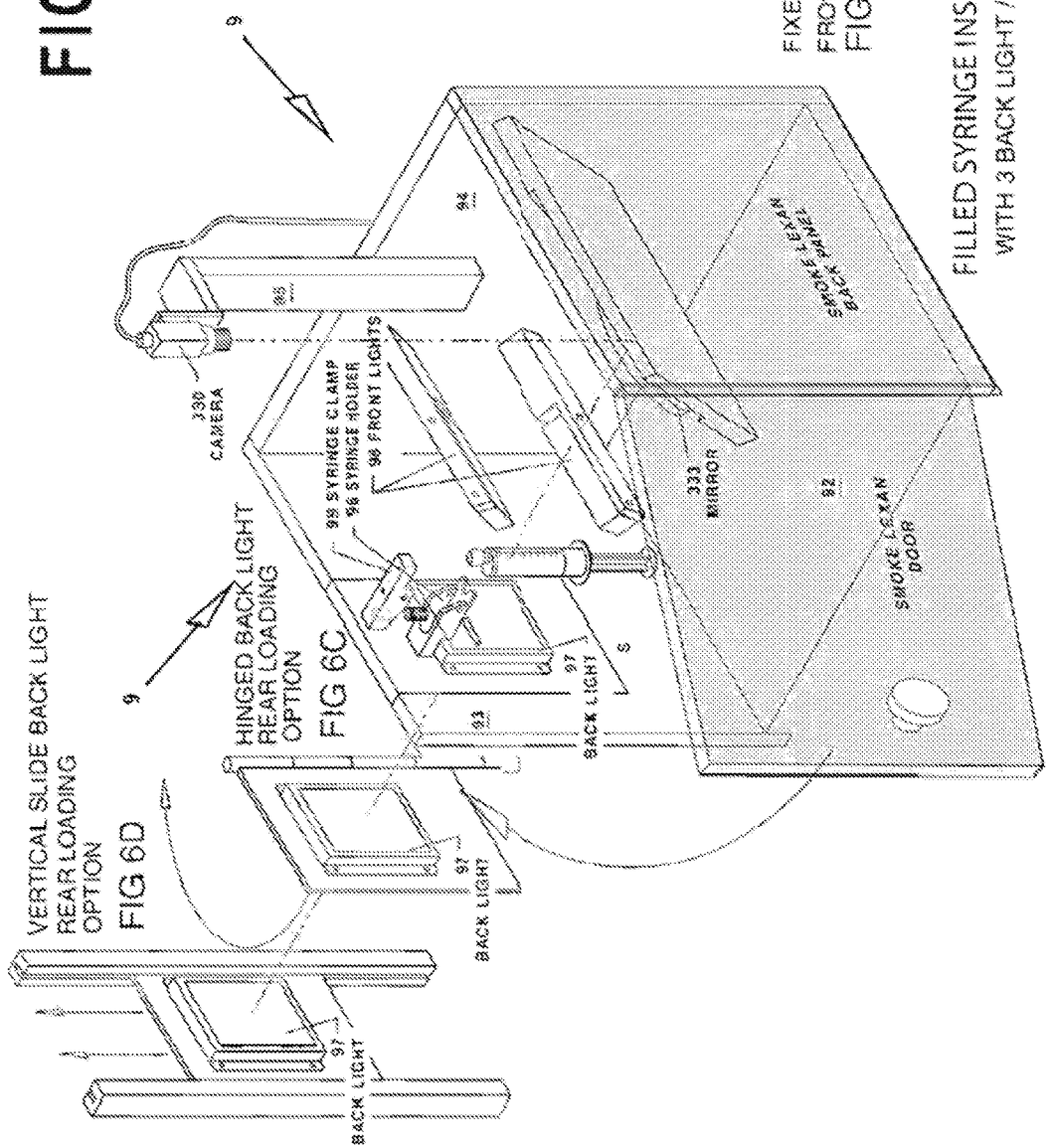

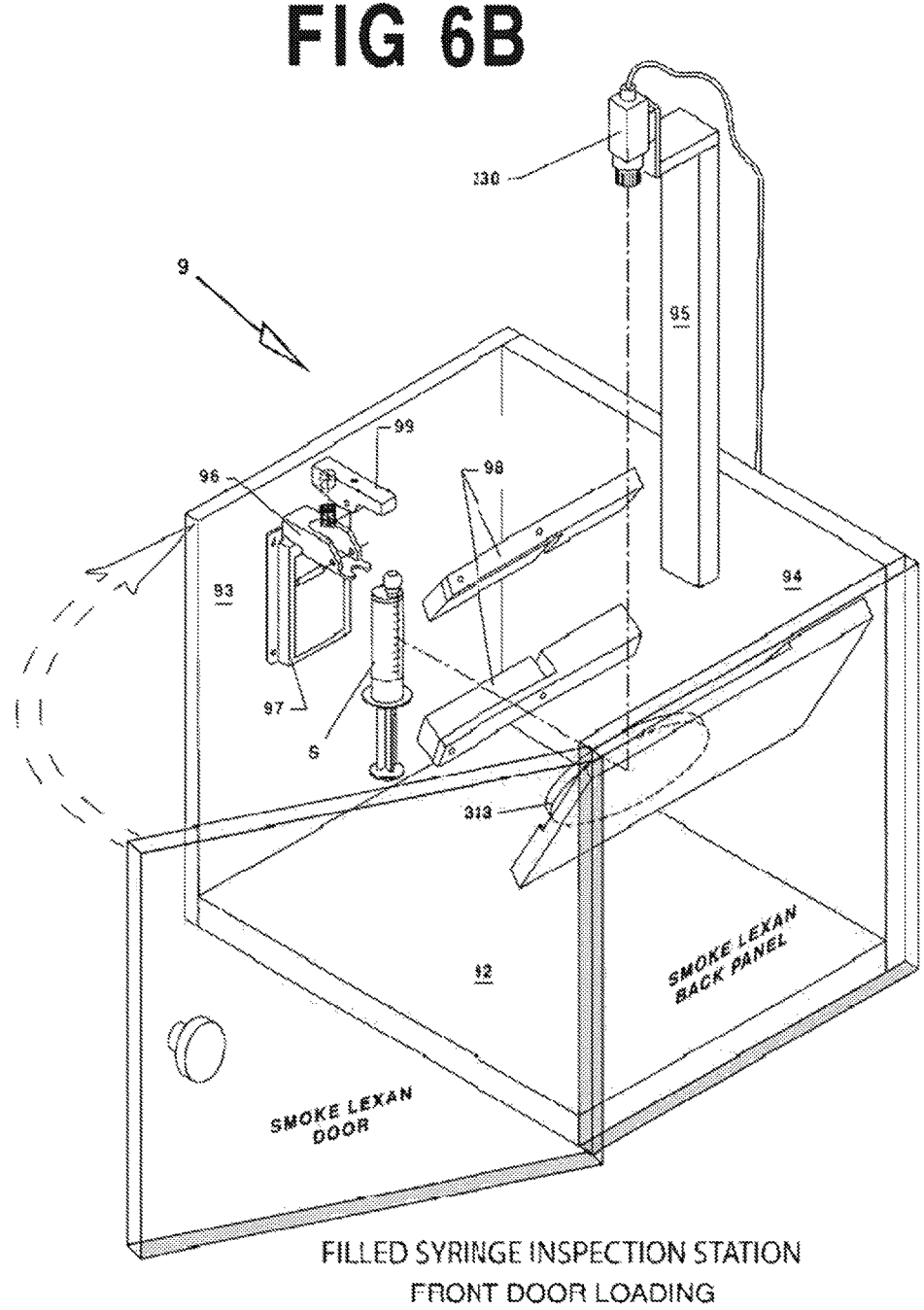

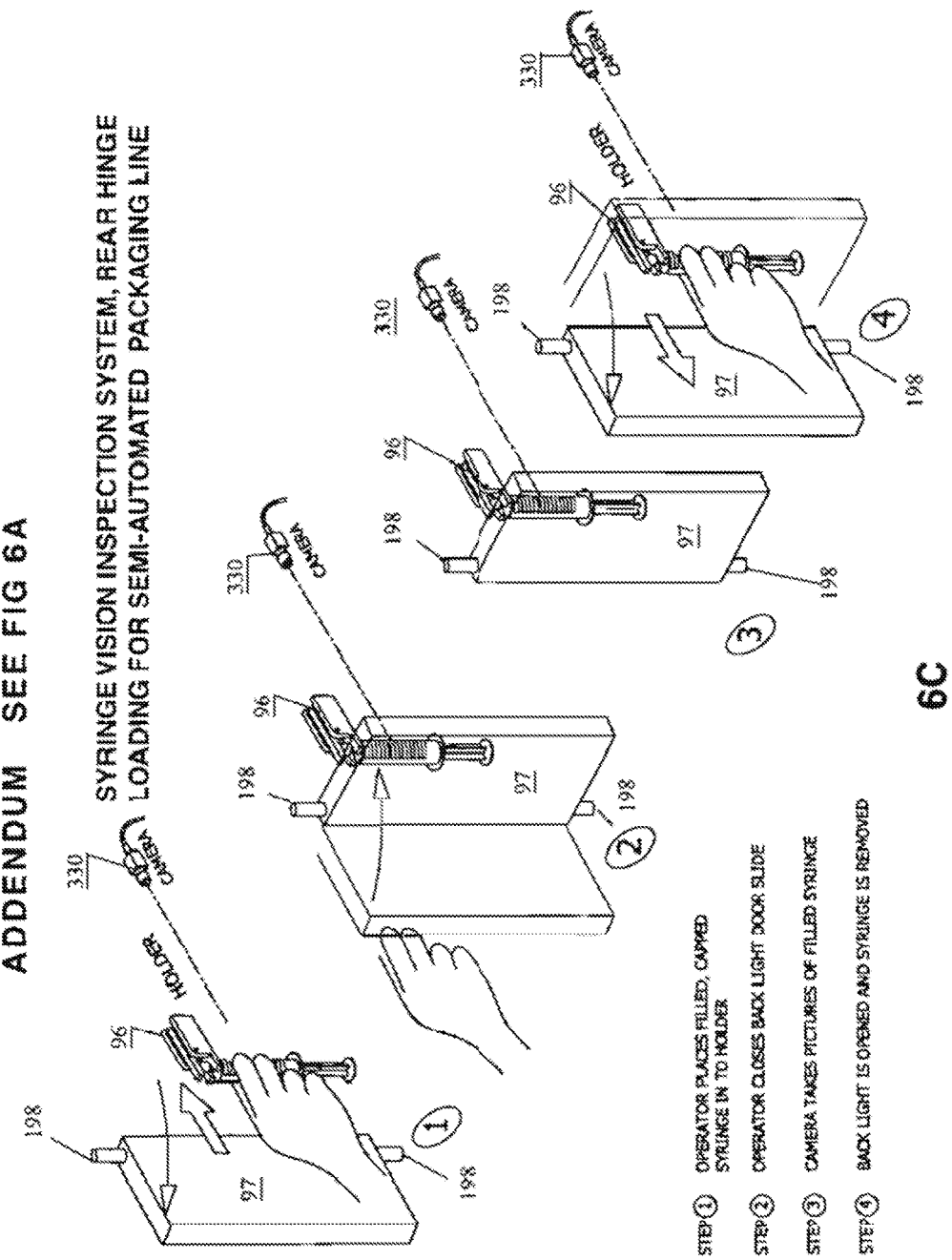

ADDENDUM SEE FIGURE 6
SYRINGE VISION INSPECTION SYSTEM, REAR VERTICAL LOADING FOR SEMI-AUTOMATED PACKAGING LINE

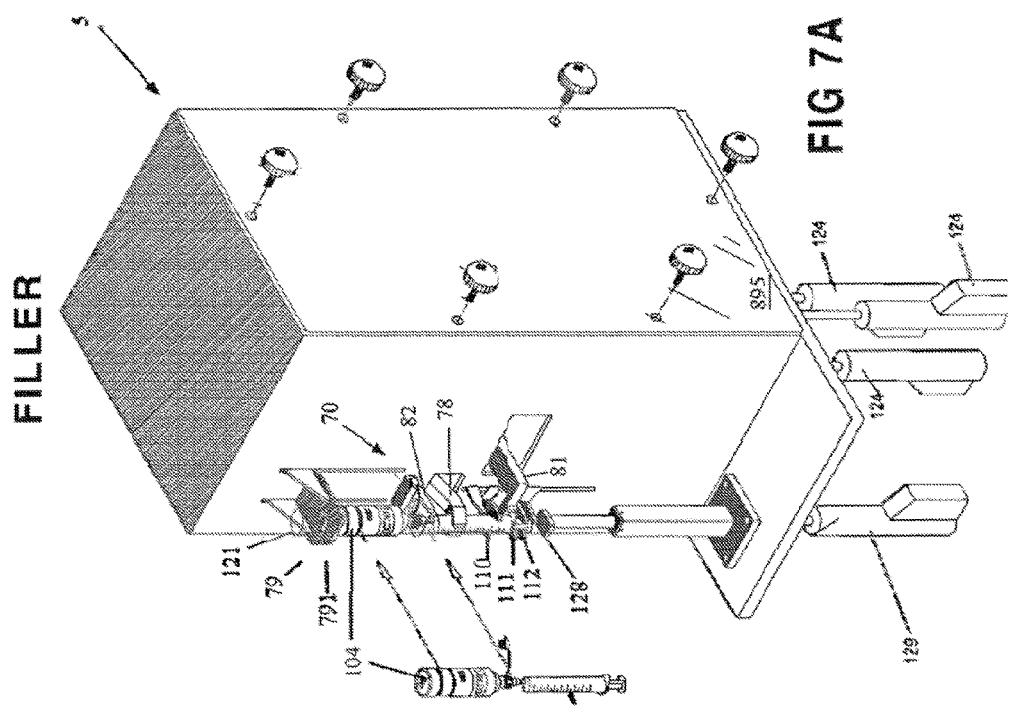

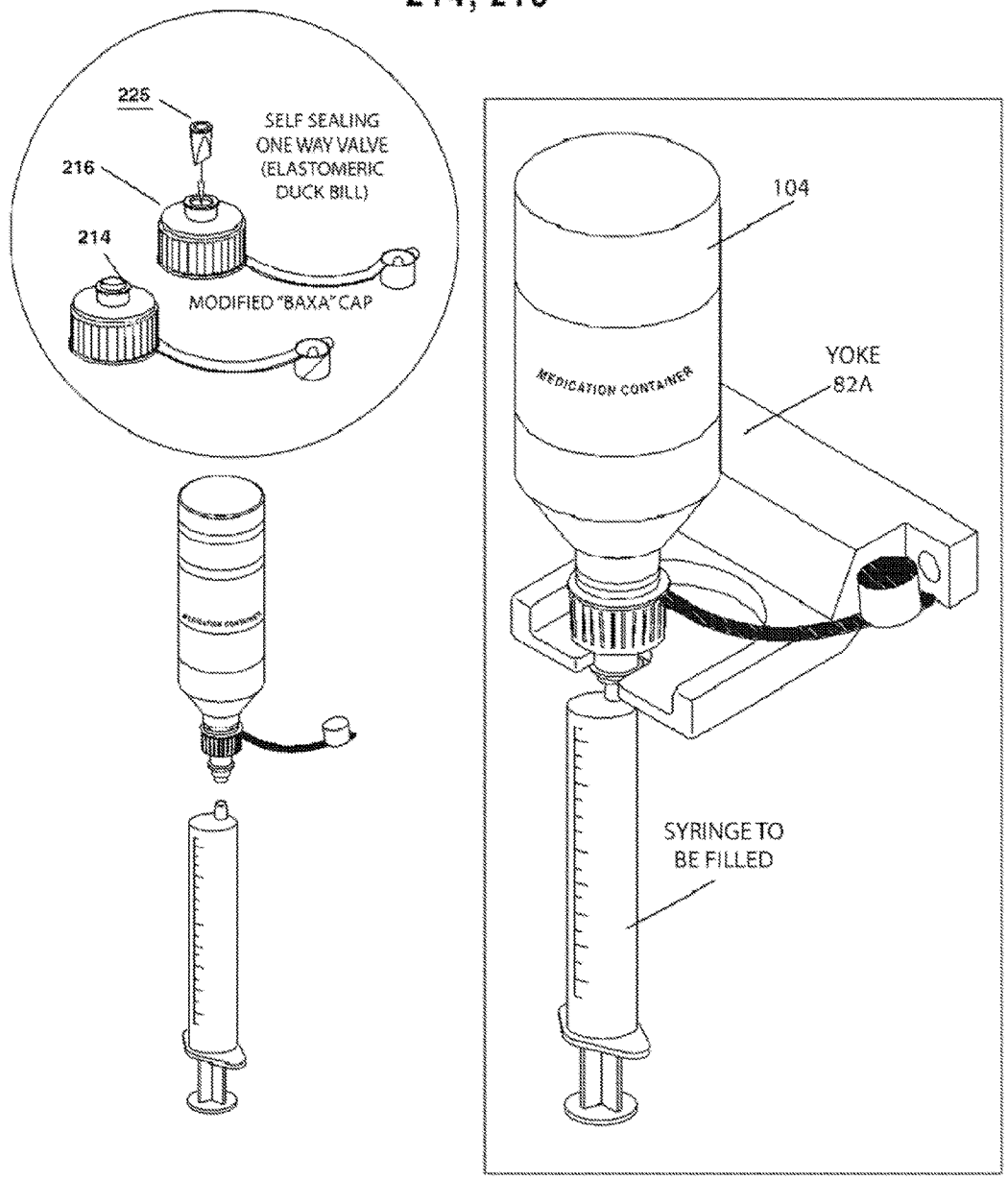
FIG 7CI  FOR. SYRINGE / MEDICATION / INTERFACES 214, 216

FIG 7C II  FOR. SYRINGE / MEDICATION / INTERFACE 210
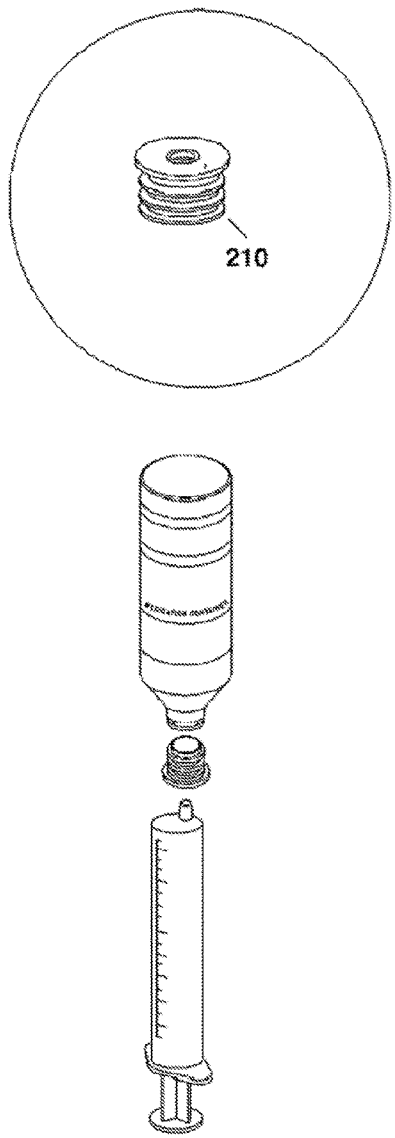
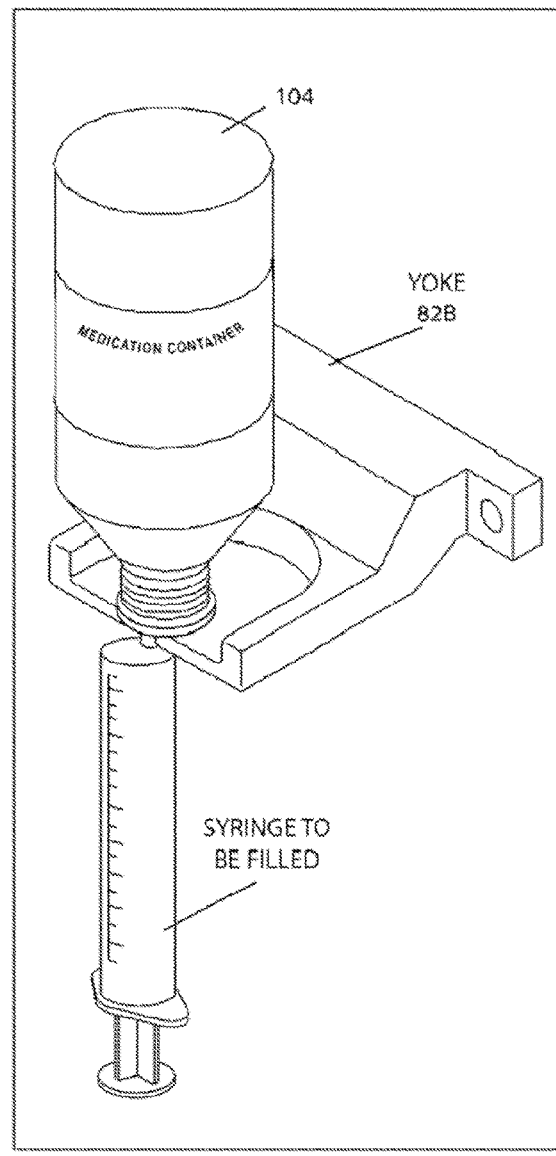

FIG 7C III  FOR. SYRINGE / MEDICATION / INTERFACE 212
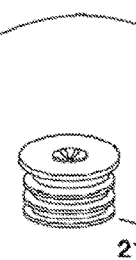
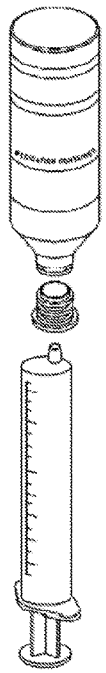
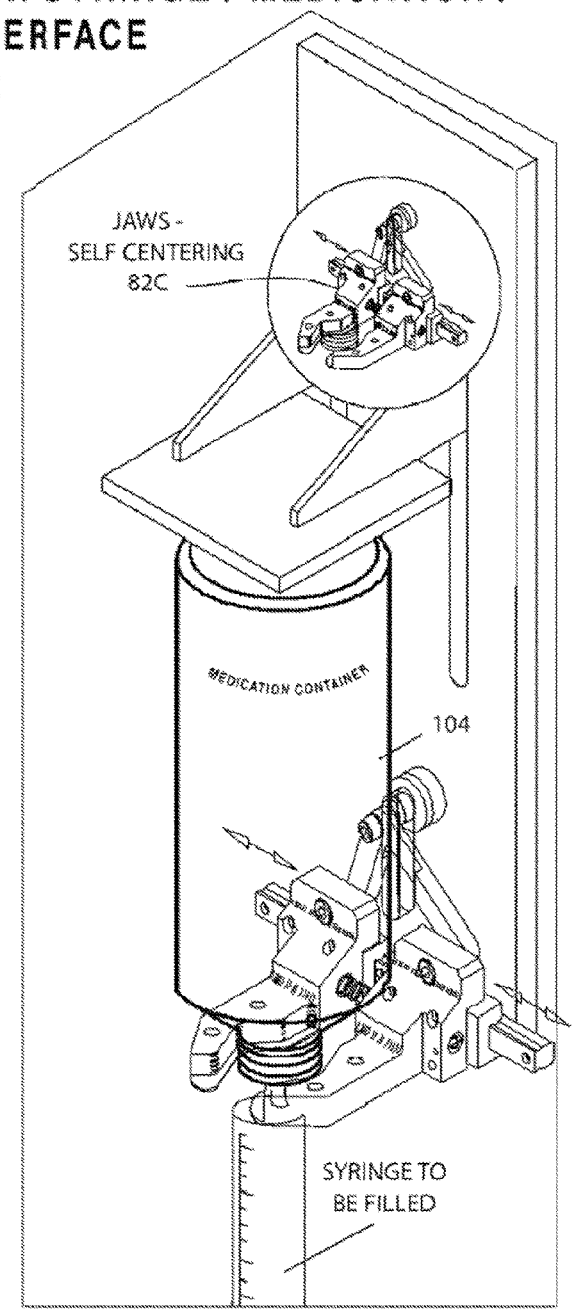

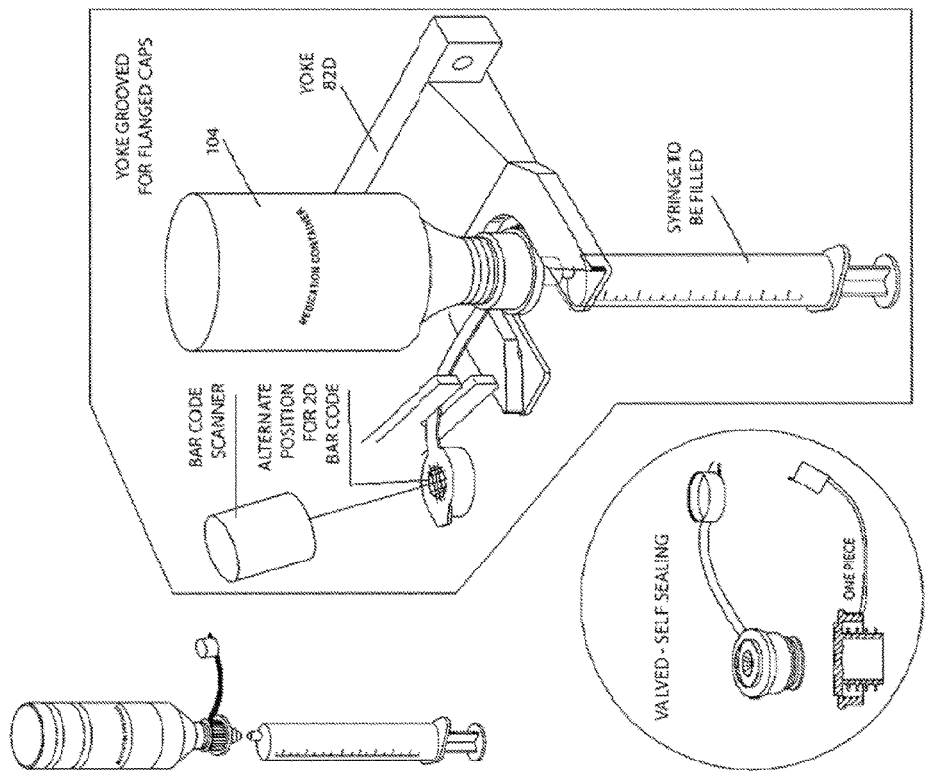

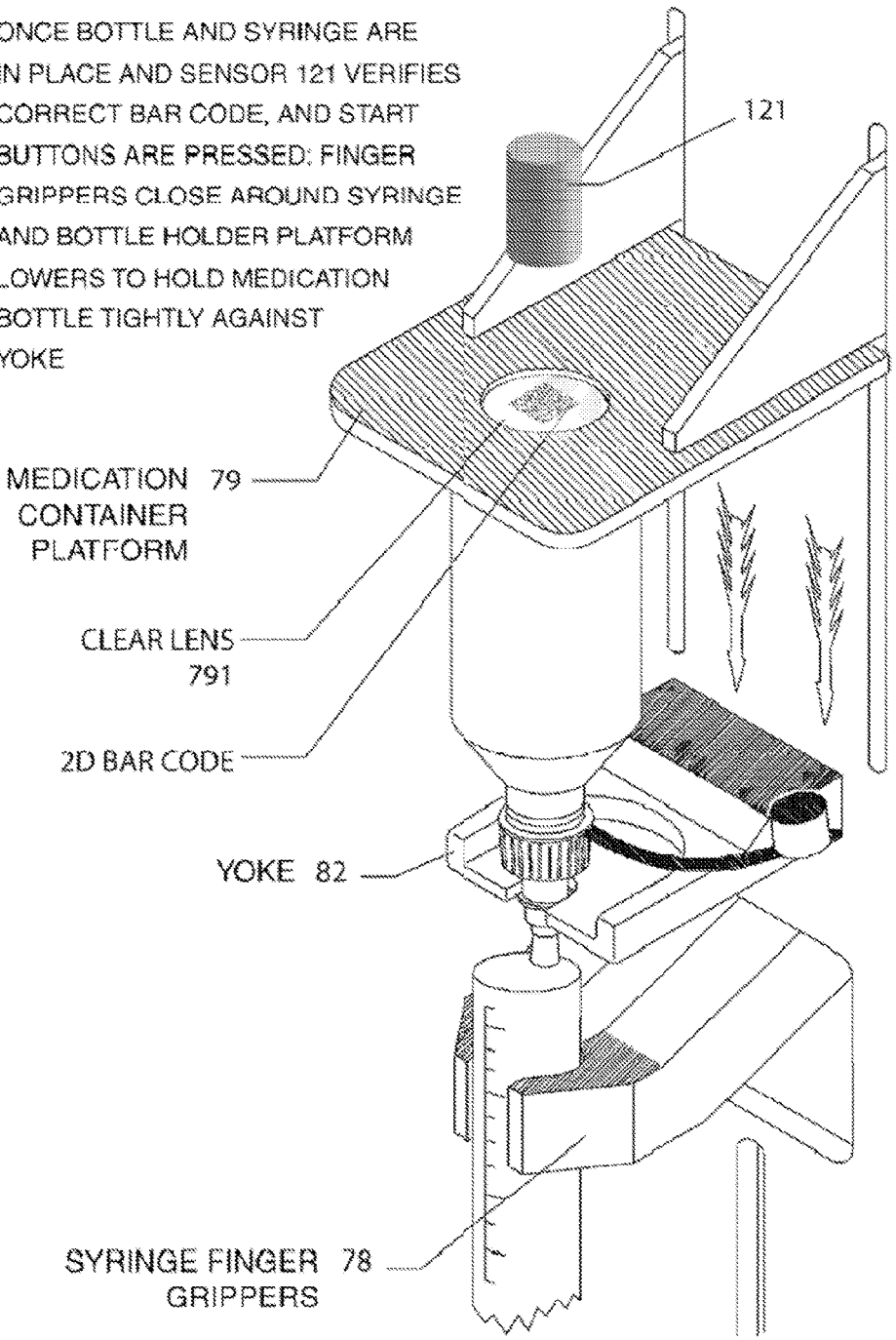

ALTERNATE SIZE / COLOR INSPECTION

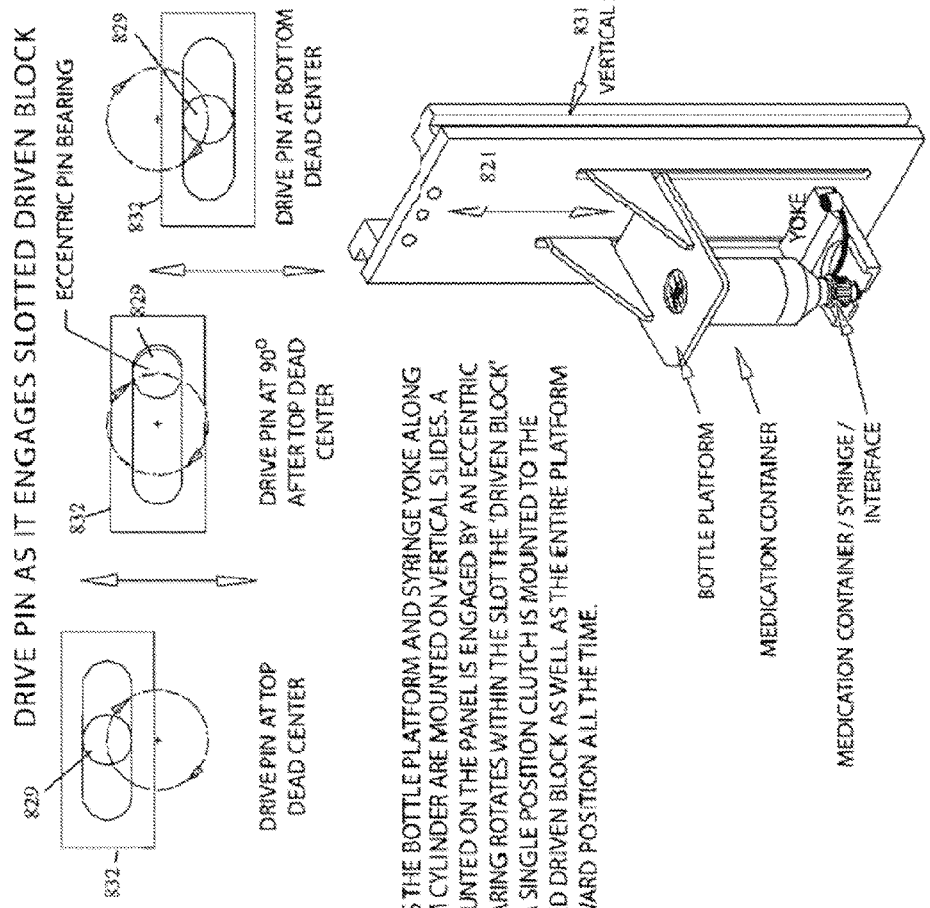

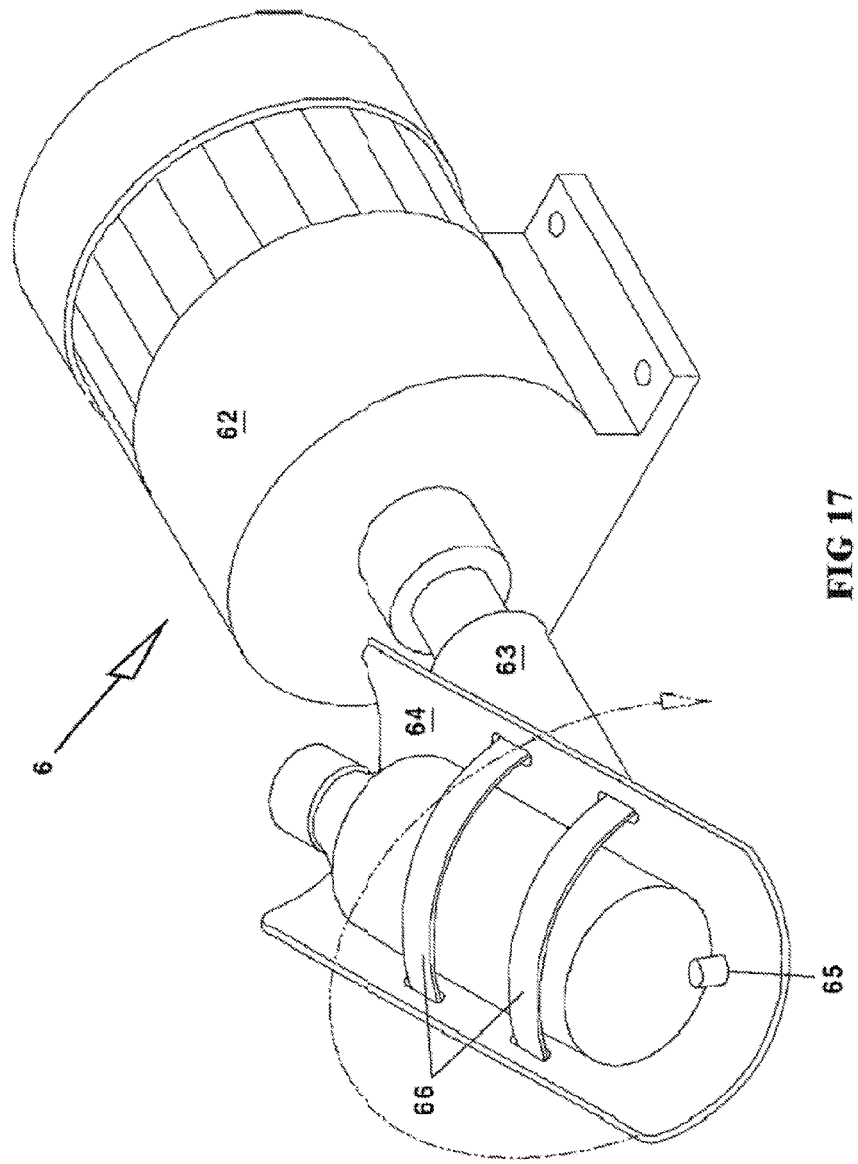

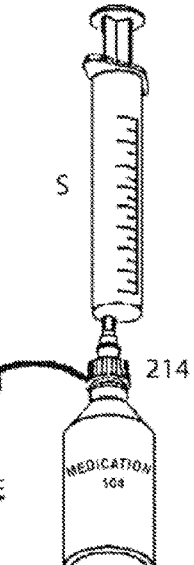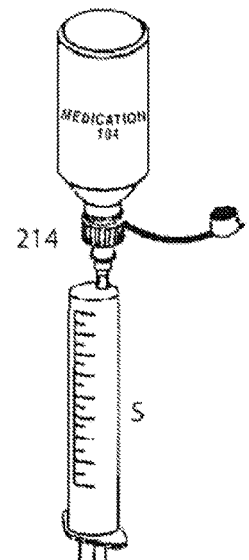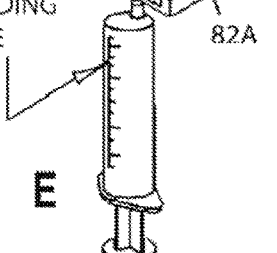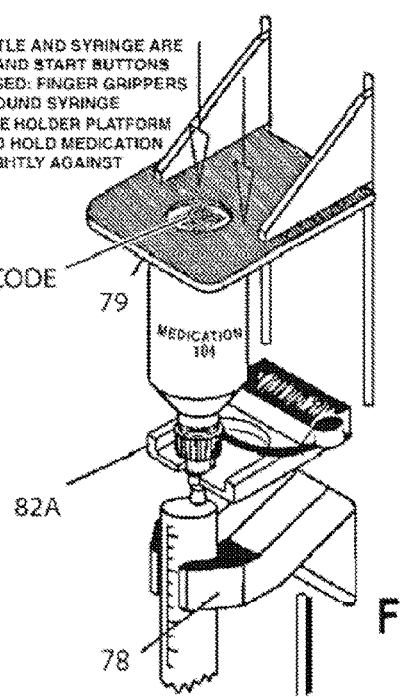
FIG 18

PIBA (SELF-SEALING)
REMOVE MEDICINE BOTTLE CAP
A
B
C
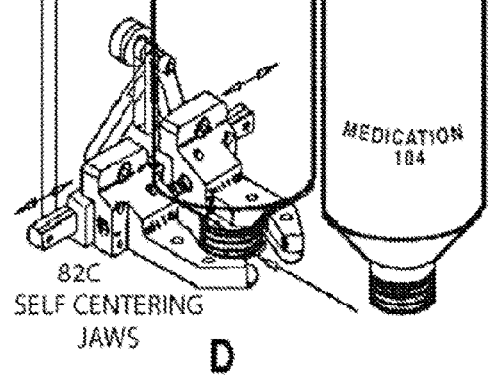
BOTTLE PLACED IN SELF CENTERING JAWS
MEDICATION CONTAINER PLATFORM
79
82C SELF CENTERING JAWS
D
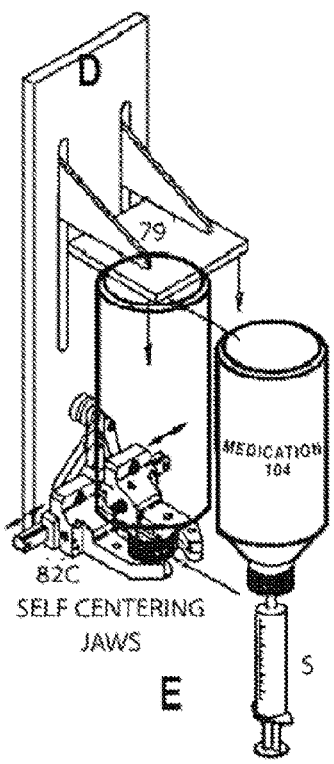
D
79
82C SELF CENTERING JAWS
E
FIG 21

SYRINGE HANDLING USING
2 OPERATORS AND 3 GROUPED STATIONS
(Option 2)

SYRINGE HANDLING USING
THREE OPERATOR AND 3 GROUPED STATIONS
(Option 4)

Note: 3 to 5 Syringe Compartments Per Tray

PUSH-PULL VALVE VERSION 4

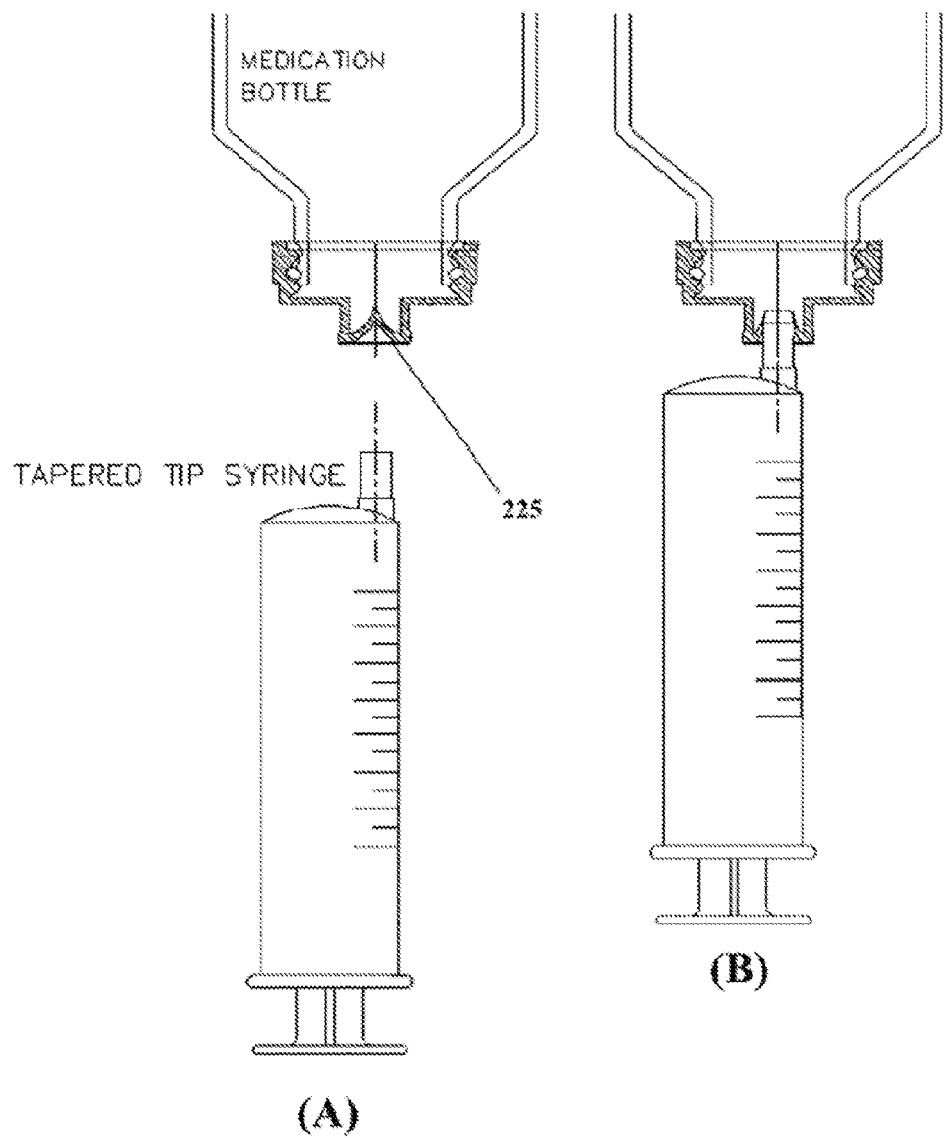

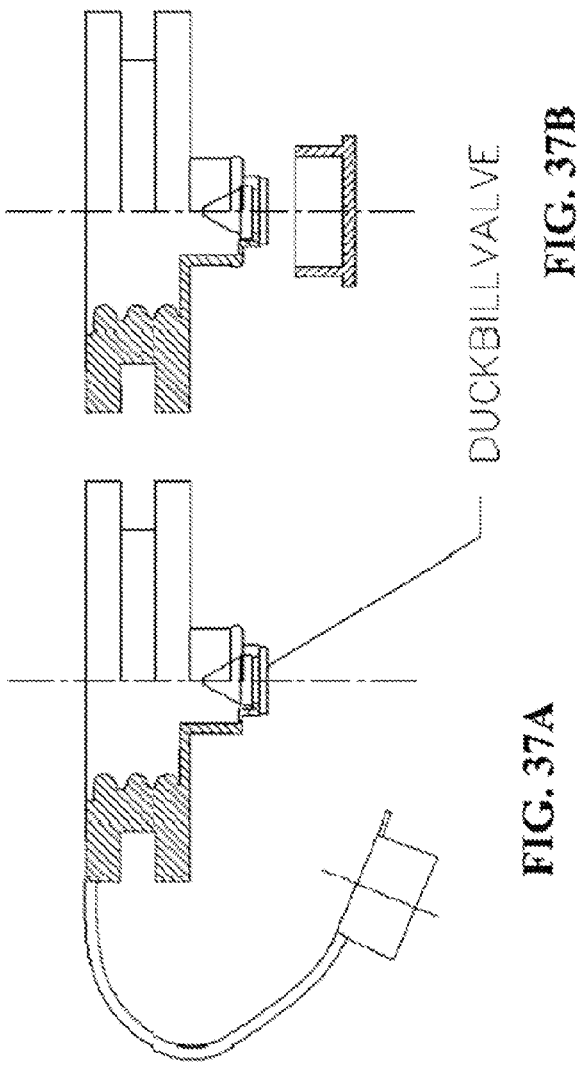

TAPERED TIP SYRINGE

LUER LOCK SYRINGE

LUER LOCK SYRINGE

FILLER WITH PUSH-PULL VALVE CAP IN PLACE

PUSH-PULL VALVE CAP

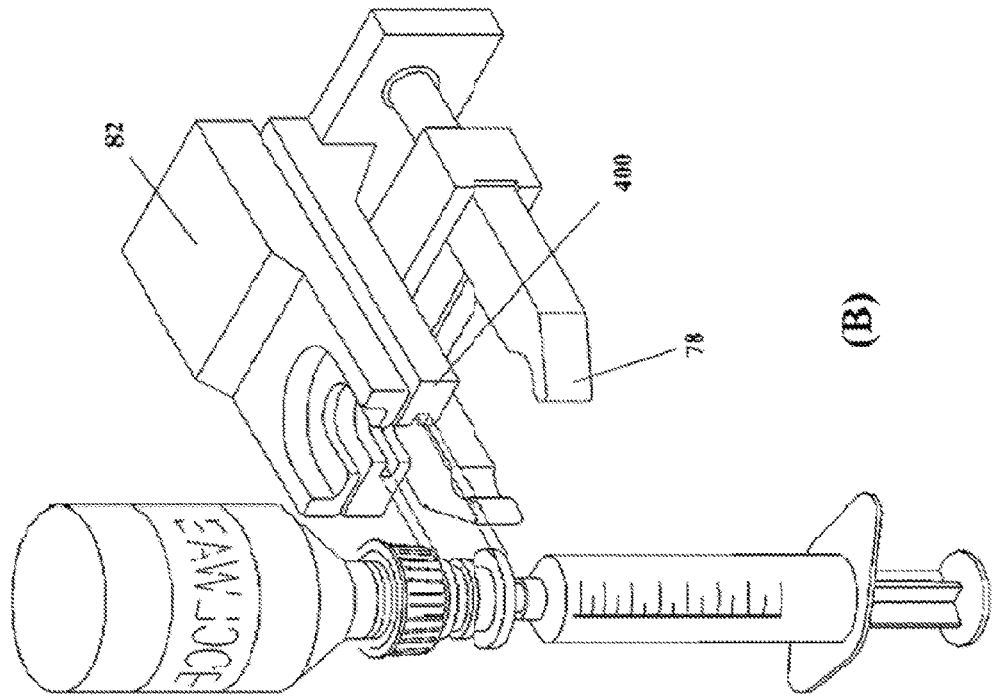
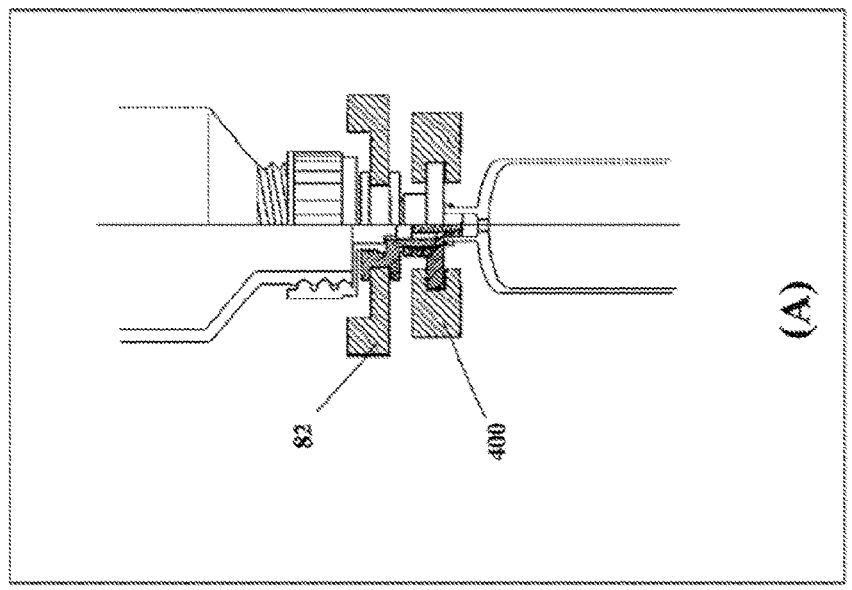
FIG. 43

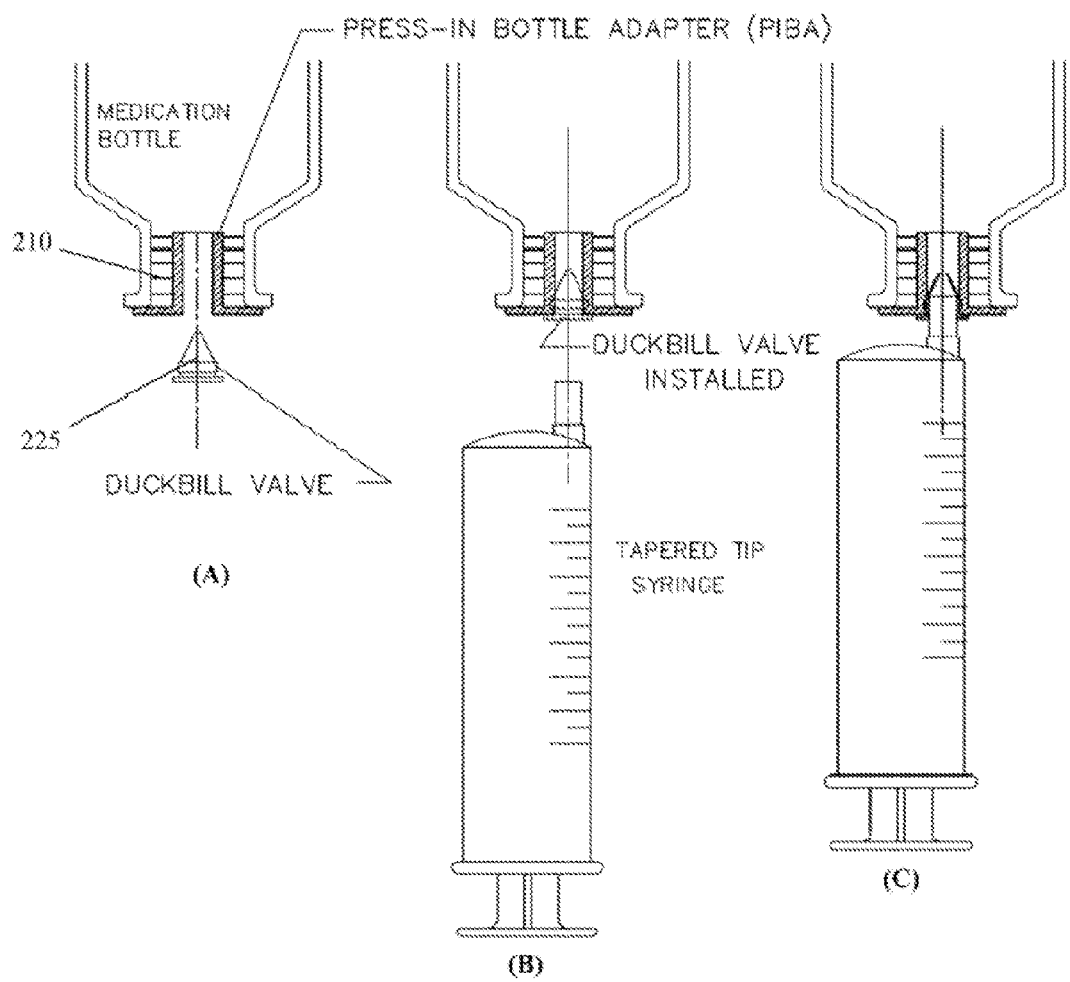

SYRINGE PACKAGING SYSTEM FOR HOSPITAL PHARMACIES

CROSS-REFERENCE TO RELATED APPLICATIONS

The present application derives priority from U.S. provisional patent application Ser. No. 61/932,318, filed Jan. 28, 2014, which is a continuation-in-part of U.S. patent application Ser. No. 13/236,577, filed Sep. 19, 2011 (which derives priority from U.S. provisional patent application Ser. No. 61/384,217 filed Sep. 17, 2010, and U.S. provisional patent application Ser. No. 61/494,677 filed Jun. 8, 2011), all of which are incorporated herein by reference.

BACKGROUND OF THE INVENTION

1. Field of the Invention

The present invention relates generally to oral syringe packaging equipment and more specifically to a partially automated system for preparing patient-specific doses of selected pharmaceutical liquid medication for administration by oral syringe on a just-in-time basis, for use in a hospital pharmacy.

2. Description of the Background

Oral syringes are well known instruments in the medical fields and are used to administer liquid medicine into the mouth, as an alternative to pills which can present a choking hazard or be expectorated, typically for infants/children and uncooperative or geriatric adults. The oral syringe directs liquid medicine to the back of the throat prompting a swallowing response. Injectable syringes, on the other hand, are used to administer medication into the body by injecting its contents through the skin. Injectable syringes utilize a needle on the tip of the syringe. Injectable syringes must be manufactured and packaged in a sterile environment. Research has shown that the potential for adverse drug events within the pediatric inpatient population is about three times as high as among hospitalized adults. See, Joint Commission, Preventing Pediatric Medication Errors, Issue 39 (2008). According to the Commission Report, the most common types of harmful pediatric medication errors were improper dose/quantity (37.5 percent) and unauthorized/wrong drug (13.7 percent), followed by improper preparation or dosage form. Oral syringes help to minimize these problems and are considered the gold standard for delivering medicine to children.

Oral syringes, which are relatively inexpensive and disposable, are comprised of a simple piston pump with a plunger that fits tightly in one end of a cylindrical tube (the barrel) and can be pushed or pulled along inside the barrel to create negative or positive relative pressure within the barrel that causes the syringe to take in or expel a liquid or gas through an orifice (nozzle) at the opposing end of the barrel. An annular flange partially or fully encircling the outside surface of the barrel is typically provided to facilitate compression of the plunger into the barrel. The barrel of an oral syringe is typically made of plastic and is at least partially transparent along its length with graduated markings to indicate the volume of fluid in the syringe based on the position of the plunger, which is thus visible within the barrel. Oral syringes are commonly marked in units of milliliters and come in standard sizes ranging from 0.5 to 60 milliliters. The plunger is also typically plastic as this provides a good seal within the barrel and is inexpensive to produce so as to be disposable, reducing the risk of contamination or transmission of communicable disease. Oral syringes come in a wide range of sizes and with some variation in configuration. For example, some oral syringes have the nozzle located along the central axis while others have the nozzle offset from the central axis. This variability makes it difficult to automate the filling process for oral syringes.

Pharmacies at in-patient medical facilities and other medical institutions fill a large number of prescriptions on a daily basis including prescriptions for liquid or compounded suspension medicines to be administered by oral syringe, and must do so accurately for medical safety reasons. The volume of an oral pediatric prescription's dose is determined by the child's weight. This makes it impractical to stock pre-filled syringes due to the wide range of fill volumes required. As a result, pediatric oral liquid doses are prepared in the hospital pharmacy on a patient-specific, just-in-time basis. The process of filling numerous, variously sized single dose prescriptions for delivery by oral syringe is time consuming, labor intensive and prone to human error. To ensure that the medication is packaged error-free, the pharmacy technician must make sure that: (1) the syringe contains the correct medication; (2) the syringe contains the correct amount of medication; (3) the syringe is capped correctly; (4) the medication has not expired; (5) the medication has not been recalled; (6) the medication, when required, is shaken; (7) the medication, when required, has been properly refrigerated; (8) the medication, when required, has been properly protected from exposure to light; (9) the information on the syringe label is correct; (10) the syringe is placed into the correct bag; (11) the information on the bag containing the syringe is correct; (12) the bag is properly sealed; and (13) the syringe is protected from cross contamination from other medications. The process typically requires a pharmacist or pharmacy technician to retrieve the correct medication from a storage cabinet (with or without light protection) or refrigerated storage area. The liquid medications are typically stored in a container sealed with a safety cap or seal. After confirming the contents of the retrieved container and shaking the medication (if necessary), the technician manually opens the cap and inserts the tip of an oral syringe into the container which has previously been adapted to accept the syringe, inverts the container, and then withdraws the plunger to draw the medication into the barrel of the syringe. After filling with a proper amount, the syringe and medication container are rotated back to the original position, the syringe is removed from the container, the tip of the syringe is covered with a cap for transport to the patient and the syringe is labeled to indicate its content and the intended recipient, and then bagged. Prior to administering the dose, the nurse can determine the amount of the dose by observing where the tip of the plunger or piston is located in the barrel.

Currently, the degree of automation in the hospital pharmacy for the packaging of oral syringes is very limited. Islands of automation exist, such as automatic labeling of the syringe and bagging of the filled and capped syringe to indicate to the administering nurse the content of the syringe. However, the filling and capping of oral syringes are done manually. Scanners, cameras, bar code readers and track-and-trace technology have not been applied on an integrated, comprehensive basis for the packaging of oral syringes in the hospital pharmacy. The potential to reduce medication errors using this technology is thus significant. Automated systems have been developed by Baxa, Inc., For Health Technologies, Inc., Intelligent Hospital Systems and others for the automated filling of injectable syringes.

For example, U.S. Pat. Nos. 6,991,002; 7,017,622; 7,631,475 and 6,976,349 are all drawn to the automated removal of a tip cap from an empty syringe, the placement of the tip cap at a remote location, and the replacement of the tip cap on a filled syringe. U.S. Pat. Nos. 7,117,902 and 7,240,699 are drawn to automated transfer of a drug vial from storage to a fill station. U.S. Pat. No. 5,884,457 shows a method and apparatus for filling syringes using a pump connected by a hose to a fluid source. U.S. Pat. No. 7,610,115 and Application Publication 2010/0017031 show an Automated Pharmacy Admixture System (APAS). U.S. Application Publication 2009/0067973 shows a gripper device for handling syringes of different diameters with tapered or angled gripper fingers. U.S. Pat. No. 7,343,943 shows a medication dose under-fill detection system. U.S. Pat. No. 7,260,447 shows an automated system for fulfilling pharmaceutical prescriptions. U.S. Pat. No. 7,681,606 shows an automated system and process for filling syringes of multiple sizes. U.S. Pat. No. 6,877,530 shows an automated means for withdrawing a syringe plunger. U.S. Pat. No. 5,692,640 shows a system for establishing and maintaining the identity of medication in a vial using preprinted, pressure sensitive, syringe labels.

The foregoing reference machines for packaging injectable syringes. The packaging process required for injectable syringes is significantly different than that for oral syringes. Injectable syringes must be packaged in a sterile environment, as the medication is injected into the body. This requirement adds cost and complexity to the machine. Injectable medications, when packaged on a just-in-time basis as with the Baxa, For Health Technologies, and Intelligent Hospital System machines, must typically be prepared by the machine before the medication is filled into the syringe. The medication preparation process involves diluting the medication or reconstituting the medication from a powdered state with water. This process adds expense and slows down the packaging process as well. The Intelligent Hospital Systems syringe packaging system is designed to be used to package cytotoxic medications which are hazardous. To avoid harm to the operator, this machine uses a robot located within an isolating barrier at considerable cost. The Baxa, For Health Technologies, and Intelligent Hospital System machines require the use of expensive disposable product contact parts when a different medication is to be filled. The foregoing machines are not suitable for packaging oral syringes due to their capital cost, complexity, slow production rates, inability to handle oral medication containers, the requirement of expensive disposable contact parts, and other features that add unnecessary cost and complexity to the process for filling and packaging oral syringes. Consequently, existing automation does not address the needs of medical institutions desiring an affordable pharmacy automation system for patient safety, prescription tracking and improved productivity in the filling and packaging of oral syringes. The present invention was developed to fill this void.

Oral syringes are manufactured in a variety of sizes with differing tip and plunger configurations, as described in part above. Moreover, oral medications are commonly provided and/or stored in bulk form in variously sized, manufacturer-supplied (OEM) bottles or containers having threaded screw caps that must be removed and replaced between uses. Under the prior art, in order to fill an oral syringe from the manufacturer-supplied container, the original container cap must be replaced with a cap that allows insertion of an oral syringe nozzle. Baxa™ sells an "Adapta-Cap"™ bottle adapter in a variety of sizes that replaces the OEM caps to convert a standard prescription or manufacturer bottle into a filling device for oral syringes. These Adapta-Cap™ bottle adapters are screw-on caps with open center-holes capable of accepting an oral syringe nozzle, and a tethered closure. This enables an oral syringe to enter its center hole and withdraw an amount of liquid from the medication container while the medication container is positioned upside down. Unfortunately, the Adapta-Cap™ bottle adapters have no internal valves and are not self-sealing. Thus, for the syringe to be removed from the medication container, both syringe and medication bottle must be up-righted. Once up-righted, the syringe can be removed from the up-righted medication bottle with no leakage. If the medication bottle requires shaking at any given time, it must be done manually or in a separate shaker while upright when using the prior art Adapta-Cap™.

It is known that an adapter cap can include a self-sealing valve for this purpose. For example, U.S. Pat. No. 8,459,312 to Manera et al. (Comar) issued Jun. 11, 2013 shows an adapter to be pressed into the neck of a bottle to receive a syringe for accessing the bottle contents by a syringe. The adapter has a normally closed valve located at that distal end to prevent the contents from leaking out of the bottle if the bottle is inverted. A very similar construct was shown in United States Patent Application 20110130740 by Levy (Baxa) published Jun. 2, 2011 (now abandoned). U.S. Pat. No. 4,493,348 shows a method and apparatus in which oral syringes can be filled using a screw-on adapter cap 12 for connecting the bulk medicine container 10 and a syringe 14 so that the liquid medication can be transferred from the bulk container 10 into the syringe barrel 20. The syringe is inserted into a nozzle 88 of the adapter cap 12 and displaces a detent valve 92 (see U.S. Pat. No. 4,493,348 FIG. 6) that allows medicine to flow through the nozzle 88 into the syringe. When not in use the nozzle 88 may be closed off by a plug 50 attached to a tether 48. The adapter cap 12 is well-suited for manual filling of oral syringes but is not suitable for automated filling.

Additionally, all of the foregoing adapters allow a tapered tip oral syringe to enter a center hole and withdraw an amount of liquid from the medication container while the medication container is positioned upside down, allow an oral syringe be removed from the container while the container is inverted, without leaking, and allow the medication container to be shaken while it is positioned upside down without leaking. However, none can accommodate an oral syringe with a Luer-lock tip. The Luer-lock tip syringe, includes a circular hub about the oral syringe nozzle that screws into in a threaded sleeve on the medicine container cap (see FIG. 39). As a result of a worldwide International Standards Organization directive ISO-80369, certain syringe types will be required to employ Luer-lock fittings to reduce the risk of misconnections between tubes, IV's, enteral devices, etc. In order to accommodate this change, any syringe fill automation system or semi-automatic system suitable for use in a hospital setting should be able to interface syringes with a Luer-lock fitting to a medicine container equipped with an adapter cap that preferably allows insertion, filling and withdrawal in any orientation without leaking, and which preferably enables the medication container to be shaken without leaking. Thus, preferably, a system of filling oral syringes should interface both Luer-lock and tapered tip oral syringes with medicine containers equipped with the appropriate adapter cap. A self-sealing adapter cap may accomplish these goals.

Given the diversity of oral syringes and medicine containers available (and in use), any semi-automated (or fully-automated) system will need sufficient dexterity to manipulate all the myriad prescription bottles containing the pharmaceuticals to be dispensed as well as variously sized oral syringes with tapered and Luer-lock tips, bringing them together in a controlled environment to quickly and accurately fill and label each syringe and to verify its work as it proceeds in order to avoid errors in the process. Such a system would need to be reliably constructed so as to minimize downtime, quickly take and fill orders, be easy to clean and capable of maintaining an environment free from cross contamination. Such a system would also need to be able to interact with a human operator at multiple points in the operation.

Additionally, in-patient medical facilities such as hospitals are moving toward electronic prescription ("e-prescription") systems which use computer systems to create, modify, review, and/or transmit medication prescriptions from the healthcare provider to the pharmacy. While e-prescribing improves patient safety and saves money by eliminating the inefficiencies and inaccuracies of the manual, handwritten prescription process, any syringe fill automation system suitable for use in a hospital setting must interface with an existing e-prescription system (which records and transmits prescriptions to the pharmacy), and must be capable of filling prescription orders in a just-in-time environment.

SUMMARY OF THE INVENTION

The present inventors herein provide a semi-automated system suitable for use in a hospital setting for filling patient-specific doses of liquid medications to be administered by oral syringes on a just-in-time basis. The system enables hospital pharmacists to simplify and streamline their task, increasing the number of prescriptions that can be filled in a day, and improving patient safety and care by minimizing medication errors and the consequences that ensue.

The present invention also provides fourteen embodiments of a medication container adapter for oral syringe filling system. The preferred embodiment is a self-sealing valve which allows the container to remain in an inverted position for the entire time the syringes are being filled. In addition the container may be shaken without removal from the shake station.

BRIEF DESCRIPTION OF THE DRAWINGS

The objects, features, and advantages of the present invention will become apparent from the following detailed description of the preferred embodiments and certain modifications thereof when taken together with the accompanying drawings in which like numbers represent like items throughout and in which:

FIG. 5 is a composite view of six of the embodiments of container/syringe interfaces according to the invention. The container/syringe interfaces include closures and neck inserts meant to facilitate the connection of an oral syringe to a medication container for the purpose of drawing fluid out of the container.

FIGS. 6A and 68B are perspective views of an exemplary vision inspection station 9.

FIG. 6C shows an alternative articulating design for the backlight panel 97.

FIG. 7A is an enlarged perspective view of a semi-automated syringe fill station 5 for filling the syringes S.

FIG. 7C I is an enlarged perspective view of fixed yoke 82A illustrating how it is used.

FIG. 7C II is an enlarged perspective view of fixed yoke 82B illustrating how it is used.

FIG. 7C III is an enlarged perspective view of self-centering jaws 82C illustrating how they is used.

FIG. 7C IV is an enlarged perspective view of fixed yoke 82D illustrating how it is used.

FIG. 7D is a further enlarged perspective view of the loading carriage 70 of FIG. 7A.

FIG. 16B is a composite operational diagram illustrating the operation of the integral shaking mechanism 820 of FIG. 16A.

FIG. 17 is a perspective view of an alternative, remote medication container shake station 6.

FIG. 18 is a sequential illustration of the process for filling a syringe S using a standard commercially available "Baxa" cap 214;

FIG. 21 is a sequential illustration of the process for filling a syringe S using a PIBA (with valve) 212.

FIG. 35 is FIG. 29 is composite view (A and B) of a Baxa™ or Baxa™-equivalent manufacturer-supplied medication container cap modified with a duckbill valve to interface with a tapered tip oral syringe.

FIG. 37A illustrates a tethered protective cap for modified Baxa™ or Baxa™-equivalent manufacturer-supplied medication container cap with duckbill valve for use in semi-automatic operations.

FIG. 37B illustrates a separate protective cap for modified Baxa™ or Baxa™-equivalent manufacturer-supplied medication container cap with duckbill valve for use in fully automated operations.

FIG. 43 is a composite view (A and B) of the interaction between push-pull cap 224, grooved block 400 and yoke 82 according to the embodiments illustrated in FIGS. 40-42.

FIG. 44 is a composite view (A, B and C) of a valveless PIBA 210 retrofit to include an integral valve 225 (typically, a duckbill valve) for use with a tapered tip syringe.

DETAILED DESCRIPTION OF THE PREFERRED EMBODIMENTS

Figure 1:
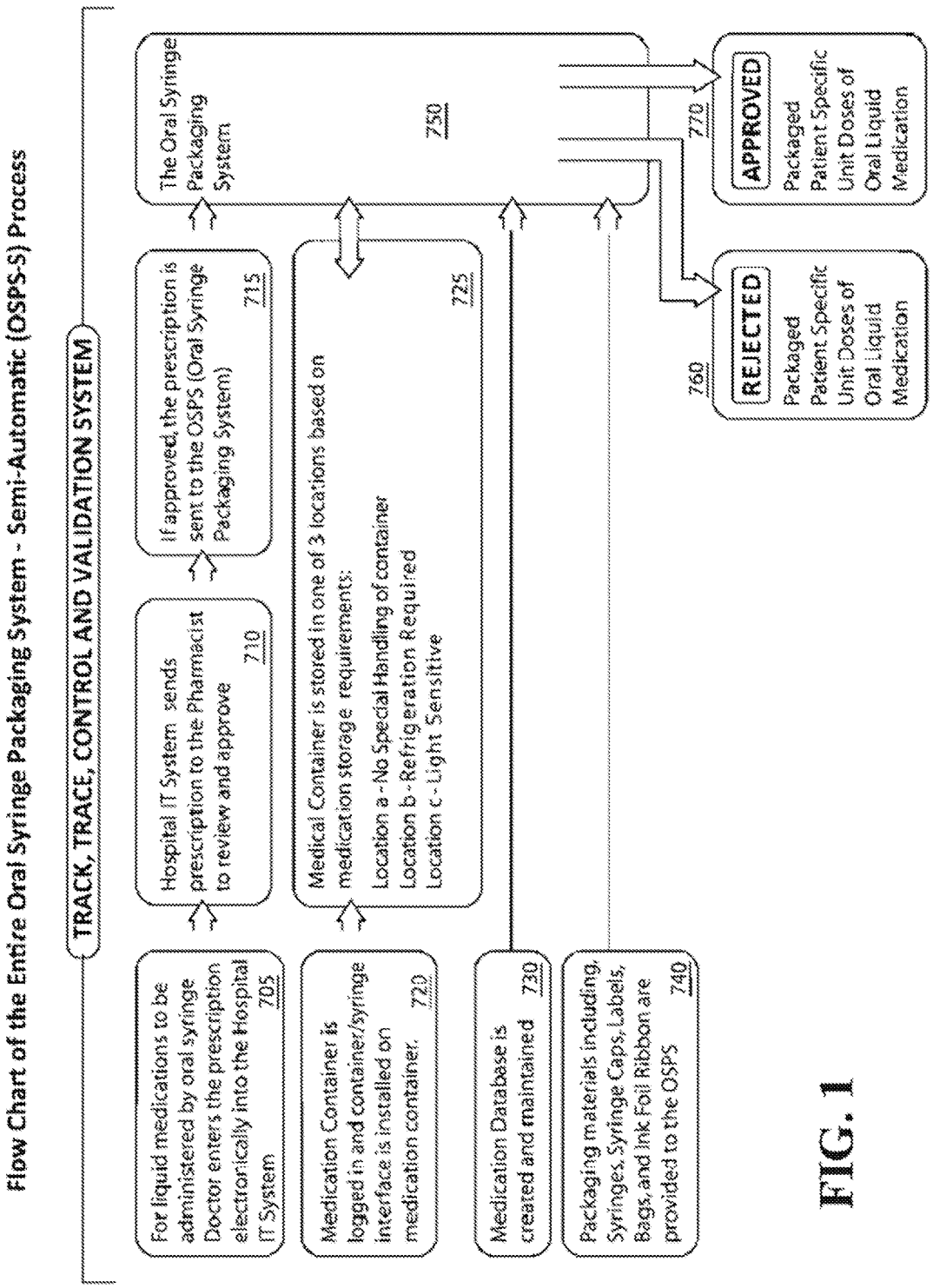
FIG. 1 is a flow chart of the overall method of the invention.

For the purposes of promoting an understanding of the principles of the invention, reference will now be made to the exemplary embodiment illustrated in the drawings and described below. The embodiment disclosed is not intended to be exhaustive or limit the invention to the precise form disclosed in the following detailed description. Rather, the embodiment is chosen and described so that others skilled in the art may utilize its teachings. It will be understood that no limitation of the scope of the invention is thereby intended. The invention includes any alterations and modifications in the illustrated device, the methods of operation, and further applications of the principles of the invention which would normally occur to one skilled in the art to which the invention relates.

Figure 27:
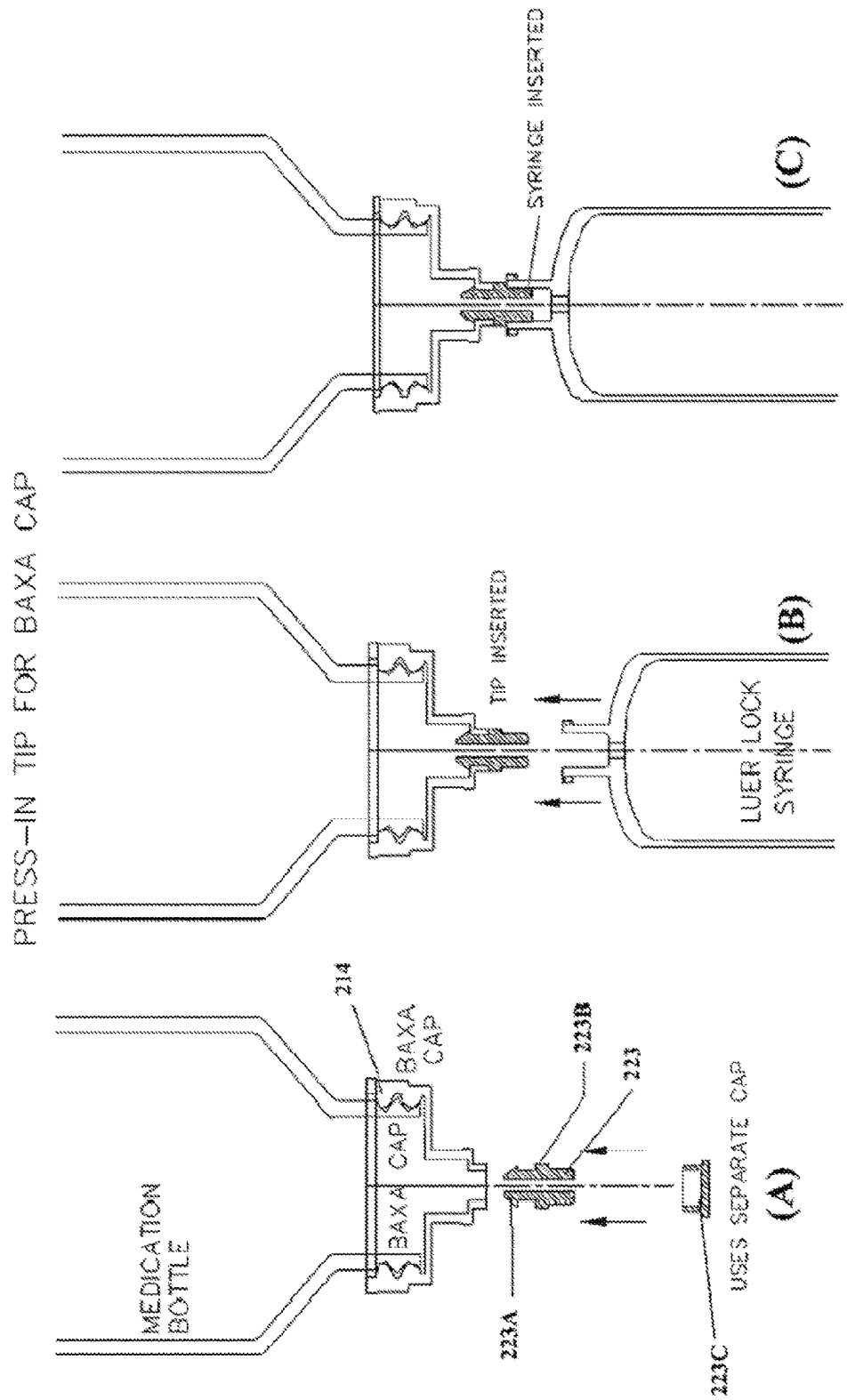
FIG. 27 is a composite view (A, B and C) of a press in tip 223 for a Baxa™ or Baxa™-equivalent manufacturer-supplied medication container cap to interface with a Luer lock oral syringe.
Figure 28:
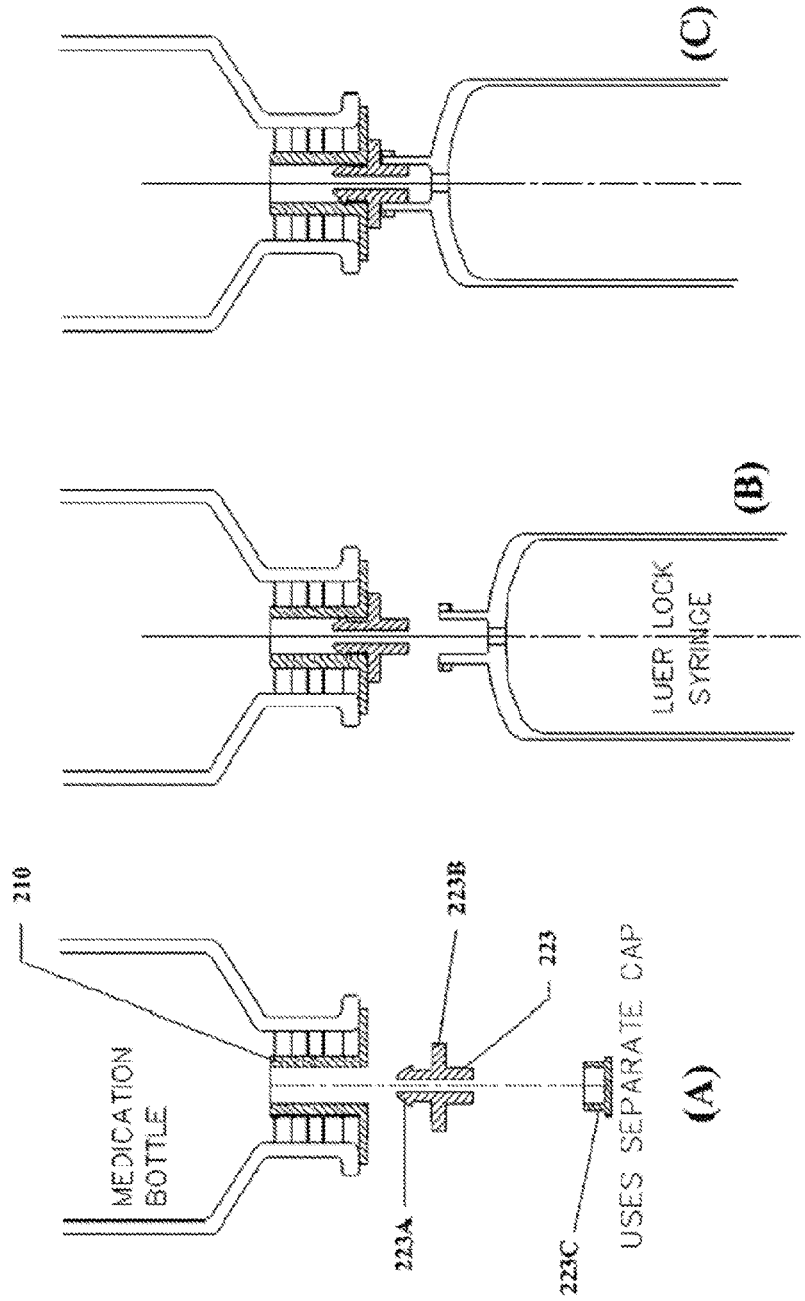
FIG. 28 is a composite view (A, B and C) of a press in tip 223 for a PIBA to interface with a Luer lock oral syringe.
Figure 29:
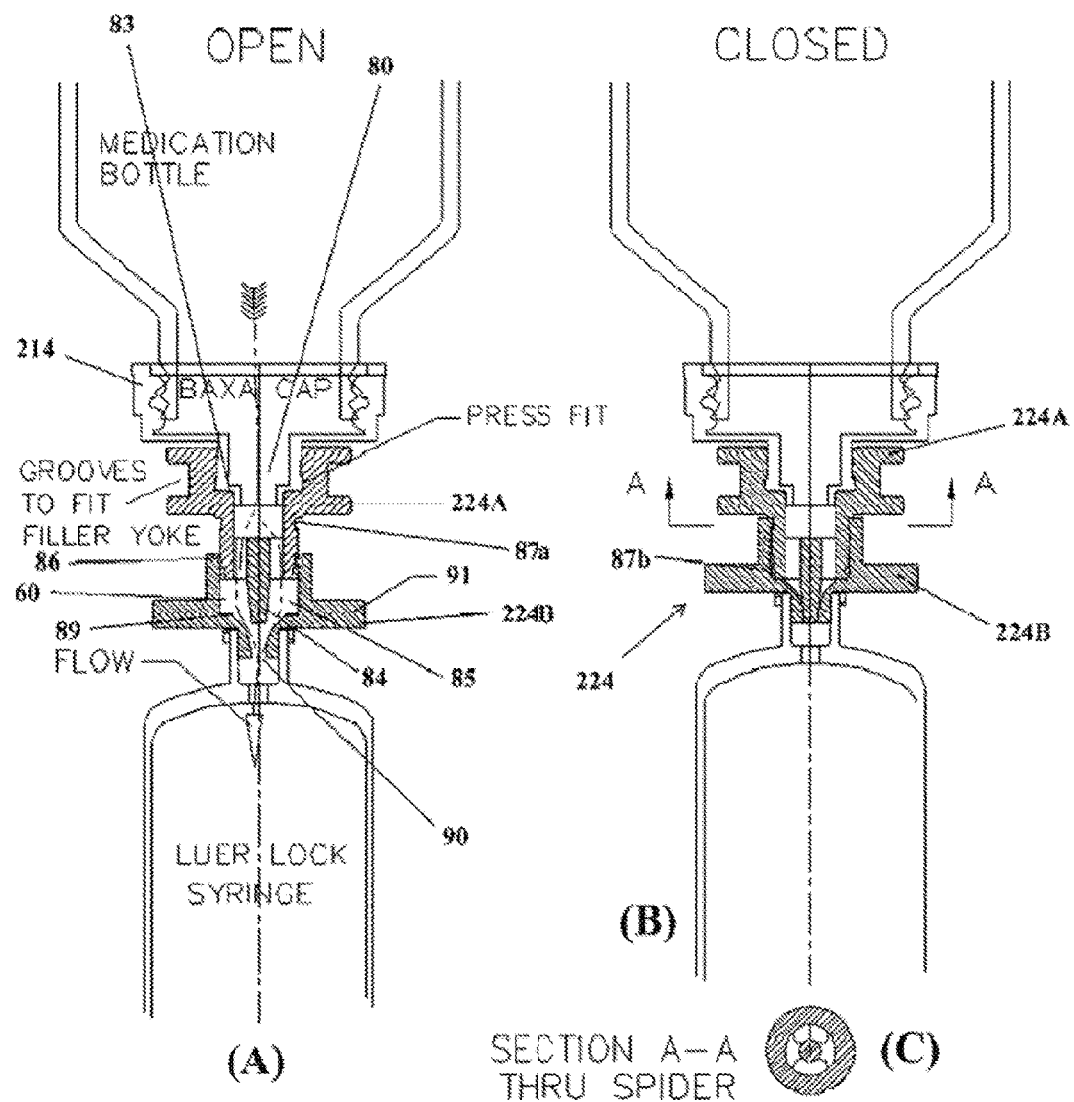
FIG. 29 is composite view (A, B and C) of a push-pull cap 224 for a Baxa™ or Baxa™-equivalent manufacturer-supplied medication container cap to interface with a Luer lock oral syringe.
Figure 30:
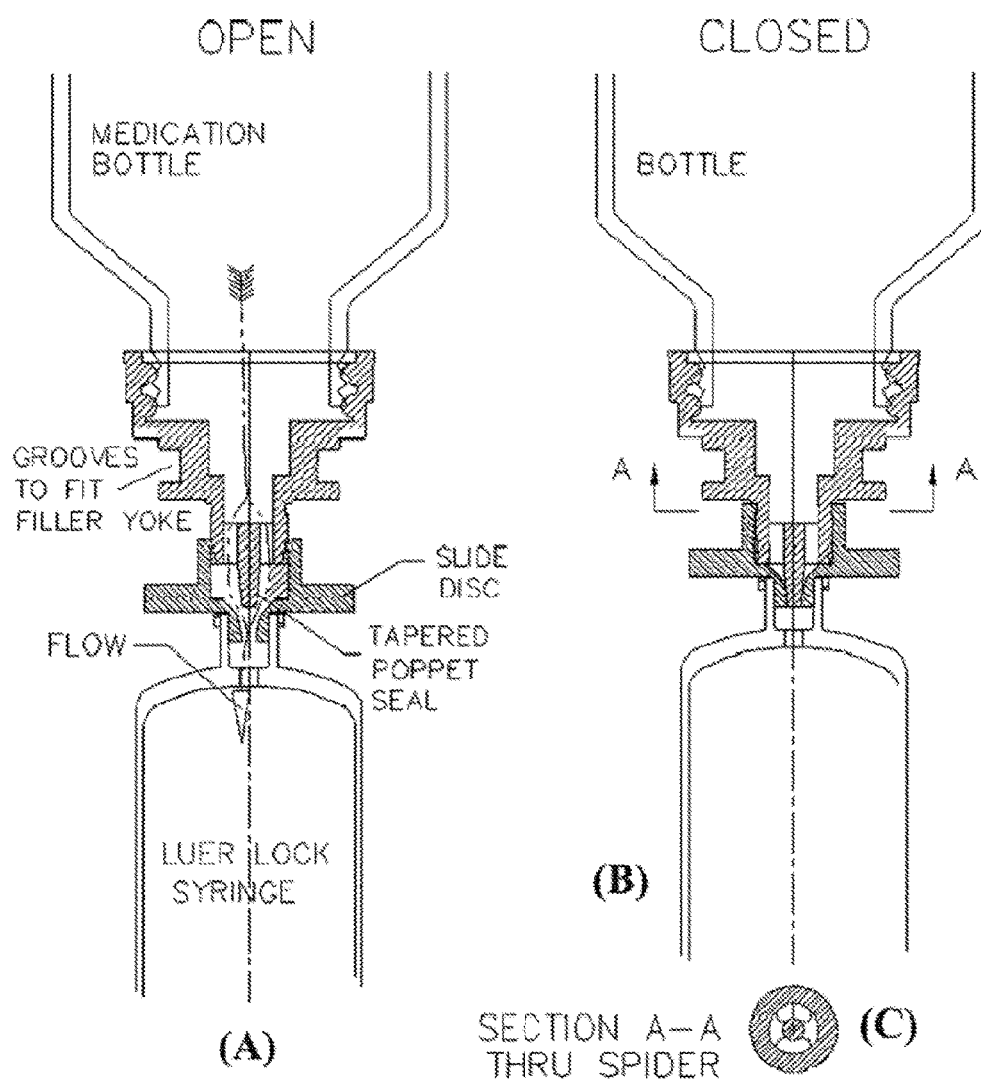
FIG. 30 is composite view (A, B and C) of a push-pull cap 224 made integral with a Baxa™ or Baxa™-equivalent manufacturer-supplied medication container cap to interface with a Luer lock oral syringe.
Figure 31:
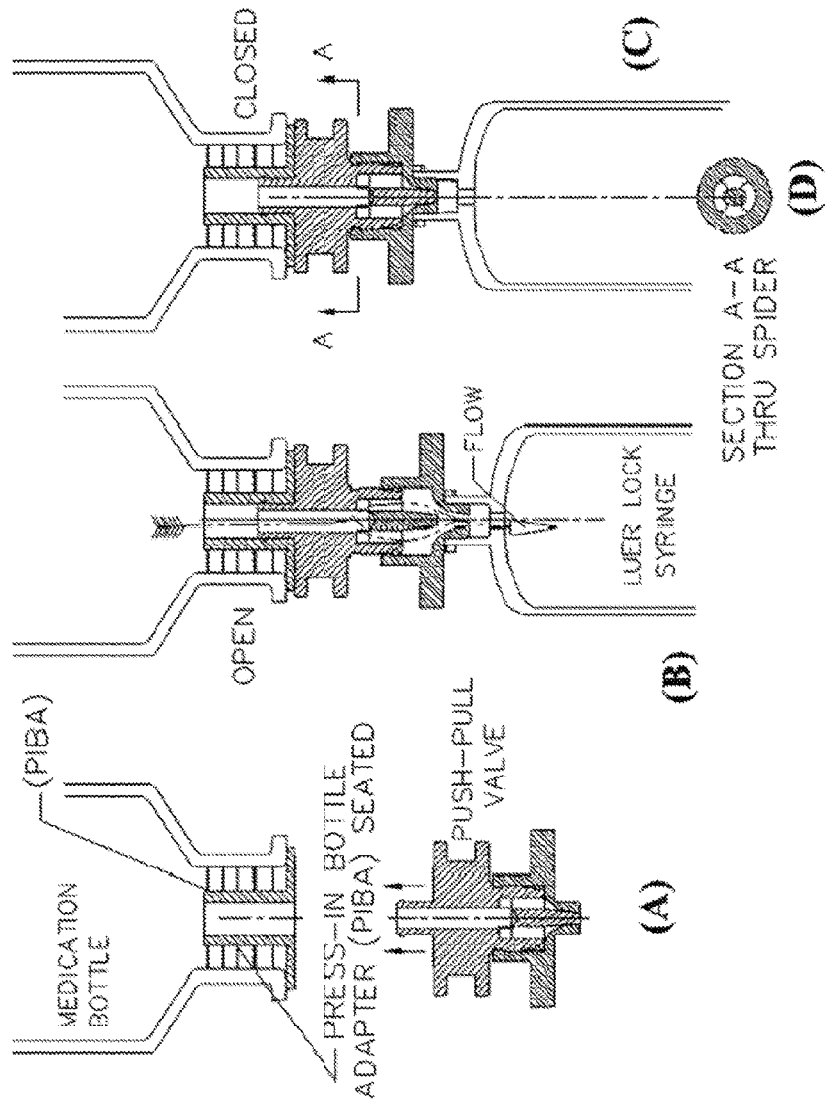
FIG. 31 is composite view (A, B, C and D) of a push-pull cap 224 for a PIBA cap to interface with a Luer lock oral syringe.
Figure 32:
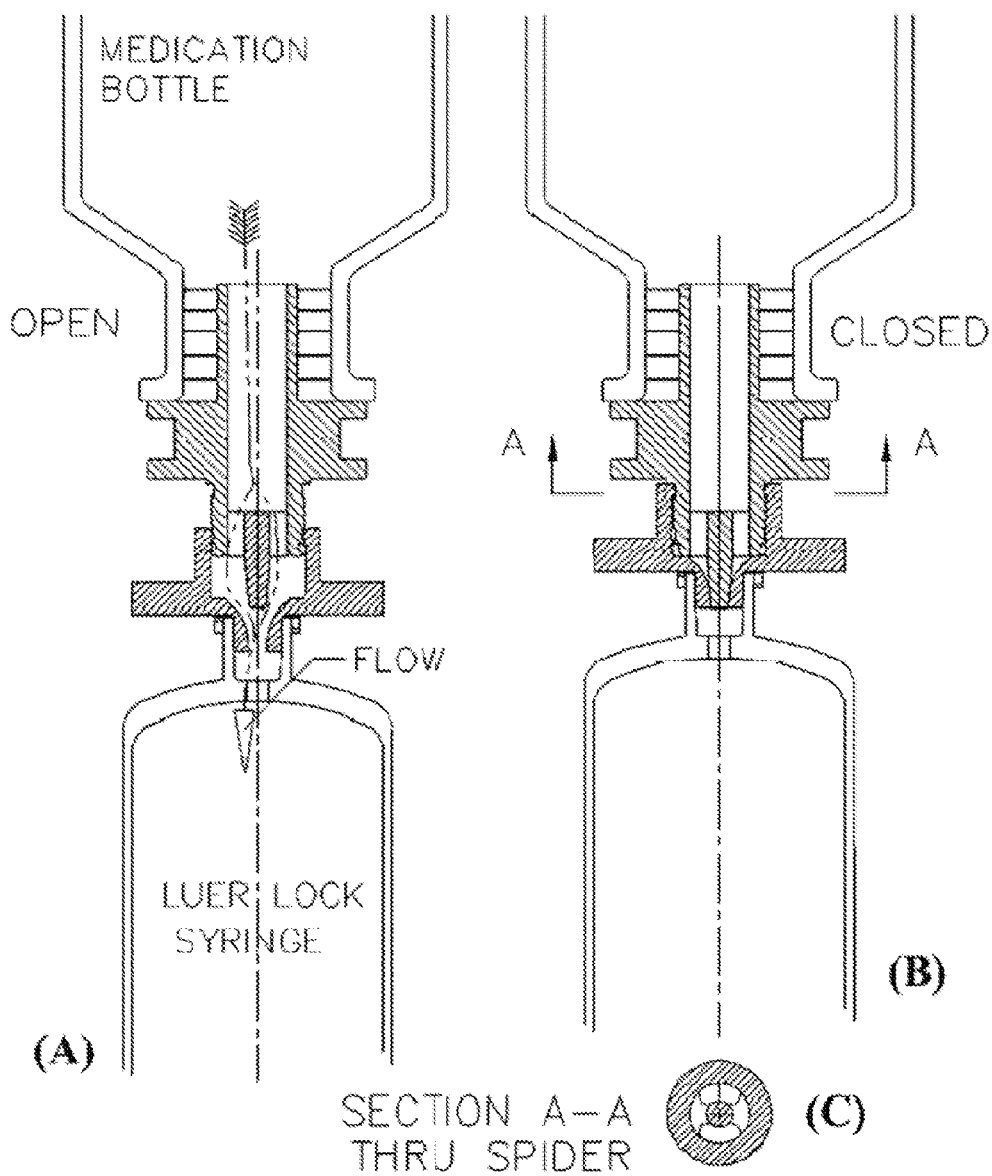
FIG. 32 is composite view (A, B and C) made integral with a push-pull cap 224 for a PIBA cap to interface with a Luer lock oral syringe.
Figure 33:
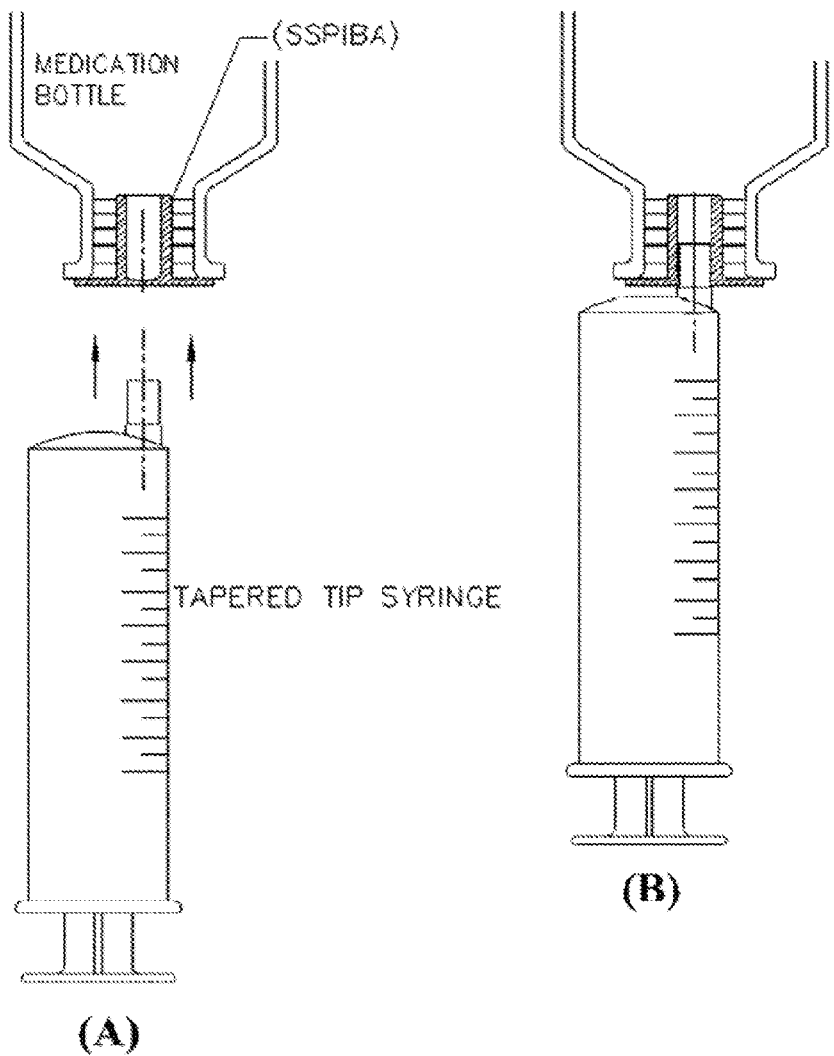
FIG. 33 is a composite view (A and B) of a self-sealing press in bottle adapter (SSPIBA) for use with a tapered tip syringe.

The present invention includes both the system hardware as well as the process for preparing and tracking prescriptions of oral syringes by a series of integrated manual and automated steps with respect to preparing the syringe and the bulk medicine, and subsequently bringing the series together for filling the former from the latter. The bulk medicine is typically supplied in manufacturer-supplied medicine containers with conventional screw-on caps. To facilitate processing the present system also envisions the use of one or more specialized adapter caps for interfacing with tapered or Luer lock type oral syringes; alternatively, another type of specialized cap may be provided to specification, or the OEM cap may be replaced or retrofitted with any available type of container/syringe interface to provide a penetrable orifice. As described more fully below, the retrofit may be accomplished in a number of ways. One solution is a press in bottle adapter (PIBA), e.g., a press-in plug inserted into the neck opening of a medication container which enables an oral syringe to enter its center hole and withdraw an amount of liquid from the medication container while the medication container is positioned up-side-down. Another is a modified manufacturer-supplied cap. Another is an adapter cap specially designed to modify a manufacturer-supplied cap to interface with a Luer lock oral syringe. Specifically, the present invention contemplates fourteen (14) container/syringe interface variations: (1) a valve-less press in bottle adapter (PIBA) 210 (FIG. 5); (2) a self sealing PIBA (SSPIBA) 212 with an integral valve (typically, either a linear or a Z-shaped slit) 213 (FIG. 5); (3) a standard manufacturer-supplied (Baxa™ or Baxa equivalent) valve-less medicine container cap 214 with opening (FIG. 5); (4) a modified manufacturer-supplied (Baxa™ or Baxa equivalent) medicine container cap 216 that is retrofit to include an integral valve 225 (typically, a duckbill valve) (FIG. 5); (5) a two-piece cap comprising an outer portion 220 with a common outer diameter for all standard sizes of medication container, and a self-sealing insert 212 (FIG. 5); (6) a cap 221 comprising a common outer diameter for all standard sizes of medication container and having an integral self-sealing insert 212 (FIG. 5); (7) a modified manufacturer-supplied (Baxa™ or Baxa equivalent) medicine container cap 214 that is retrofit to include a non-integral push-in tip 223 for interfacing with Luer lock oral syringes (FIG. 27); (8) a modified PIBA 210 that is retrofit to include a non-integral push-in tip 223 for interfacing with Luer lock oral syringes (FIG. 28); (9) a modified manufacturer-supplied (Baxa™ or Baxa equivalent) medicine container cap 214 that is fitted with a push-pull cap 224 for interfacing with Luer lock oral syringes (FIG. 29); (10) a modified manufacturer-supplied (Baxa™ or Baxa equivalent) medicine container cap 214 that is retrofit with an integral push-pull cap 224 for interfacing with Luer lock oral syringes (FIG. 30); (11) a modified PIBA 210 that is fitted with a push-pull cap 224 for interfacing with Luer lock oral syringes (FIG. 31); (12) a modified PIBA 210 that is retrofit with an integral push-pull cap 224 for interfacing with Luer lock oral syringes (FIG. 32); (13) a cap 226 comprising a common inner diameter for all standard sizes of medication container, fitted with an integral or separable valve 225 (typically, a duckbill valve), and having grooved rings to facilitate handling, positioning, etc. by the system according to the present invention (FIG. 34); and/or (14) a valveless PIBA 210 that is retrofit to include an integral valve 225 (typically, a duckbill valve) (FIG. 44). The chart below summarizes the fourteen (14) adapter cap variations according to the current invention:

| No. | Description of adapter interface | FIG. No. | Reference No. |
|---|---|---|---|
| 1 | valve-less press in bottle adapter (PIBA) | 5 | 210 |
| 2 | self sealing PIBA (SSPIBA) with an integral valve (typically, either a linear or a Z-shaped slit) | 5 | 212/213 |
| 3 | standard manufacturer-supplied (Baxa ™ or Baxa equivalent) valve-less medicine container cap with opening | 5 | 214 |
| 4 | modified manufacturer-supplied (Baxa ™ or Baxa equivalent) medicine container cap that is retrofit to include an integral valve (typically, a duckbill valve) | 5 | 216/225 |
| 5 | two-piece cap comprising an outer portion with a common outer diameter for all standard sizes of medication container, and a self-sealing insert | 5 | 220/212 |
| 6 | cap comprising a common outer diameter for all standard sizes of medication container and having an integral self-sealing insert | 5 | 221/212 |
| 7 | modified manufacturer-supplied (Baxa ™ or Baxa equivalent) medicine container cap that is retrofit to include a non-integral push-in tip for interfacing with Luer lock oral syringes | 27 | 214/223 |
| 8 | modified PIBA that is retrofit to include a non-integral push-in tip for interfacing with Luer lock oral syringes | 28 | 210/223 |
| 9 | modified manufacturer-supplied (Baxa ™ or Baxa equivalent) medicine container cap that is fitted with a push-pull cap for interfacing with Luer lock oral syringes | 29 | 214/224 |
| 10 | modified manufacturer-supplied (Baxa ™ or Baxa equivalent) medicine container cap that is retrofit with an integral push-pull cap for interfacing with Luer lock oral syringes | 30 | 214/224 |
| 11 | modified PIBA that is fitted with a push-pull cap for interfacing with Luer lock oral syringes | 31 | 210/224 |
| 12 | modified PIBA that is retrofit with an integral push-pull cap for interfacing with Luer lock oral syringes | 32 | 210/224 |
| 13 | cap comprising a common inner diameter for all standard sizes of medication container, fitted with an integral or separable valve (typically, a duckbill valve), and having grooved rings to facilitate handling, positioning, etc. by the system according to the present invention | 34 | 225/226 |
| 14 | valveless PIBA that is retrofit to include an integral valve (typically, a duckbill valve) | 44 | 210/225 |

Figure 38:
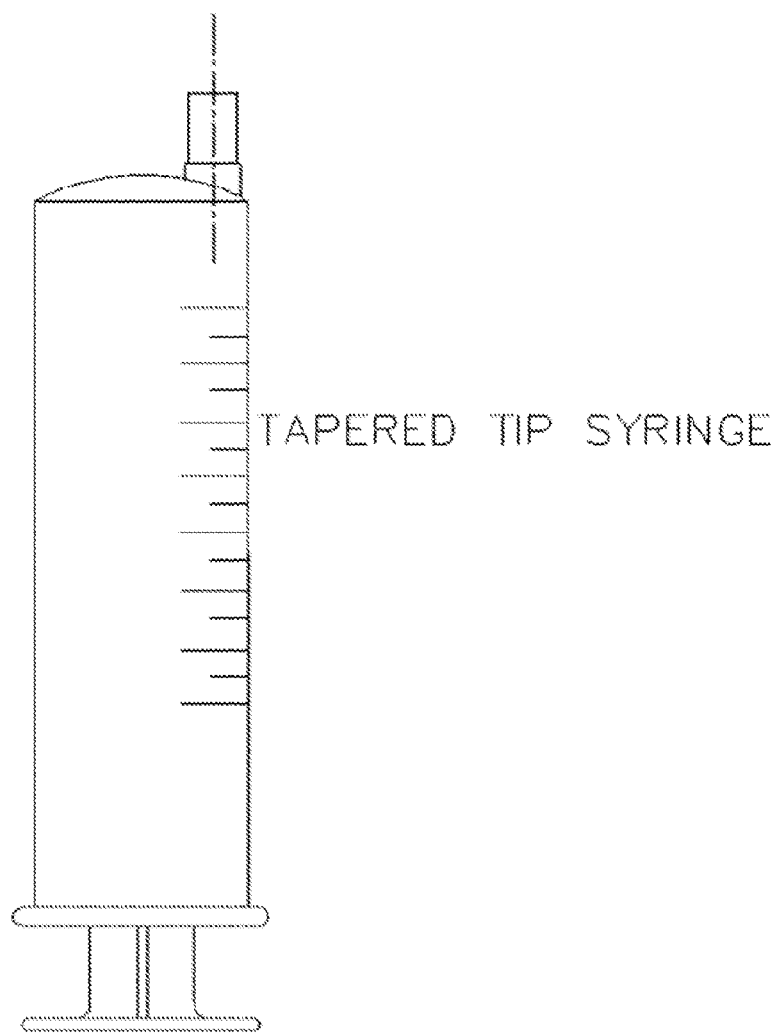
FIG. 38 is a side view of a tapered tip oral syringe.

FIG. 5 is a composite view of the first six of the embodiments of the container/syringe interfaces according to the invention. The embodiments shown in FIG. 5 are suited for use with a tapered tip syringe S as shown in FIG. 38. The tapered syringe includes an annular, tapered or cylindrical nozzle through which liquid medication must pass to enter or exit the body of the syringe. The nozzle contains an open central channel.

As shown in FIG. 5, two valveless embodiments include the PIBA 210 and OEM/Baxa Cap 214 at left, and four valved embodiments include the valved PIBA 212, the valved self-sealing PIBA 212 integrally formed into, or combinable with, the common diameter outer portion 220 or 221, and a modified/self-sealing OEM/Baxa Cap 216. All may be adapted to fit a variety of medicine bottle types and sizes.

The valved PIBA 212, OEM/Baxa Cap 216 and common outer diameter caps 220, 221 all include a self-sealing valve that closes when the syringe nozzle is removed to prevent leakage when the medication container is in the inverted position at the fill station.

Both PIBAs 210, 212 comprise a press-fitted open plug inserted into the neck opening of a medication container. This enables an oral syringe to enter its center hole and withdraw an amount of liquid from the medication container while the container is positioned up-side-down. This syringe filling procedure must be repeated for each syringe to be filled. If the medication container with open PIBA 210 requires shaking this must be done manually with the original screw cap replaced over the neck. The above procedure must be repeated every time shaking is required regardless of whether the same medication is being filled into multiple syringes. Also, the original cap must be placed over the Medication bottle and its press-in insert, during storage, to ensure cleanliness.

OEM/Baxa Caps 214 (see FIG. 5) are the commercially available "Baxa" screw on adapter caps which are applied to the necks of medication bottles to enable them to fill oral syringes. The standard commercially available "Baxa" cap consists of a female threaded cap to fit over medication bottles and is available in sizes to accommodate most medication containers. It enables an oral syringe to enter its center hole and withdraw an amount of liquid from the medication container while the medication container is positioned upside down. For the syringe to be removed from the medication container, both syringe and medication bottle must be up-righted. Once up-righted, the syringe can be removed from the up-righted medication bottle with no leakage. If the medication bottle requires shaking at any given time, it can be done manually or in a separate shaker by closing the tethered cap and fastening the bottle into the shaking mechanism (see FIG. 17 below).

The valved OEM/Baxa Cap 216 (see FIG. 5) is preferably modified/constructed with an elastomeric check valve member 225 held captive in the plastic cap body 219. Examples of self-sealing valves include check valves and simple diaphragms with a linear or a Z-shaped slit. Again, it is important to remember that valved interfaces 212, 216 can be left inverted at the filling station 5 (FIG. 2 III 5) and even shaken without leaking, whereas valveless interfaces 210, 214 (see FIG. 5) do not prevent leakage. Thus, valveless interfaces 210, 214 compel removal of the syringe/container combination from the filling station 5 after each filling operation.

Figure 19:
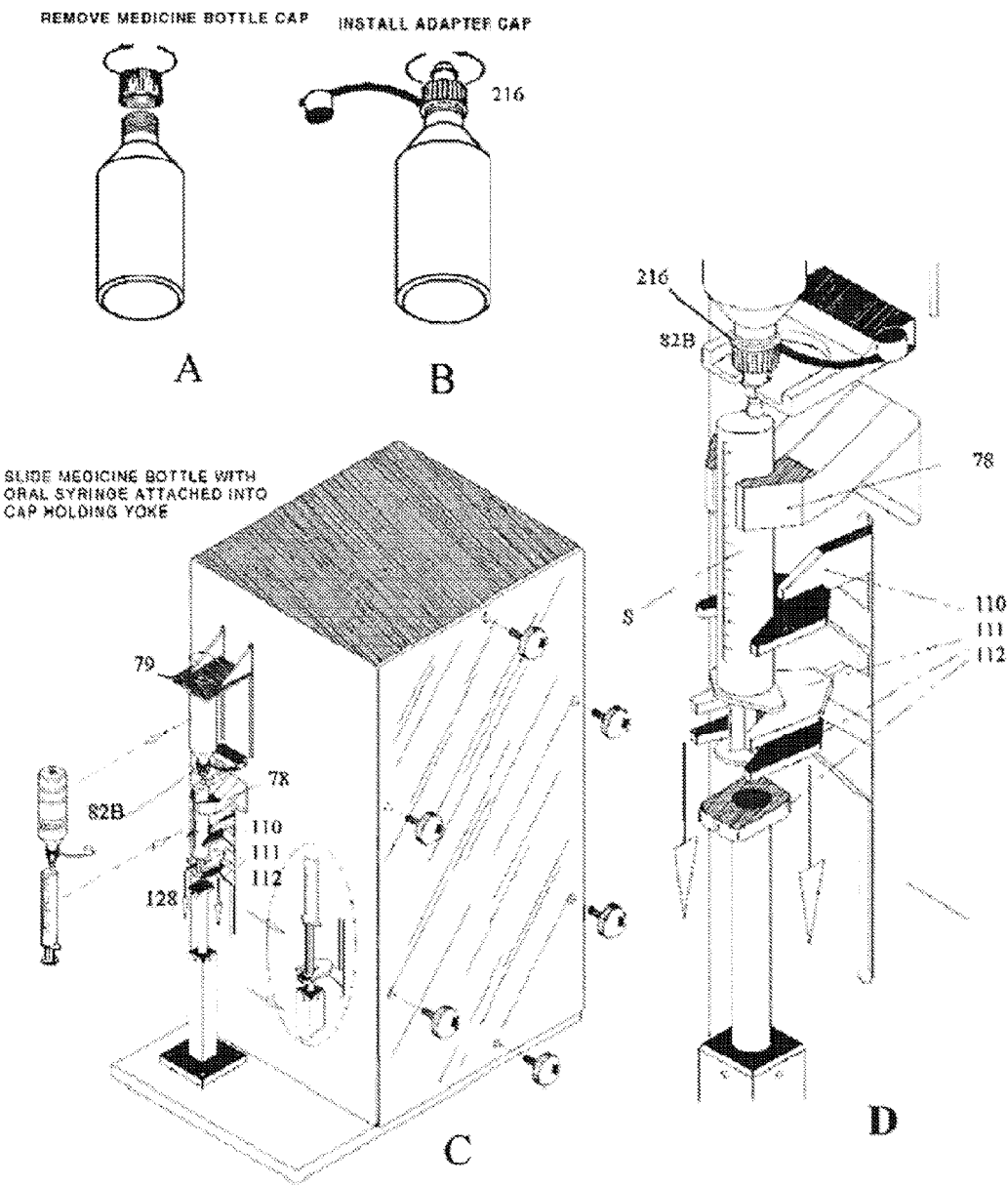
FIG. 19 is a sequential illustration of the process for filling a syringe S using an OEM-Baxa™ Cap with self sealing valve 216.

The elastomeric seal 225 (see FIG. 5) of the valved OEM/Baxa Cap 216 is fitted within an aperture in the flange of cap 219. In its simplest form the elastomeric seal 225 may be a resilient, penetrable membrane with a small hole or slot (such as a pinhole) punched at its center, and preferably formed of silicone or other rubber. The hole in the seal 225 expands as the tip of a syringe S is inserted to permit pressurization of the container 104 (see FIG. 19) and/or filling of the syringe (by vacuum) as described below. On withdrawal of the syringe tip the resilient elastomeric seal 225 returns to its original shape closing the hole and preventing leakage of the fluid contents of the bottle 104.

FIG. 5 also shows cross-sections of alternative container/syringe interfaces 210, 212 which comprise a PIBA fitted as a plug-in insert into the neck of the medicine container. The PIBA is an annular body sized to conform to the inside of the medicine container neck and adapted for a friction fit therein, and may be formed with ribs as described above for this purpose. The interface 212 defines a central conduit, and the elastomeric seal 213 is fitted within interface 212 across this conduit to serve as a penetrable seal as described above.

As still another option, any conventional cap, such as Baxa's AdaptaCap™ bottle adapter cap may be used (as shown in U.S. Pat. No. 4,493,348 referenced above) and simply modified or equipped by the manufacturer or aftermarket with a penetrable elastomeric seal such as check valve 225, or other suitable self-sealing valve. In yet another embodiment of the present invention, a container/syringe interface includes an outer portion 220, 221 that will have the same outer circumference for use on any of the standard sizes of medication containers. It can be used with a purchased, self-sealing insert, such as valved PIBA 212, or the insert can be integrally formed within the outer portion 221. The interface between the medication container and the self-sealing insert will hold the outer portion 220, 221 securely onto the top of the medication container, locating the outer part on center with the opening of the medication container. The cap with outer portion 220, 221 may also include a tethered protective cap (to protect the contents of the medication container from contamination, such as, for example, from dust or other airborne particles) similar to the Baxa type cap, as shown in FIG. 5. In one preferred embodiment, the 2D bar code, described in further detail below, is affixed to the top of the tethered cap. The common outer diameter of outer portion 220, 221 for all standard sizes of medication container caps can serve as a common means of locating the medication container on center with the yoke at the fill station. The common size of the flange 222 of the outer portion 220, 221 of the instant cap embodiment may also facilitate transportation of the medication containers when used with a carousel designed to hold a single diameter syringe/container interface.

FIG. 44 shows a composite view of another valved embodiment of the container/syringe interface for use with a tapered tip syringe: valveless PIBA 210 with integral or non-integral duckbill valve 225. This embodiment also may be adapted to fit a variety of medicine bottle types and sizes. The valveless PIBA 210 with duckbill valve 225 comprises a press-fitted open plug inserted into the neck opening of a medication container. An elastomeric check valve member 225 is then inserted into the center hole of PIBA 210. Examples of self-sealing valves include check valves and simple diaphragms with a linear or a Z-shaped slit. The hole in the seal 225 expands as the tip of a syringe S is inserted to permit pressurization of the container 104 (see FIG. 19) and/or filling of the syringe (by vacuum) as described below. On withdrawal of the syringe tip the resilient elastomeric seal 225 returns to its original shape closing the hole and preventing leakage of the fluid contents of the bottle 104. The presently described valved interface 210/225 can be left inverted at the filling station 5 (FIG. 2 III 5) and even shaken without leaking. However, the original cap must be placed over the Medication bottle and its press-in insert, during storage, to ensure cleanliness.

Figure 39:
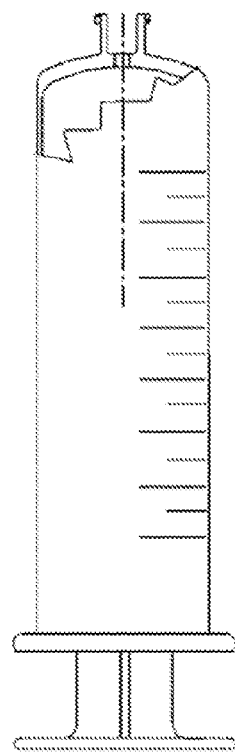
FIG. 39 is a side view of a Luer lock oral syringe.
Figure 40:
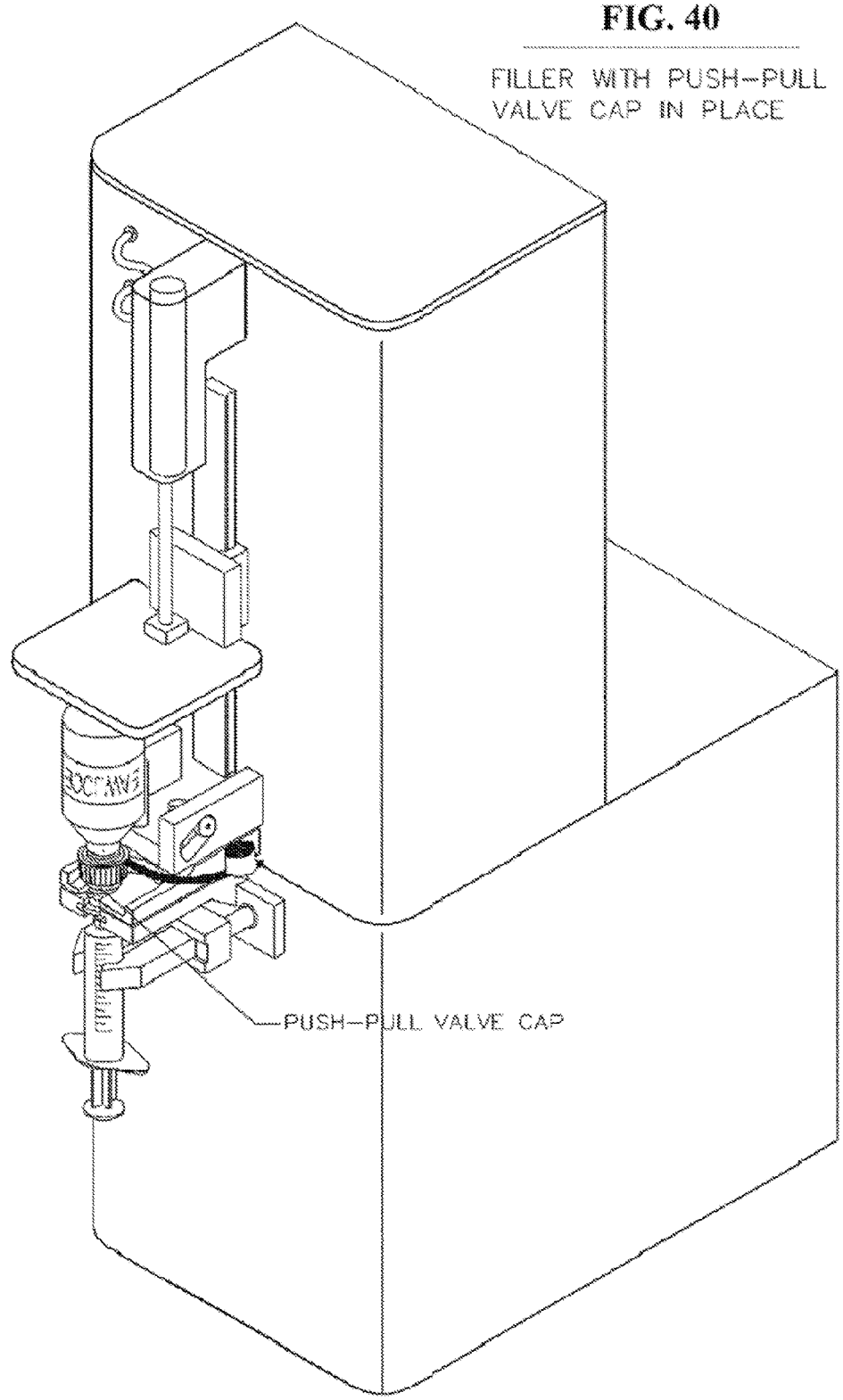
FIG. 40 is a perspective view of filling station 5 according to another embodiment of the present invention comprising a grooved block 400 for actuating push-pull adapter cap 224.

Additional preferred embodiments are illustrated with reference to FIGS. 27-37 and 39. FIG. 39 depicts a Small Bore Luer Lock (also referred to herein as a "Luer-lock") syringe) syringe which has an inlet/outlet opening flush with the top edge of the syringe body and bordered by an annular flange which creates a female connection point for a male nozzle to fill the syringe body with liquid medication through the inlet/outlet point. FIG. 27 is a composite view (A, B & C) of a modified manufacturer-supplied (Baxa™ or Baxa equivalent) medicine container cap 214 that is retrofit to include a non-integral push-in tip 223 for interfacing with Luer lock oral syringes, shown in cross-section. Push-in tip 223 is preferably composed of an annular body having a tapered distal flange 223A, flange 223A having a diameter that decreases towards the distal end of tip 223 for insertion into the nozzle of the manufacturer-supplied medication container cap 214. Tip 223 further comprises an annular flange 223B (having a diameter slightly larger than the diameter of the nozzle opening for cap 214) at its midpoint to prevent tip 223 from sliding all the way into cap 214. The end of tip 223 opposite tapered flange 223A is sized to fit snugly within the outer flange of Luer Lock Syringe S, as shown in FIG. 27C. This design requires the medication bottle to be upright while the syringe is inserted into the medication bottle nozzle. Then, both medication bottle and attached syringe are inverted as a unit and placed into the filler, as will be described. When syringe S is filled, both medication bottle and syringe are uprighted and the filled syringe is removed from the medication bottle. Tip 223 may use a separate cap 223C to prevent spillage of the contents of the medication bottle when syringe S is not attached to tip 223.

FIG. 28 is a composite view (A, B & C) of a modified PIBA 210 that is retrofit to include a non-integral push-in tip 223 for interfacing with Luer lock oral syringes. As in FIG. 27, tip 223 comprises a tapered distal flange 223A, flange 223A having a diameter that decreases towards the distal end of tip 223 for insertion into the nozzle of the PIBA cap 210, while the opposite end of tip 223 is sized to fit snugly within the outer flange of Luer Lock Syringe S, as shown in FIG. 28C. Tip 223 may use a separate cap 223C to prevent spillage of the contents of the medication bottle when syringe S is not attached to tip 223.

FIG. 29 is a composite view (A, B & C) of a modified manufacturer-supplied (Baxa™ or Baxa equivalent) medicine container cap 214 that is fitted with a push-pull cap 224 for interfacing with Luer lock oral syringes. Cap 224 comprises two separately formed nozzle sections that are slidably connected in a male-female link. A stationary portion 224A for attachment to a medication bottle comprises an annular body with a central passage 80 therethrough, the central passage 80 being defined by an inner wall having a specific progression of diametric variations. At one end of the body of stationary portion 224A, where stationary portion 224A attaches to the top of a manufacturer-supplied (Baxa™ or Baxa equivalent) medicine container cap 214, central passage 80 has a relatively large diameter sized to conform to and receive the conventional Baxa™ oral medication cap with syringe aperture 214 as shown in FIG. 5. It will be understood by one of ordinary skill in the art, however, that stationary portion 224A may be sized to fit a Baxa™-equivalent manufacturer-supplied cap based on design preference. Central passage 80 continues through stationary portion 224A at a diameter sized to accommodate the upper, smaller-diameter nozzle portion of the conventional Baxa™ oral medication cap 214, wherein the two diameters of central passage 80 connect to define a shoulder 83 for press-fit anchoring of the conventional Baxa™ (or Baxa™-equivalent) oral medication cap 214. At a midpoint of the smaller diameter portion of central passage 80, a tapered elastomer poppet 84, as will be described further herein, is anchored. The outer wall of stationary portion 224A may further comprise annular grooves for alignment with the yoke of the filling station, as further described herein.

At the distal end of stationary portion 224A opposite its attachment with the manufacturer-supplied medication container cap 214, stationary portion 224A is slidably attached to a second, sliding portion 224B of push-pull cap 224. Sliding portion 224B also comprises a generally annular body with a central passage 85 therethrough, the central passage 85 being defined by an inner wall having a specific progression of diametric variations. At a first end, proximate the connection point between stationary 224A and sliding 224B portions of cap 224, channel 85 has a diameter sized to fit securely around the outer diameter of the distal end of stationary portion 224A. Channel 85 continues through sliding portion 224B to a shoulder 89 at the base of cap receiving chamber 60. Past shoulder 89, channel 85 progressively narrows in diameter, terminating in a nozzle 90 at the distal end of sliding portion 224B. Nozzle 90 is sized to fit securely around the tip of poppet 84 when cap 224 is closed to provide a secure, water tight fit between nozzle 90 and poppet 84. This configuration prevents any fluid medications from leaking from the medication bottle when inverted upon removal of the syringe from nozzle 90.

Cap 224 comprises a tab and groove locking mechanism to ensure positive locking between stationary 224A and sliding 224B portions of cap 224 in both open (FIG. 29 at A) and closed (FIG. 29 at B) positions. The locking mechanism comprises an annular tab 86 extending from the inner wall of channel 85 and flush with the distal end of sliding portion 224B. Tab 86 corresponds in height and width to two grooves 87a, 87b in the outer wall of stationary portion 224A. When cap 224 is open, as shown in FIG. 29 (at A), tab 86 fits securely into groove 87b, which is located proximate the distal end of stationary portion 224A, creating a chamber 60 within channel 85 to allow liquid medication to flow from manufacturer-supplied medication container cap 214 through channel 80 and around poppet 84 into channel 85 and out through nozzle 90 into the oral syringe during filling. Poppet 84 is anchored within stationary portion 224A using one or more anchor points (see FIG. 29 at C, showing cross-section A-A through stationary portion 224A) that allow liquid to flow past poppet 84 as indicated by the dotted line in FIG. 29 (at A). Grooves 87a, 87b are spaced such that, when sliding portion 224B is pushed towards stationary portion 224A, tab 86 settles in groove 87a when the tip of poppet 84 is flush with the distal end of sliding portion 224B forming a water tight seal with nozzle 90. The exterior wall of sliding portion 224B comprises an annular slide disc 91 to allow force to be applied along the main axis of sliding portion 224B to open and close cap 224. At the distal end of sliding portion 224B proximate its connection with syringe S, the outer diameter of sliding portion 224B is sized to fit inside the female nozzle of a Luer lock oral syringe.

This design enables opening and closing the flow of medication to the Luer lock oral syringe while the medication container is inverted. As such, the time to load and unload, or upright and invert, the medication container between syringe fillings is eliminated. In addition, the medication container can also be shaken in an inverted position before, during or after a syringe filling operation, when the medication so requires, as will be described. The design also allows for placement of the medication container bearing cap 224 into the Syringe Filler (to be described) via a yoke in an automated or semi-automated process, and for slide disc 91, which controls the opening and closing of cap 224, to be automated for use in a fully or semi-automated process. Push-pull cap may further comprise a 2D barcode, as further describe herein, on a bottom edge of the slide disc 91 (facing up when medication container is inverted for filling operations) or elsewhere on cap 224 to enable easy tracking of the medication container bearing that cap. Alternately, the 2D barcode described herein may be placed on the base of the medication container.

FIG. 30 illustrates the push and pull-cap 224 of FIG. 29 wherein the distal end of stationary portion 224A is made integral with medication container cap 214 by co-molding or like means known in the art. In this embodiment, the threaded portion of cap 214 may be provided in several standard sizes, such as 20 mm, 24 mm, 28 mm, 33 mm, etc., or in sizes which are chosen as a matter of design or operator preference.

FIGS. 31 and 32 illustrate push-pull cap 224 which is made separate and integral, respectively, with a valveless PIBA cap. Instead of channel 80, at its end proximate the medication bottle, being sized to fit over a Baxa™ or Baxa™-equivalent manufacturer-supplied medication container cap, it is instead sized to fit within outer wall of stationary portion 224A, which in turn is sized to fit within the open channel of a PIBA cap as shown. In FIG. 32, outer wall of stationary portion 224A is made integral with the inner channel of a PIBA cap, and/or is fitted with annular elastomeric rings to provide a press fit within the opening of a medication container.

Figure 34:
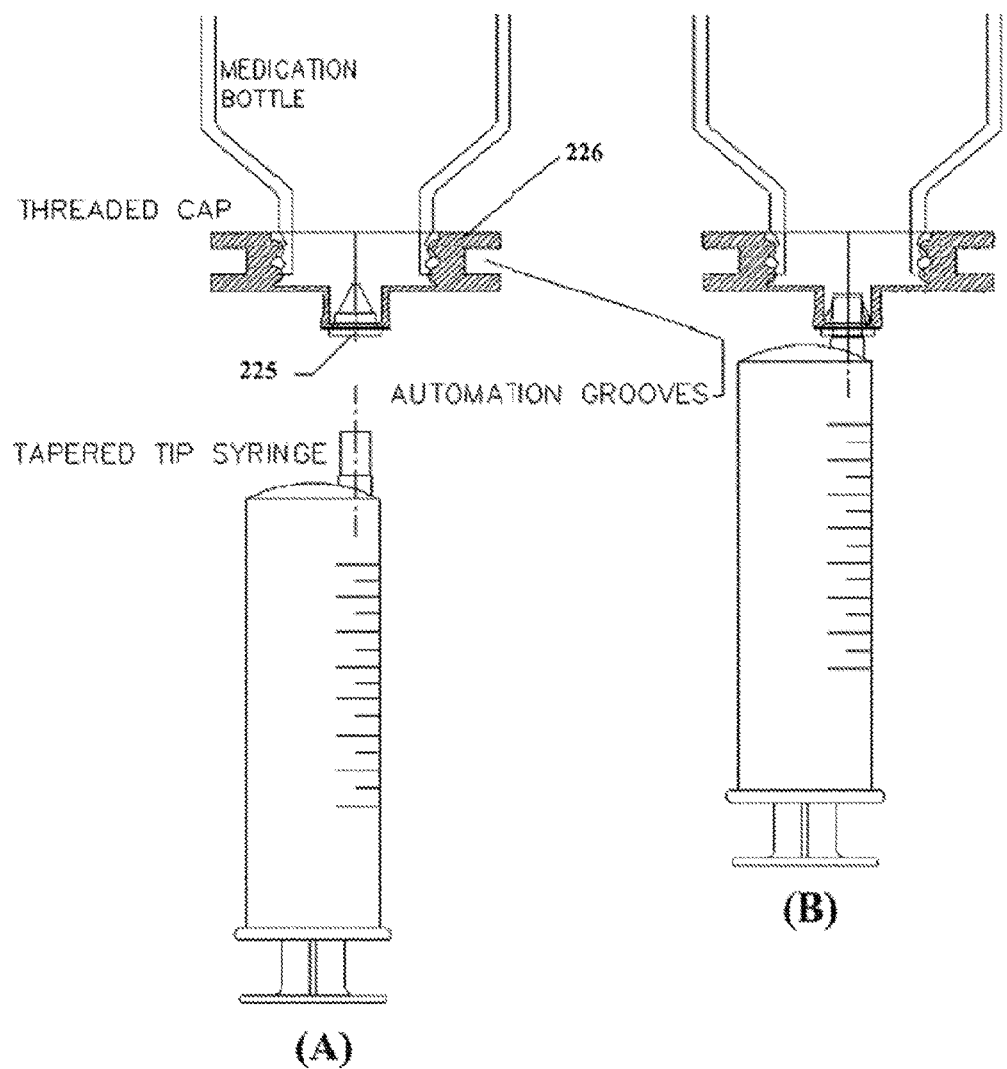
FIG. 34 is a composite view (A and B) of a threaded cap modified with a duckbill valve having automation grooves for use with a tapered tip syringe.

FIG. 34 depicts a cap 226 comprising nozzle fitted with an integral or separable valve 225 (typically, a duckbill valve, as shown in FIG. 34). The threaded inner wall of cap 226 may be provided in several standard sizes, such as 20 mm, 24 mm, 28 mm, 33 mm, etc., or in sizes which are chosen as a matter of design or operator preference. The outer wall of cap 226 comprises two annular rings defining a groove to accept the fingers of the automated or semi-automated arms of the filling station, as will be described. Grooves provided on the outside of the medication container cap not only fit into the yoke of the syringe filling apparatus and hold the medication bottle securely, but also locate the medication container on a reference center line. Grooves may also serve as a means to handle, move and position the medication container during selection from a medication container library as will be described.

Figure 36A:
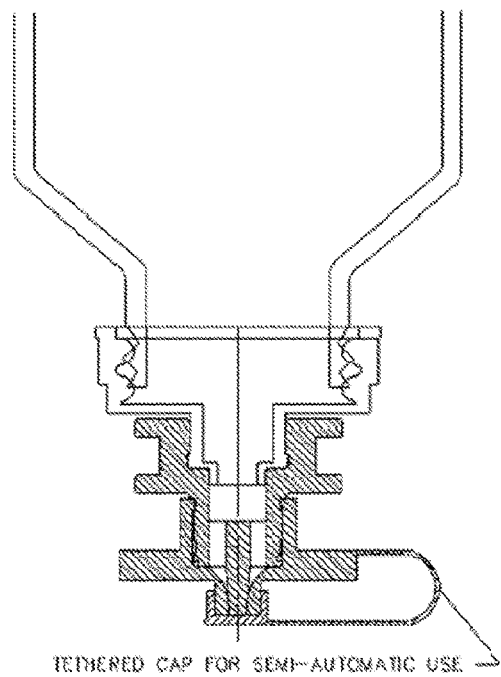
FIG. 36A illustrates a tethered protective cap for push-pull cap 224 for use in semi-automatic operations.
Figure 36B:
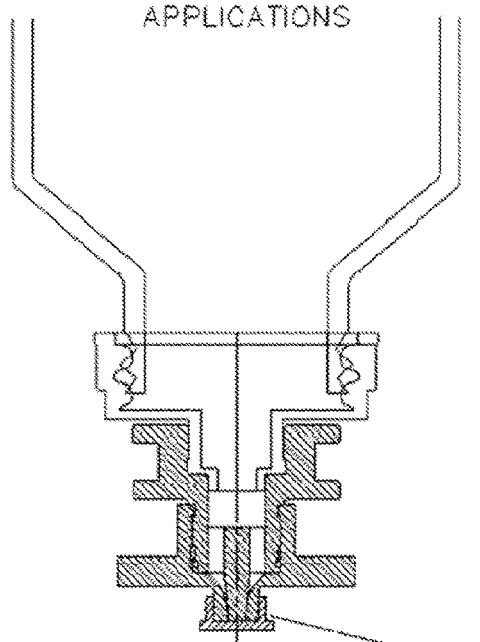
FIG. 36B illustrates a separate protective cap for push-pull cap 224 for use in fully automated operations.

FIGS. 36-37 depict protective caps for the medication container caps described herein. Each protective cap is designed to fit securely over and cover the nozzle of each of the medication container caps described herein such that the medication container may be inverted without the attached protective cap falling off. For automated or semi-automated systems, as described herein, a separable cap can be used (see FIGS. 36B and 37B). For semi-automated systems only, a tethered protective cap may be used (see FIGS. 36A and 37A).

Each adapter cap may be barcoded with a unique identifier number. Where a tethered protective cap is used, the barcode may appear on the protective cap instead of or in addition to on the adapter cap itself. In addition, molded surface features or textures may be provided on the outer surface of each cap to provide a gripping surface.

In addition, one skilled in the art should understand that the aftermarket valveless cap (e.g., Baxa Adapta-Cap™ bottle adapter) and the adapter 2 as described above and in other embodiments of the present invention may essentially be combined in a single unitary structure. Specifically, the press-on container cap 214 may, if desired, be co-molded with the valve adapter cap 2 to form a unitary adapter cap. In addition, the valve adapter cap 2 may include one or two flanges to enable the container to be mechanically-handled for storage or transport in a fully-automated filling system such as shown and described in Applicant's co-pending U.S. patent application Ser. No. 13/236,577 filed 19 Sep. 2011.

A preferred embodiment of the invention is now described with reference to the PIBA with valve interface 212 of FIG. 5. Process and system configuration variations specific to each of the container/syringe interfaces are also described below.

The support fixture illustrated in FIG. 7A comprises a fixed-position container holding yoke 82 that engages the container/syringe interface 210, 212, 214, 216 (see FIG. 5) suspending the assembly. Note that the fourteen syringe-filling closure variations containe/syringe interfaces 210, 212, 214, 216, 220, 221, 226, and the Baxa™-type or PIBA variations for caps 223 and 224, both integral and separable, suitable for use with the present system necessitate differently sized/shaped container holding yokes 82, and for this reason yoke 82 may be removably-mounted to filling station 5 by thumb-screws or the like, allowing replacement with different sizes and shapes. For example, FIG. 7C I shows a container holding yoke 82A with aperture configured to seat the protruding stem of an interface 214, 216, while FIG. 7C II shows a container holding yoke 82B with aperture sized to seat the neck of a container in which an interface 210, 212 has been inserted. The platform thickness of yoke 82 is also important as valved versus valveless closures may require differing degrees of syringe nozzle insertion and so some yokes 82 may need to be very thin. The operator can choose the appropriately-configured yoke 82, and in all such cases the yoke 82 facilitates easy frontal insertion of the container/syringe combination and stably supports the container.

Figure 7B:
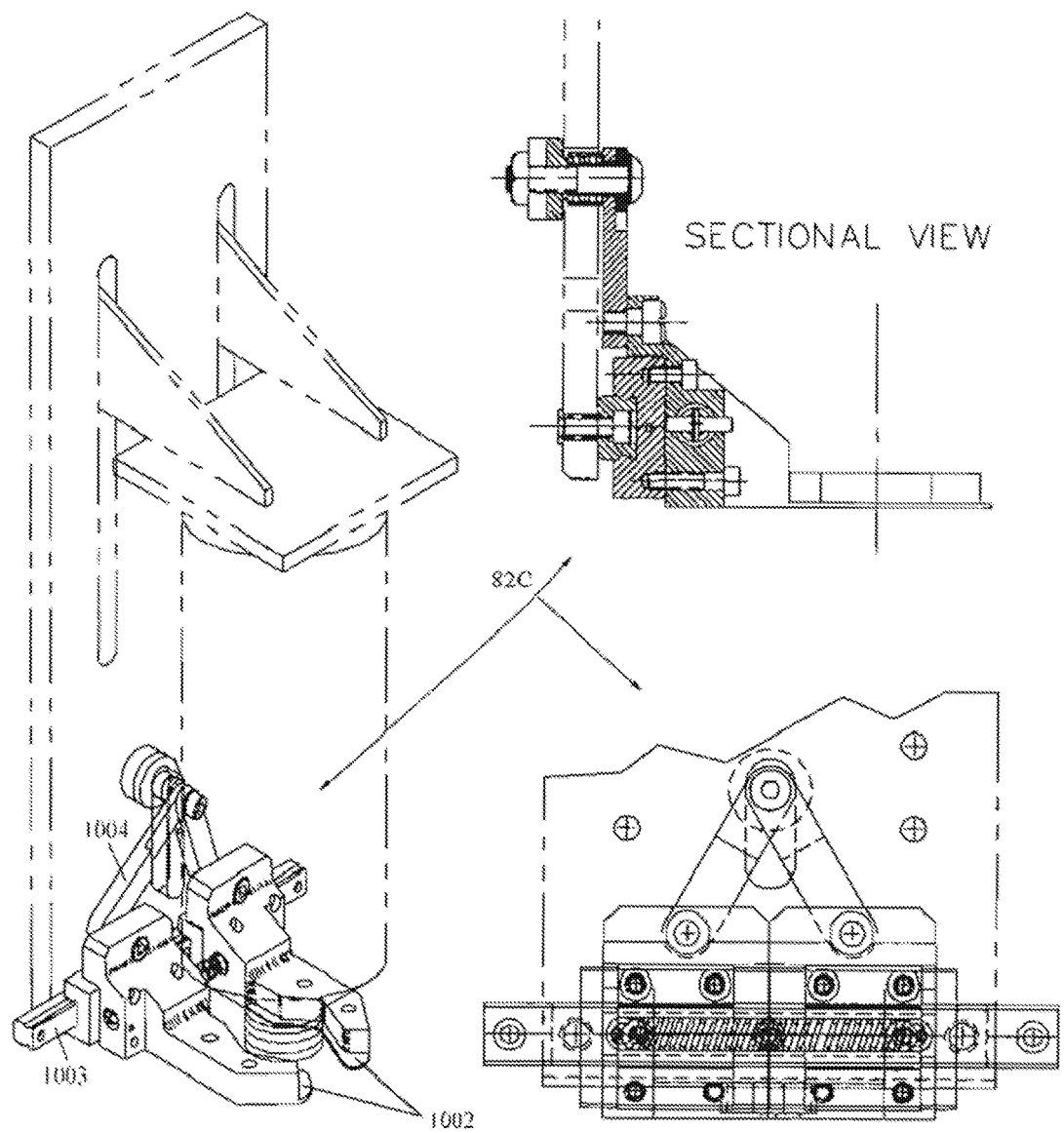
FIG. 7B is a composite view of a self-centering spring loaded bottle gripper assembly 82C used as an alternative to fixed yokes 82 of FIG. 7A.

FIG. 7B is a composite view of a self-centering spring loaded bottle gripper assembly 82C used as an alternative to fixed yokes 82 of FIG. 7A. The self-centering spring loaded bottle gripper assembly 82C of FIG. 7B employs a pair of spring-loaded jaws 1002 slidably mounted on a ball-slide track 1003 for slidable separation. A pair of trammel arms 1004 are coupled from each jaw 1002 to a common pivot and thereby maintain symmetry of the jaws 1002 as they separate. The operator rests the container neck onto the lips of jaws 1002 and pushes the container straight back, separating the spring-loaded jaws, until the jaws spring tight about the container and it is gripped. Note that the jaws 1002 are formed to hook around the container and have a lower-most flange to serve as a reference to ensure that all syringes are uniformly located in the vertical dimension. Thus, gripping assembly 82C is advantageously better able to withstand the shaking cycle and can fit into the limited space available.

The following table maps the container/syringe interface variations to requisite variations in the filling station 5 (FIG. 2 III 5) and points out the advantages of utilizing the self-sealing valve in the Baxa cap or PIBA for tapered tip syringes (as shown in FIG. 38) and/or the push-pull adapter cap 224 for Luer lock oral syringes (as shown in FIG. 39) according to one or more embodiments of the present invention:

| No. | Container/Syringe Interface | Filling station 5 container neck positioning device | Need to invert container and syringe 180° and then rotate 180° after filling syringe? | Able to shake at fill station? | Able to fill multiple syringes at one time without removing container from fill station? |
| --- | --- | --- | --- | --- | --- |
| 1 | valve-less press in bottle adapter (PIBA) | Yoke 82B (FIG. 7C II) | Yes | No | No |
| 2 | self sealing PIBA (SSPIBA) with an integral valve | Yoke 82B (FIG. 7C II) or self-centering jaws 82C (FIG. 7C III) | No | Yes | Yes |
| 3 | valveless Baxa ™ or Baxa equivalent | Yoke 82A (FIG. 7C I) | Yes | No | No |
| 4 | valved Baxa ™ or Baxa equivalent | Yoke 82A (FIG. 7C I) or self-centering jaws 82C (FIG. 7C III) | No | Yes | Yes |
| 5 | Valved self-sealing two-piece 220 | Yoke 82D (FIG. 7C IV) or self-centering jaws 82C (FIG. 7C III) | No | Yes | Yes |

-continued

| No. | Container/Syringe Interface | Filling station 5 container neck positioning device | Need to invert container and syringe 180° and then rotate 180° after filling syringe? | Able to shake at fill station? | Able to fill multiple syringes at one time without removing container from fill station? |
|---|---|---|---|---|---|
| 6 | Valved self-sealing one-piece 221 | Yoke 82D (FIG. 7C IV) or self-centering jaws 82C (FIG. 7C III) | No | Yes | Yes |
| 7 | Baxa™ or Baxa equivalent modified with non-integral push-in tip for Luer lock oral syringes | Yoke 82A (FIG. 7C I) | Yes | No | No |
| 8 | PIBA modified with non-integral push-in tip for Luer lock oral syringes | Yoke 82B (FIG. 7C II) | Yes | No | No |
| 9 | Baxa™ or Baxa equivalent modified with non-integral push-pull cap | Yoke 82A with grooved block 400 (FIG. 41) | No | Yes | Yes |
| 10 | Baxa™ or Baxa equivalent with integral push-pull cap | Yoke 82A with grooved block 400 (FIG. 41) | No | Yes | Yes |
| 11 | PIBA modified with non-integral push-pull cap | Yoke 82B with grooved block 400 (FIG. 41) | No | Yes | Yes |
| 12 | PIBA with integral push-pull cap | Yoke 82B with grooved block 400 (FIG. 41) | No | Yes | Yes |
| 13 | Valved common inner diameter cap with grooved rings | (Not shown) | No | Yes | Yes |
| 14 | PIBA retrofit with integral valve | Yoke 82B (FIG. 7C II) or self-centering jaws 82C (FIG. 7C III) | No | Yes | Yes |

With reference to FIGS. 7A and 7D, upper, middle, and lower syringe gripping arms 110, 111*i* and 112 are staged in a vertical orientation that will allow the selected syringe S to be easily slid into the fill zone, with plunger lifting arm 128 fully retracted. As different syringe sizes have different exterior dimensions, the vertical orientation of syringe gripping arms 110, 111 and 112 may be adjusted prior to syringe insertion to ensure that the syringe body can easily fit between the medication container and middle arm 111, which, as will be described, rests below the hilt or flange of the syringe. The syringe S is connected to the medication container and both are held by yoke 82. Once the medicine container and syringe S are in place, and the start button is pressed, a guard is closed around the filling station, or by some other signal from the processor, a pair of syringe finger grippers 78 close about the syringe S and hold it securely. Syringe finger grippers 78 are air operated for opening and closing, or may optionally be servo-driven, and have a servo-operated mount which moves the fingers to the center of the body of the syringe. This feature advantageously ensures that the syringe tip is exactly on center with the yoke, as syringe tip to body eccentricity varies on syringes sized from 10 mL to 60 mL. For syringe sizes between 0 mL and 60 mL, the tip of the syringe is eccentric to the body diameter, whereas on syringe sizes from 0.5 mL to 5 mL, the tip is concentric on the body diameter. The in and out motion of the servo mount locates the grippers 78 to grip the center of the syringe body so that the center of the tip is always on center with the yoke, regardless of its eccentricity to the body of the syringe. Additionally, a bottle holder platform 79 lowers to sandwich the medicine container against the container holding yoke 82. The bottle holder platform 79 has an aperture 791 through it and a scanner 121 is mounted above the aperture 791 to read the machine readable label on the bottom of the container 104.

An articulating syringe locator guide 81 (FIG. 7A) comprises a pair of offset fingers on a bracket that push against syringe finger flanges, effectively rotating the syringe to a known orientation. This ensures that all offset-tip syringes (nozzle offset from center axis) are in proper orientation for filling. One skilled in the art should understand that the syringe locator collar 81 is not required for concentric tipped syringes and may be articulated out of the way.

Once in the fill position in loading station 70 with syringe finger grippers 78 closed around it, the syringe S is engaged by the upper 110, middle 111 and lower 112 arms, and a plunger lifting arm 128 that extends upward from below, all of which collectively grip and operate the syringe S in order to effectuate the filling process as described below.

The syringe locator guide 81 withdraws to its home position. Upper arm 110 lowers and middle arm 111 raises to close on the syringe body hilt or flange (see FIG. 19 for detailed view). This creates a sandwiching effect to hold the body of syringe S securely. Lower arm 112 then moves downward onto the upper side of the syringe plunger disc and plunger lifting arm 128 rises to a position just under the syringe plunger, thus working in concert with lower arm 112 to create a sandwiching effect on the syringe plunger disc captured between them. Upon command from the operator or programmer, arm 112 and arm 128 work in concert to perform priming and/or filling of the syringe S. The use of both arm 112 and arm 128 allow the filling station to exert both a pushing and a pulling effect on the syringe plunger as the program dictates, thus allowing better control of the plunger location during both priming and filling. Upper and middle arms 110 and 111 may also work in concert to push syringe S further upward towards the medication container as necessary to ensure that the closure of the medication container hasn't relaxed its fit with the tip of syringe S. The priming sequence is determined by syringe size and viscosity of medicine to be filled. After priming is complete and with the piston all the way up, the piston is then pulled downward to fill with the correct dose.

As described in more detail below, in a preferred embodiment, arms 110, 111, 112 (FIG. 26) protrude vertically from the horizontal base of the filling station 5 (FIG. 2), at which point they are sealed with waterproof bushings, and terminate with at least one horizontally-oriented curvilinear jaw. The watertight seal between the vertically oriented syringe filling arms 110, 111, 112 and the horizontal base of the filling station 5 advantageously prevents liquids (such as medication from medication container 4) from being able to inter the interior of filling station 5. This curvilinear embodiment is thus preferred over the herein described horizontal arms having straight fingers wherein the horizontal arms 110, 111 and 112 must articulate vertically through one or more open vertical slots in the vertical back of filling station 5 (see FIG. 7A). The watertight seal and vertical orientation of curvilinear arms 110, 111, 112 is accomplished via the horizontally-oriented curvilinear jaw, which is able to grip various portions of the syringe S through a rotational motion of syringe gripping arms 110, 111, 112 and withdraw the plunger of the syringe S with vertical motion of syringe gripping arms 10, 111, 112.

As stated in the foregoing Table the yoke 82 will vary depending on the syringe interface variation. Specifically, the OEM/Baxa cap 214 will require yoke 82A (FIG. 7C I), the OEM/Baxa cap with self-sealing valve 216 will require Yoke 82A (FIG. 7C I), the valveless PIBA 210 will require yoke 82B (FIG. 7C II), the PIBA with self sealing valve 212 will require the adjustable clamping device 82C (FIG. 7C III), the Luer-type syringe adapter tip 223 will require the adjustable clamping device 82C (FIG. 7C III) or yoke 82A (FIG. 7C I), push-pull cap 224 and the threaded cap with automation grooves and valve will both require the adjustable clamping device 82C (FIG. 7C III).

The invention relies on a conventional network architecture which includes a local OSPS (Oral Syringe Packaging System) computer. The OSPS computer is interfaced to a hospital host computer and receives oral syringe prescription instructions therefrom (however, the OSPS system may be used as a stand-alone unit independent of any interface with another computer). In the majority of circumstances, physicians submit prescriptions for oral syringes electronically to the hospital host computer and these prescriptions are communicated to the OSPS computer for fulfillment. The interface serves to parse/extract those oral medication prescriptions from all prescriptions submitted.

The local OSPS computer is programmed to know what must occur at each station and monitors to ensure that each step of the process is completed satisfactorily and that all decision rules are complied with. The local OSPS computer software implements a Medication Container Orientation and Log-In Process for semi-automated preparation and storage of bulk medicine containers to be used in filling and packaging oral syringes, and a Batch Fulfillment Process for semi-automated filling and packaging of oral syringes using the stored bulk medicine containers. In general terms, the semi-automated Medication Container Orientation and Log-In Process comprises the following steps:

a. Pharmacy technician (operator) removes the manufacturer's cap from the bulk medicine container received from the pharmaceutical manufacturer and installs one of several possible container/syringe interface variations (as described above and below), in all such cases facilitating insertion of an oral syringe nozzle into the container. The present system is adaptable to filling syringes with each interface variation. The system may include an optional motorized capper/decapper station to assist with the removal of the manufacturer's cap and the application of a threaded or PIBA interface.

b. Variable information such as container fill size, manufacturer's expiration date, and product lot number are entered into the OSPS computer automatically as much as possible by bar code scan, or manually by the Pharmacy Technician under the supervision of the Pharmacist. First, the software guides the operator to scan the manufacturer's barcode label. However, the barcoded information is often incomplete. Any missing variable information such as container fill size, manufacturer's expiration date, and product lot number can be derived and manually entered into the OSPS computer by the Pharmacy Technician.

c. If needed, the OSPS computer instructs the Pharmacy Technician which of the container/syringe interfaces to select for recapping the medication container. The OSPS obtains this information from the medication database. In addition, the OSPS may direct the storage location of the correct size container/syringe interface to illuminate, unlock, or the like, as described in further detail below.

d. The OSPS computer auto-assigns an expiration date to the medication container based on either the manufacturer's expiration date or the expiration date defined by pharmacy policy. The pharmacy expiration date policy is determined by the date the container is opened at the medication container log in station plus the number of days the Pharmacist determines that the medication should expire. The OSPS computer uses the date that is the soonest to determine the effective medication container expiration date.

e. Software automatically prints a new unique 2D barcode label.

f. The 2D barcode label is placed on the center of the base of the container.

g. Software guides the operator to rescan the manufacturer's barcode on the container label and the 2D barcode on the base of the container.

h. If scanning checks, the software guides the operator to place the medication container in a particular (logged) storage facility location.

The semi-automated Batch Fulfillment Process for any of the self-sealing caps described herein comprises the following steps:

a. The software guides the operator to retrieve the medication container from a particular (logged) storage facility location (the medication container may previously be logged according to the method described herein with respect to the Medication Container Orientation and Login Station).

b. The operator loads the medication container into the fill station.

c. The 2D barcode on the medicine container bottom is scanned to make sure that all medication issues relating to that medicine container have been addressed, including correct medication, refrigeration, expiration and light-sensitive storage.

d. The software guides the operator to pick a syringe of the proper color and size.

e. The operator places the syringe in a syringe size/color station that verifies that the proper size and color syringe has been selected.

f. If the syringe size/color inspection passes, the software automatically prints a label for the syringe, and the operator manually applies the label to the syringe. Alternatively, a semiautomatic flag labeler may be used, as described in more detail below.

g. The label is rescanned to ensure that the information is readable and correct.

h. The operator scans the 2D barcode on the syringe at the filling station.

i. If needed, the medication container is shaken for the duration, intensity and interval(s) required by the shaking mechanism to which the container is attached.

j. The operator positions the syringe at the filling station.

k. The system/software automatically fills the syringe from medicine in medication container as described in more detail above and below.

l. The operator caps filled syringe at optional semi-automatic capper.

m. The operator scans the syringe at the optional fill inspection station.

n. The system automatically inspects the syringe at an optional visual inspection station for proper weight and/or volume.

o. The operator scans the syringe at the bagging station.

p. The system/software automatically prints bag that the syringe will be packaged in.

q. The software automatically scans the printing on the bag to make sure that it is correct.

r. The operator places the syringe in the bag at the bagging station, and the system confirms that the syringe was placed in the bag and seals the bag with the syringe in it.

All medication containers and medicines in those containers that have been logged in, each size syringe, each size container/syringe interface, the syringe labels, syringe bags, print media, etc. are automatically inventoried. As an item is used or consumed, an accounting of the amount of that item remaining is maintained.

Via the 2D barcodes on each syringe and medication container and the scanning operations at each station, Track, Trace and Validation software monitors and documents the entire process from the prescription approval by the pharmacist, log-in of the medication container through each step of the packaging process to ensure that the syringe is filled and packaged correctly. The Track, Trace and Validation software also tracks the operation of the equipment used in the process to ensure that each piece of equipment is functioning properly, and provides error messages when any piece of equipment malfunctions. This aspect of the invention further results in the formation of an "audit" record of all machinery involved in the processes so that an operator, pharmacist, or technician may review a log of the machinery's operations to perform troubleshooting and/or quality checks.

FIG. 1 is a high level flow chart of the overall method of the invention. The following method steps are performed semi-automatically with some manual intervention by or interaction with an operator for filling patient-specific oral syringes on a just-in-time basis. Note that "semi-automatic" necessarily entails manual intervention/interaction which has a propensity for introducing mistakes. The present method and apparatus is specifically designed to avoid mistakes and maintains comprehensive track-and-trace validation of each manual step:

At step 705 a physician writes an oral medicine prescription which is electronically entered into existing hospital host computer (as all prescriptions are so logged).

At step 710 the existing hospital host computer communicates the oral medicine prescription to the hospital pharmacy for approval. A pharmacist will typically review it.

If approved by the pharmacist, then at step 715 the prescription is transmitted the local computer of the OSPS (Oral Syringe Packaging System) of the present invention. The oral syringe prescription is added to a batch fulfillment queue at the local OSPS computer. As described below the queue is multi-sorted so that all prescriptions for a particular type of medicine (e.g., Acetaminophen, cough syrup, etc.) can be fulfilled together, and at periods throughout the day an operator may run a batch fulfillment queue (typically batches are run a few times each day).

At commencement of batch fulfillment, the OSPS system preferably guides the operator in retrieving the appropriate medication container from OSPS storage (as will be described). Such guidance presupposes that a library of medicine containers is maintained and that each such medicine container be logged into the OSPS system so that its location and contents are known to the local OSPS computer. Consequently, as a precursor to batch fulfillment each new medication container is logged into OSPS storage by a barcode, RFID scan or similar identification scan (e.g., of the manufacturer's barcode) as described above. The manufacturer-supplied medicine container cap must be replaced, retrofit, or supplied by the manufacturer in a form that enables an oral syringe to enter a center hole and withdraw an amount of liquid from the medication container while the medication container is positioned upside down, and the syringe S then removed from the container without leaking. There are fourteen container/syringe interface variations suitable for use with the present system (see FIGS. 5, 27-34 and 44 and the detailed descriptions associated with them). All this occurs at step 720 (FIG. 1).

At step 725, based on the medication container login, the OSPS system guides the operator in properly storing the new medication container. The OSPS system (as described below) includes separate storage locations for three types of medication containers: Location 1—No Special Handling of container; Location 2—Refrigeration Required; Location 3—Light Sensitive medication container (refer to FIG. 2 II, refs a-c). Each storage compartment within each location may be enclosed by a magnetically-actuable door so that access to each location may be electronically controlled by the local OSPS computer. Alternately, each storage compartment within each location may be illuminated by an LED light, so that access to the proper location may be electronically guided by illumination of the proper LED. As another alternative, each storage compartment within each location may be equipped with a light curtain so that the local OSPS computer can monitor access to the proper location. All these and other suitable forms of user-guidance/ selection are considered to be within the scope and spirit of the present invention. In all such cases, the end result is an OSPS storage library of different oral medicines in their bulk containers, each properly logged in and stored in its corresponding storage location a-c.

Similarly, at step 740 an inventory of packaging materials is maintained, including empty syringes in an array of sizes, syringe caps, labels (for barcodes), and ink foil printer ribbon.

In support of the OSPS system, at step 730 a comprehensive medication database is maintained at the OSPS computer. The OSPS medication database includes the following:

1. Medication Information:
   a. Medication name.
   b. Manufacturers barcode number.
   c. Written information that corresponds to manufacturer's barcode number.
   d. Whether medication needs to be shaken, if so, the frequency, intensity, and duration.
   e. Whether the medication needs to be refrigerated, if so refrigeration policy required.
   f. Whether the medication is light sensitive, if so light sensitive protection required.
2. Product information (pertaining to individualized medication containers logged in):
   a. The OSPS 2D barcode number assigned to that specific container. The label containing this information is placed on the base of the container.
   b. Fill size of that container in cubic centimeters (cc) or milliliters (ml).
   c. Current amount of product remaining in that container after deducting for previous fills extracted by the syringes.
   d. Manufacturer's Expiration Date.
   e. Date the medication container is logged-in at the Medication Container Log-In Orientation System.
   f. Pharmacy Policy Expiration Date. This is the container open date plus number of days before container expires (determined by pharmacist).
   g. Effective Expiration Date. This is the soonest of the manufacturer's expiration date or the date that the container is open plus the number of days that the open container will expire (i.e., Pharmacy Policy Expiration Date).

Given all of the foregoing, at step 750 an operator may at any convenient time commence the batch fulfillment process. The detailed substeps of the batch fulfillment process 750 are described below and illustrated in the block diagram of FIG. 3.

Referring back to FIG. 1, after each oral syringe has been filled and packaged during batch fulfillment 750, it is inspected and either rejected at step 760 or approved at step 770.

The above-described method is herein implemented in several detailed embodiments of a system suitable for preparing patient-specific oral syringe doses. Various alternate embodiments of the invention may omit selected steps (and their performance station) where such is/are not required. The needs of the operating institution and the cost aspect of automating certain steps may direct which steps/stations (if any) are to be performed manually by an operator interfacing with the apparatus and which may be automated.

A presently-preferred embodiment of the physical system componentry is described below with reference to FIG. 2.

Figure 2:
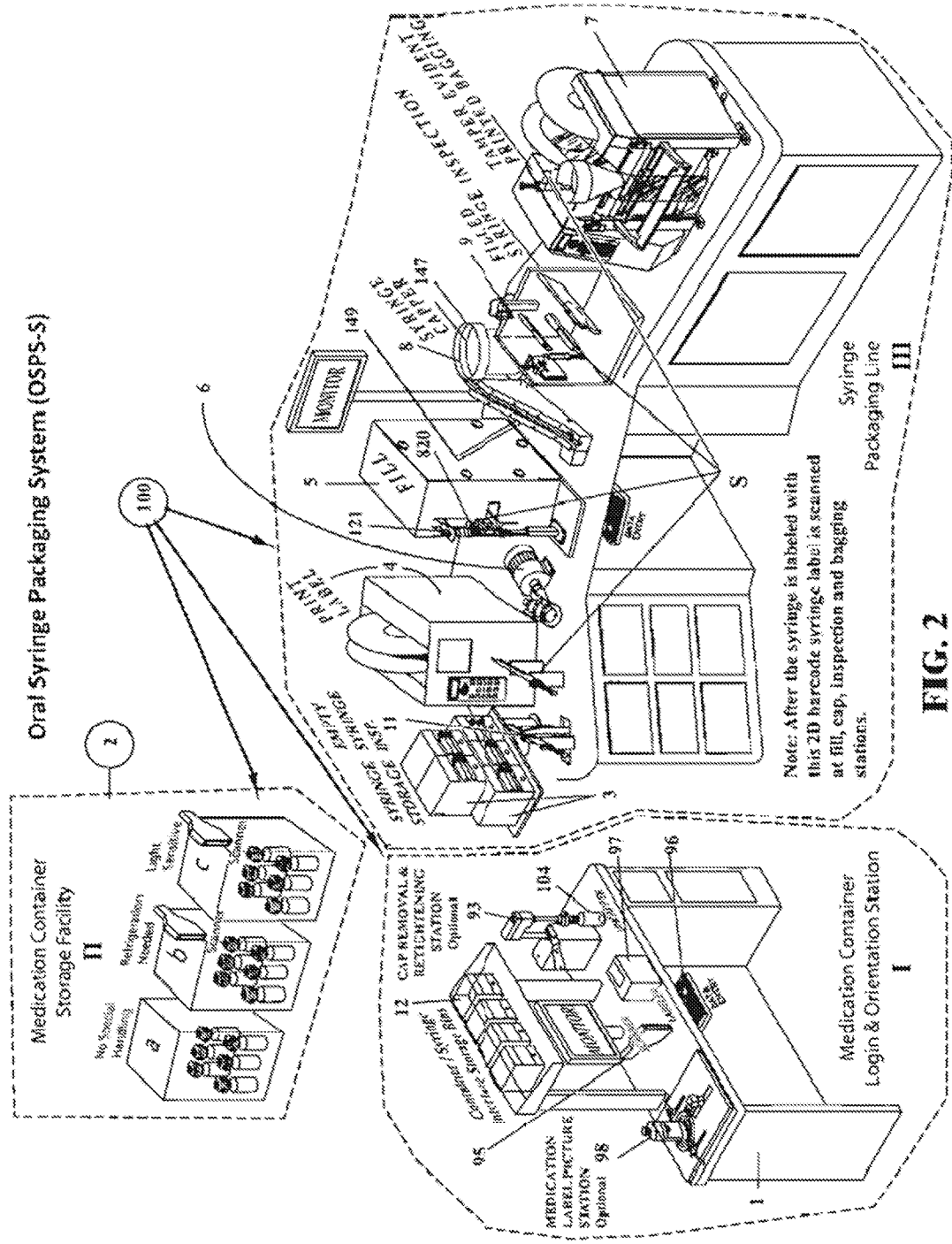
FIG. 2 is a perspective view of the entire pharmacy automation system 100 according to an embodiment of the invention.

As seen in FIG. 2, the pharmacy automation system 100 for packaging oral syringes generally comprises a standalone Medication Container Login & Orientation Station 11, with an included array of container/syringe interface storage bins 12. In addition, a proximate or remote Storage Facility II is provided for storing all logged in medication containers, with separate locations for the three types of medication containers: (a) Location 1—No Special Handling of container; (b) Location 2—Refrigeration Required; (c) Location 3—Light Sensitive medication container. The final component of the system includes the syringe packaging line III.

In an alternate embodiment of the present invention, Storage Facility II of FIG. 2 may be substituted with an automated medication storage cabinet (AMSC) with rotary shelves, such as the commercially available MedCarousel® sold by McKesson Automation Solutions, or similar models sold by TALYST, OMNICELL, SAPIENT AND US MEZZANINES, AMSC units such as these are currently being utilized in hospital pharmacies. These systems automate the medication management process from ordering the medication, stocking the medication on the system's rotating shelves, and presenting the medication to the pharmacy technician at the time the medication needs to be utilized to fill the prescription on the OSPS. Therefore, the accuracy and efficiency of medication dispensing and inventory management is increased. Aided by rotating shelves, pick to-light, bar code scanning and comprehensive integrated workflow software, the AMSC systems guide the pharmacist to medication storage locations, improving picking speed and accuracy. AMSC systems such as the MedCarousel® can handle storage of refrigerated as well as non-refrigerated medicines.

In conjunction with the OSPS, an AMSC system would operate as follows:
1. Two AMSC systems would be utilized, one for non-refrigerated medications and the other for refrigerated medications. The containers that require light protection would be stored on the non-refrigerated AMSC system.
2. After the medication container was oriented and logged in to the OSPS, the AMSC would assign a location to store that medication.
3. The 2D bar code on the container would be scanned.
4. The shelf that the medication was to be stored on would be positioned in front of the pharmacy technician. A light would appear over the location on the shelf on which the medication was to be stored.
5. The pharmacy technician would place the medication at that location.
6. At the start of the next OSPS production run, the OSPS would list the prescriptions to be filled by medication. This information would be sent to the AMSC(s).
7. The pharmacy technician would then remove the medication containers that are presented and scan them. The medication containers would be kept in the same order in which they are removed by the technician. This order corresponds to the order in which the medication will be used to fill syringes on the OSPS.
8. After the production run, the medication containers would be returned to the AMSC(s) in the same order in which they were removed therefrom. The pharmacy technician would scan the medication containers. The AMSC(s) would present the pharmacy technician with the proper shelf and light the position to which the medication container should be returned. The pharmacy technician would return the medication container to the indicated location in the AMSC(s).

A syringe storage bin 3 (see FIG. 2 III) is provided for storage of empty syringes, and a syringe label printer and labeler station 4 (see FIG. 2 III) is also provided. Next, a syringe size/color inspection station 11 is provided. These are followed by a syringe filling station 5 with integrated medication container shaker assembly 820 (as described below). An alternative embodiment is a stand-alone shaking station.

At the filling station 5 the medication container with container/syringe interface 212 or 216 (see FIG. 5) is manually inverted and inserted. An overhead clamp lowers against the topside base of the medicine container to clamp the container against its holder. This provides an opportunity to inspect the medication container's 2D barcode (located in the center of the container's bottom) via the Lexan™ disc found in platform 79 (see FIG. 7A) to verify that it is the correct medication. The medication container is shaken if necessary. The syringe's 2D barcode is inspected and, if correct, the syringe is inserted into the medication container via the container/syringe interface. A plurality of servo-driven fingers (to be described) grip and stabilize the syringe S. The fingers manipulate the syringe plunger to prime and fill the syringe. When all syringes have been filled with the medication, the medication container is returned to storage. This process continues until all syringes for that prescription production run have been filled.

Next, a semi-automated capping station 8 is used to place a cap (fed from an inclined capping chute 149) on the open tip of the filled syringe.

After each syringe S is filled and capped it is loaded into a vision inspection station 9 which verifies the presence of the cap, the piston position within the syringe, that the syringe is filled with medication, and that an excessive number of air bubbles are not present.

Lastly a bag printing and sealing station 7 bags the filled syringe in a barcoded bag.

The purpose and function of each of the foregoing stations 1-5, 7-9, and 11 (see FIG. 2 I, II, III) will become clearer in the context of a detailed description of the Medication Container Orientation and Log-In Process (step 720), and Batch Fulfillment Process (step 750).

Medication Container Orientation and Log-in Process (step 720)

The OSPS system guides the operator in properly equipping and storing each bulk medication container. As described above, the manufacturer-supplied medicine container cap must be replaced, retrofit, or supplied by the manufacturer in a form that enables an oral syringe to enter a center hole and withdraw an amount of liquid from the medication container while the medication container is positioned upside down, and the syringe S then removed from the container without leaking. Thus, at step 720 (FIG. 1) the manufacturer-supplied medicine container cap may need to be provided to specification, or replaced or retrofitted with a container/syringe interface to provide a penetrable orifice. As described more fully below the retrofit may be accomplished in a number of ways. Thus, the present invention contemplates fourteen (14) container/syringe interface variations: (1) a valve-less press in bottle adapter (PIBA) 210; (2) a self sealing PIBA (SSPIBA) 212 with an integral valve (typically, either a linear or a Z-shaped slit) 213; (3) a standard manufacturer-supplied (Baxa™ or Baxa equivalent) valve-less medicine container cap 214 with opening; (4) a modified manufacturer-supplied (Baxa™ or Baxa equivalent) medicine container cap 216 that is retrofit to include an integral valve 225 (typically, a duckbill valve); (5) a two-piece cap comprising an outer portion 220 with a common outer diameter for all standard sizes of medication container, and a self-sealing insert 212; (6) a cap 221 comprising a common outer diameter for all standard sizes of medication container and having an integral self-sealing insert 212; (7) a modified manufacturer-supplied (Baxa™ or Baxa equivalent) medicine container cap 214 that is retrofit to include a non-integral push-in tip 223 for interfacing with Luer lock oral syringes; (8) a modified PIBA 210 that is retrofit to include a non-integral push-in tip 223 for interfacing with Luer lock oral syringes; (9) a modified manufacturer-supplied (Baxa™ or Baxa equivalent) medicine container cap 214 that is fitted with a push-pull cap 224 for interfacing with Luer lock oral syringes; (10) a modified manufacturer-supplied (Baxa™ or Baxa equivalent) medicine container cap 214 that is retrofit with an integral push-pull cap 224 for interfacing with Luer lock oral syringes; (11) a modified PIBA 210 that is fitted with a push-pull cap 224 for interfacing with Luer lock oral syringes; (12) a modified PIBA 210 that is retrofit with an integral push-pull cap 224 for interfacing with Luer lock oral syringes; (13) a cap 226 comprising a common inner diameter for all standard sizes of medication container, fitted with an integral or separable valve 225 (typically, a duckbill valve), and having grooved rings to facilitate handling, positioning, etc. by the system according to the present invention; and/or (14) a valveless PIBA that is retrofit to include an integral valve 225 (typically, a duckbill valve). Again, all fourteen variations as shown in FIGS. 5, 27-32 and 34 and 44 are described below in detail above.

It is envisioned that medication containers may be provided to the hospital pharmacy for use with the present system in such a way that will minimize or possibly eliminate any need for the Medication Container Orientation and Log-In Process (step 720). For example, medication containers may be provided for use with one or more of the following features:

1) standardized caps with self-sealing valve (such as, for example, the above-referenced Baxa™ or Baxa-equivalent medicine container cap with penetrable opening);
2) standardized containers;
3) barcoded or RFID-coded containers that already contain the information that a pharmacy technician would otherwise need to input during the Medication Container Orientation and Log-In Process (step 720); and/or
4) any other means of providing the information that a pharmacy technician would otherwise need to input during the Medication Container Orientation and Log-In Process to the OSPS database and system, such as, i.e., via the Internet.

A combination of all three features listed above would minimize or eliminate the need for the Medication Container Orientation and Log-In Process (step 720). However, for purposes of complete description it will be assumed that such features are lacking in OEM-supplied medication containers and so the Medication Container Orientation and Log-In Process (step 720) will herein be described in detail.

Figure 4:
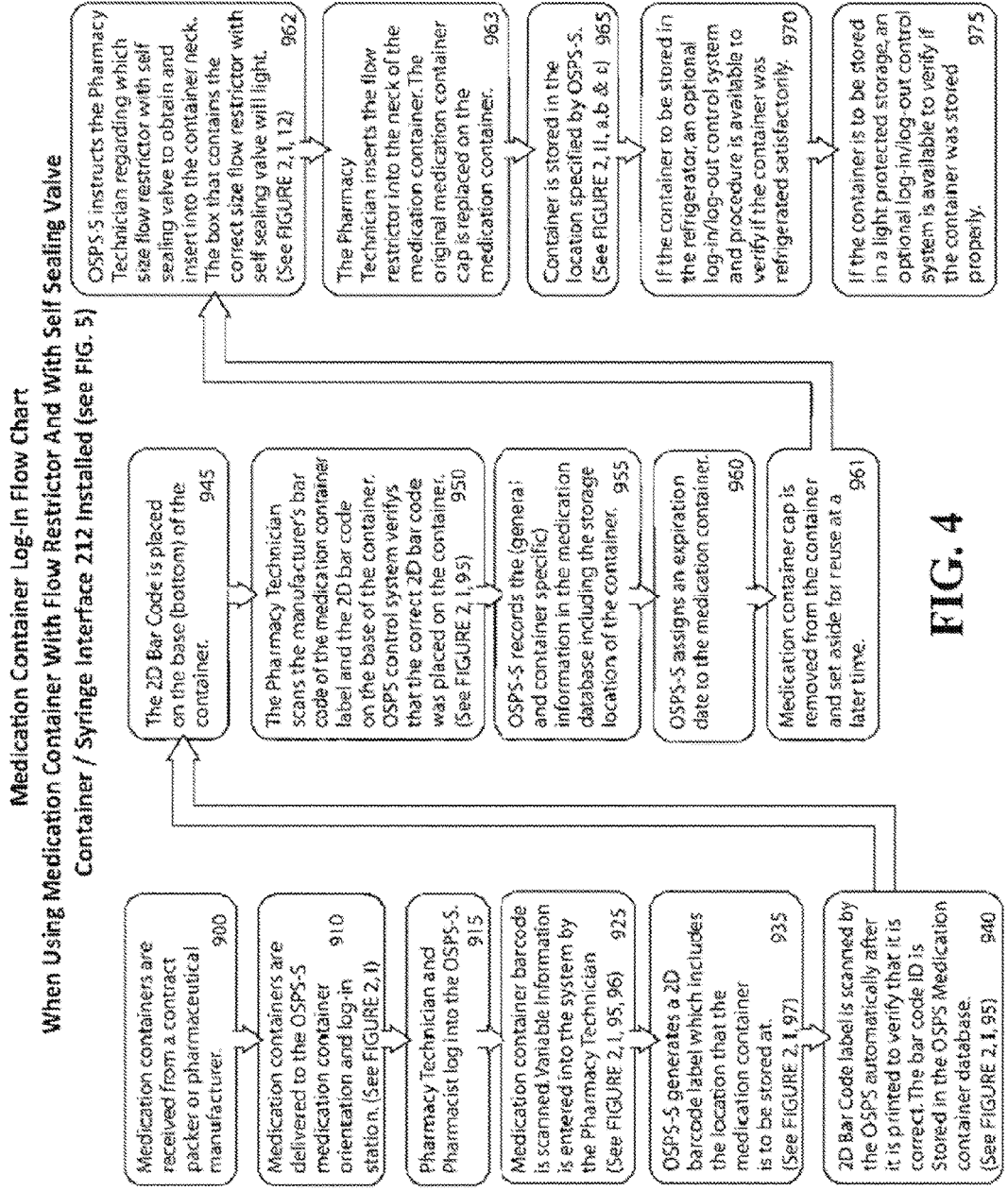
FIG. 4 is a more detailed block diagram of the medication container orientation and log-in process 720 of FIG. 1.

Referring now to FIG. 4 which is a flow diagram of the Log-In process for the valved PIBA 212 (see FIG. 5), at step 900, medication containers are received from a contract packager or pharmaceutical manufacturer.

At step 910, medication containers are delivered to the OSPS Medication Container Login & Orientation Station 1 (FIG. 2).

At step 915 the pharmacist and operator logs into the local OSPS computer.

At step 925 the manufacturer-provided medication container barcode is scanned. Variable information is entered into the system by the pharmacy technician.

At step 935, the labeler shown at the Medication Container Login & Orientation Station 1 (see FIG. 2 I) generates a 2D barcode label which includes the location that the medication container is to be stored at. The 2D bar code is manually placed on the bottom of the container (or on the container/syringe interface) at step 945.

At step 940, the bar code label is automatically scanned/inspected immediately after printing to verify that its contents are correct and the bar code ID is stored in the OSPS database.

At step 945, the bar code label is adhered to the base (bottom) of the container.

At step 950, both the 2D bar code placed on the base of the container and the pharmaceutical manufacturer's barcode are scanned using a scanner resident at the Medication Container Login & Orientation Station 1 and the manufacturer's bar code on the medication container label are scanned to verify that the correct 2D bar code was placed on the base of the container.

At step 955 all general and container specific information, inclusive of Product Information and label photograph, is recorded in the local OSPS computer database, including the storage location of the bulk container.

At step 960, the OSPS local computer assigns an expiration date to the medication container. The expiration date is predetermined by pharmacy policy. The pharmacy policy expiration date is determined by the date the container is opened at the Medication Container Log In Station 1 plus some number of days after which the Pharmacist determines that the medication should expire.

At step 961, the medication container cap is removed from the container by the operator and is set aside for later reuse.

At step 962, the OSPS local computer instructs the pharmacy technician regarding which size adapter cap to obtain and insert into the container neck. To guide the operator, the box 12 containing the correct size adapter cap is preferably illuminated as shown in FIG. 2.

At step 963, the pharmacy technician inserts the adapter cap onto the medication container. In some embodiments, the original medication container cap from step 961 may be replaced on the medication container.

At step 965, the operator manually stores the medication container in the location specified by the OSPS local computer (see FIG. 2 II).

At step 970 if the container is to be stored in the refrigerator, an optional log-in/log-out control system and procedure is available to verify if the container was refrigerated satisfactorily (see FIG. 2 II b). This way, if the container is outside of the refrigerated storage area more than a specific number of minutes the OSPS local computer will not permit the syringe to be filled from that container, and will alert the Pharmacy Technician to remove and discard that container.

At step 975 if the container is to be stored in a light protected storage area, an optional log-in/log-out control system and procedure is available to verify if the container was stored appropriately (see FIG. 2 II c). This way, if the container is outside of the light protected storage area more than a specific number of minutes the OSPS local computer will not permit the syringe to be filled from that container, and will alert the Pharmacy Technician to remove and discard that container.

Figure 3:
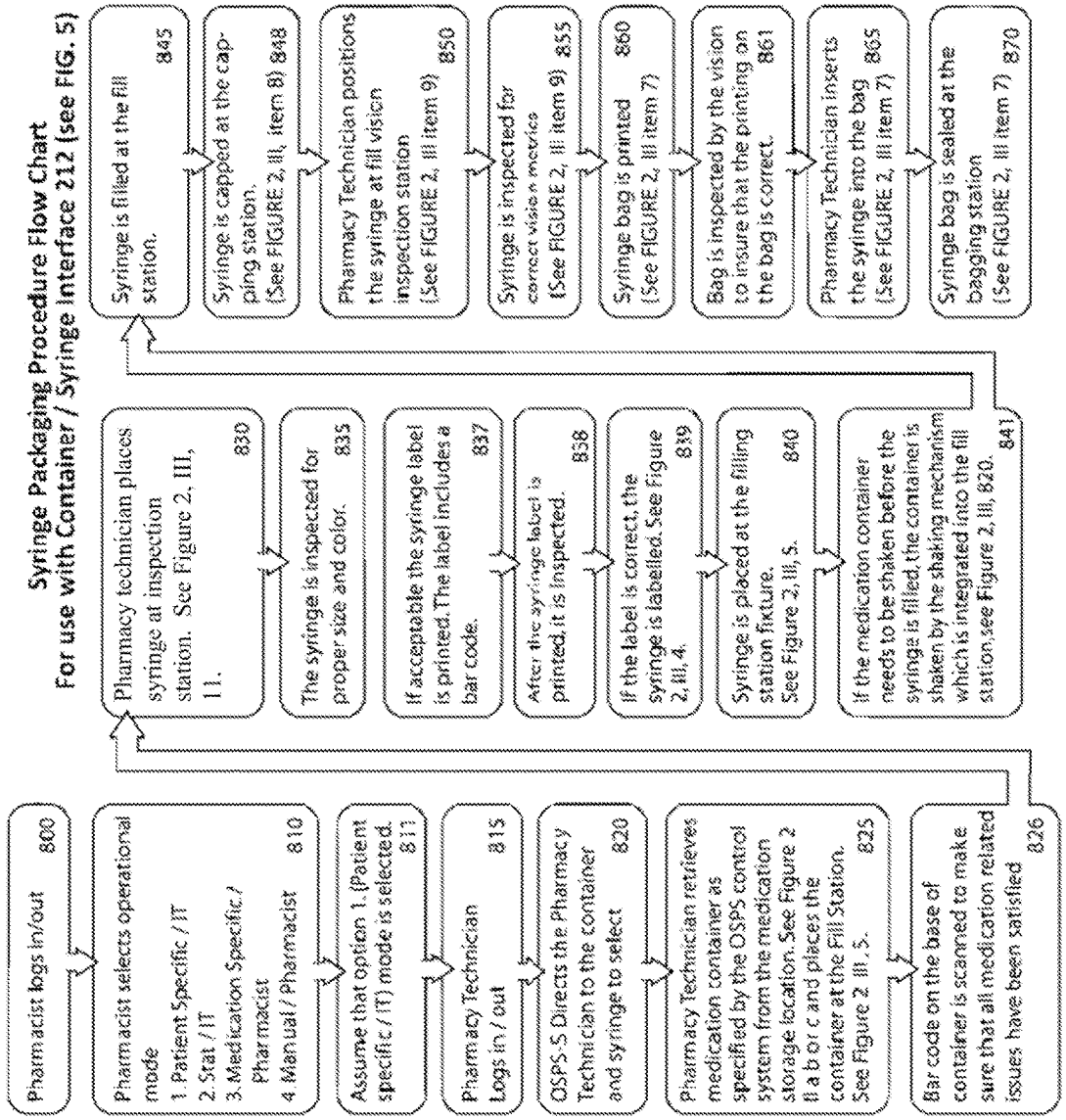
FIG. 3 is a more detailed flowchart of the substeps of the batch fulfillment process 750 of FIG. 1.

Batch Fulfillment Process 750 (FIGS. 1-3)

With reference both to FIGS. 2-3, at step 800 a pharmacist must log into the OSPS local computer to use the system.

At step 810, the pharmacist selects the desired OSPS operational mode. Currently four modes of operation are envisioned:

1. Patient Specific—Hospital Directed
   a. The Doctor writes the prescription and enters it into the Hospital Host Computer System.
   b. The prescription is reviewed by the Pharmacist. If it is okay, the prescription is sent to the Local OSPS Computer where it is batched. Batches will typically be run 2-3 times a day.
   c. The Local OSPS Computer first sorts all the batched prescriptions by type of medication. The order of the queue may be in the discretion of the pharmacist (i.e., alphabetically by medication name).
   d. The prescriptions are then sorted by size of fill from smallest to largest. The total amount of each medication required for that batch run is totaled. The Local OSPS Computer checks to ensure that there is a sufficient amount of product for each medication required to complete the batch.
   e. If a doctor orders, for a single patient, multiple same doses of the same medication to be administered at different times, all doses can be filled together during a single production run or in separate production runs at the discretion of the Pharmacist. In a preferred embodiment, all prescriptions for one medication are filled at the same time, followed by all prescriptions for the next medication, etc.

2. STAT (Rush Order)—Hospital Directed
   a. The Doctor writes the prescription and enters it into the Hospital Host Computer System.
   b. The prescription is reviewed by the Pharmacist.
   c. The prescription order indicates that the prescription needs to be administered soon to the patient.
   d. If the OSPS System 100 is currently being used, the Pharmacist can decide to either stop all current prescriptions being packaged or wait until completion. Either way, the Local OSPS Computer processes the singular rush order.

3. Medication Specific—Pharmacy Directed
   a. This mode allows production-scale filling of a large number of syringes with the same medicine and the same fill volume. Some medication will need to be inventoried in advance of the Doctor's prescription. This mode provides the pharmacist with the opportunity to package certain liquid oral products such as vitamins and popular standard dose medications on a more cost-effective basis than buying them already pre-packaged,
   b. The Pharmacist will manually enter in a production order for the medication into the Local OSPS Computer.
   c. The Pharmacist will specify the medication name, size of fill, the information that will go onto the syringe label, the information that will go onto the bag that the syringe is packaged in, and the amount of syringes that are to be packaged for that production run.

4. Manual—Pharmacy Directed
   a. Not all hospitals have an existing electronic prescription system installed that permits the electronic transmission of the Doctor's prescription to the hospital pharmacy. Consequently, the OSPS can be operated on a manual basis whereby the prescriptions are entered into the system under the Pharmacist's supervision.

One skilled in the art should understand that other operational modes are possible, for example, a Patient Priority mode in which all medications/oral prescriptions for a specific patient are processed sequentially before moving on to the next patient. The invention is herein described in the context of Patient Specific—Hospital Directed Mode which is the most typical mode of operation.

At step 811, by way of example, Patient Specific—Hospital Directed is selected and the process is herein described accordingly.

At step 815 an operator (pharmacy technician) logs in.

At step 820 the OSPS local computer directs the operator to select the appropriate medicine container from Storage Facility 2 (see FIG. 2 II), and an appropriate syringe from storage bin 3 (FIG. 2 III).

At step 825, the operator retrieves the appropriate medicine container from Storage Facility 2 (see FIG. 2 II) (under system guidance) and inverts and installs it at the syringe filling station 5 (see FIG. 2 III).

At step 826, the barcode on the bottom of the container is scanned to make sure that all medication-related issues have been satisfied (refrigeration, shaking, light-sensitive storage, expiration, etc.).

At step 830, the pharmacy technician places the syringe S on the inspection station cradle (see FIG. 2, ref. 11). Alternatively, the inspection station may be omitted and the syringe may be inspected at the labeling station 4.

At step 835, the system automatically inspects the syringe for proper size based on a syringe body measurement (described below), to verify that the correct syringe has been selected. Proper color of color-coded syringes is also verified.

At step 837, the operator prints a syringe label at syringe label printer and labeler station 4 indicating in both human and machine readable forms (i.e. text, barcode or RFID tag) the type, concentration, expiration, etc. of the medication it will contain. The label includes a bar code (preferably a 2D barcode though other labels such as RFID may be used. The label is adhered to the syringe barrel. Alternatively, a semi-automatic flag labeler is used as described below.

After printing the label per step 837, at step 838 the label is inspected to ensure that its content is correct.

At step 839, the label is affixed to the syringe S (where a semi-automatic flag labeler is used, the flag is adhered to the syringe S automatically by the labeler).

At step 840, the operator manually places the syringe at the syringe filling station 5 (FIG. 2).

At step 841 (if required), the shaking mechanism 820 (FIG. 2 III) shakes the medication container before any medication is drawn from it into the syringe.

At step 845, the syringe is filled at the filling station 5. The OSPS system automatically primes and fills the syringe with the medicine by insertion and withdrawal of the plunger.

At step 848, the syringe is capped at the semi-automatic capping station 8. The capping station caps the syringe and presents it to the operator.

At step 850, the operator positions the filled syringe S at the vision inspection station 9 (FIG. 2, III) and at step 855 the syringe is inspected for correct vision metrics. These actions are logged.

At step 860 a syringe bag is printed/barcoded at bag printing and sealing station 7 (FIG. 2, III), and at step 861 the system verifies the bag is printed correctly. If so, the operator is permitted to insert the filled/capped syringe S into the barcoded/labeled bag.

At step 865 the pharmacy technician inserts the syringe S into the bag (FIG. 2, III).

At step 870 the syringe bag is sealed at the bag printing/sealing station 7. The packaged syringe can then be distributed to the patient.

As mentioned at Note 1 (FIG. 3), at each step of the above-described process the OSPS system employs comprehensive track-and-trace inspection/validation of the syringe and, when required, the bulk medication container, to insure that the packaging process is occurring correctly and to compile an audit trail of the current and past locations (and other information) for each syringe. If all process steps 800-870 occur correctly, the syringe S is approved and made available for distribution to the patient (see FIG. 1, step 770).

If a process step fails then as seen at step 760 of FIG. 1 the syringe or medicine container is rejected (and barred from distribution to the patient).

The core method and possible variations are herein implemented in several detailed embodiments of a system suitable for preparing patient-specific doses of liquid medications into oral syringes on a just-in-time basis. Various alternate embodiments of the invention may omit selected steps (and their performance station) where such is/are not required. The needs of the operating institution and the cost aspect of automating certain steps may direct which steps/stations (if any) are to be performed manually by an operator interfacing with the apparatus and which may be automated. For example, the syringe S handling can be accomplished in numerous ways, the simplest option being described above in regard to FIGS. 2-3. In this instance, one operator packages one syringe at a time sequentially from syringe selection through bagging that syringe S until each of the syringes S that need to be filled with a specific medication are packaged (see FIG. 2). However, several syringe handling variations are given below.

Alternative Syringe Handling Options

Figure 22A:
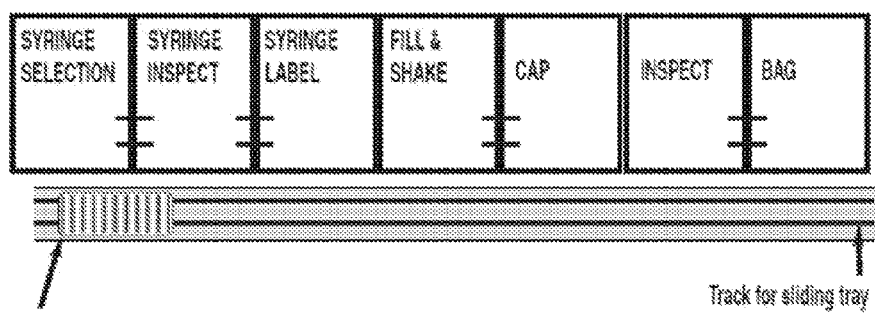
FIG. 22A is a process drawing depicting grouped stations with a multiple syringe compartment tray (Option 3)
Figure 22B:
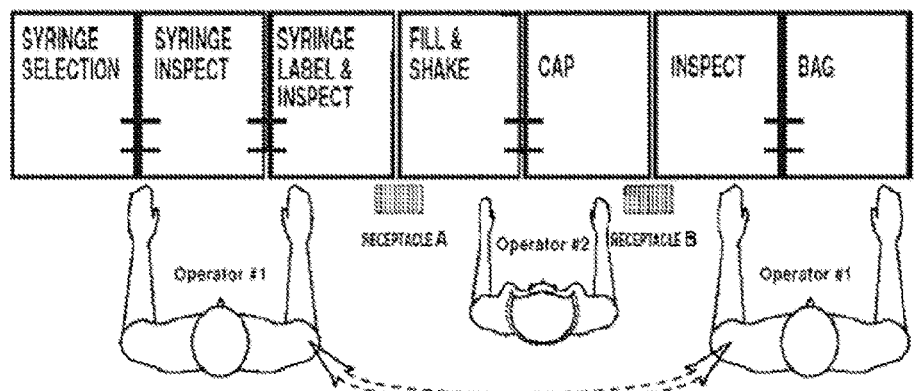
FIG. 22B is a process drawing with one operator and three and grouped stations (Option 2)

As mentioned above the handling of the syringes S on the packaging line can be accomplished in numerous ways, the simplest option (Option 1) being described above with regard to FIG. 3. However, productivity of the packaging line can be increased using other syringe handling variations. Some of the alternate syringe handling options are as follows:

Option 2—Similar to Option 1 but two operators process/package some or all of the syringes S at one time as a group, at each of three grouped stations, wherein a first operator processes/packages some or all of the syringes S at one time at station 1, then moves to station 3 while a second operator processes/packages some or all of the syringes S at one time at station 2. As shown in FIG. 22B, for Option 2 a first group of stations includes syringe selection from the syringe storage location 3, inspecting the syringe for size and color, and labeling the syringe. A second group of stations comprises filling and capping the syringe at syringe filling station 5 and capping station 8. A third group of stations comprises inspecting and bagging the syringe at vision inspection station 9 and bagging station 7. All of the syringes S that are to be filled with the same medication would be processed collectively at the first group of stations by operator 1 and then placed in a first receptacle to be picked up by the second operator. While this is taking place, operator 2 may begin to process some or all of the syringes from the first receptacle at the second group of stations, placing processed syringes in a second receptacle. When operator 1 has completed the tasks of selecting a syringe, verifying that it is correct, labeling the syringe and verifying that it was labeled correctly, he or she may move to the third group of stations to process some or all of the syringes in the second receptacle until all of the syringes are packaged with the specific medication. Then the next medication would be packaged. To facilitate this grouped approach, as an alternative, FIG. 22A shows a multiple syringe compartment tray which slides along a track to shuttle multiple syringes S back and forth to successive grouped stations and may be used in place of first and second receptacles.

Option 3—Similar to Option 1 but one operator processes/packages some or all of the syringes S at one time as a group, at each of three grouped stations before proceeding to the next grouped station. Similarly to Option 2, in Option 3 a first group of stations includes syringe selection from the syringe storage location 3, inspecting the syringe for size and color, and labeling the syringe. A second group of stations comprises filling and capping the syringe at syringe filling station 5 and capping station 8. A third group of stations comprises inspecting and bagging the syringe at vision inspection station 9 and bagging station 7. All of the syringes S that are to be filled with the same medication would be processed collectively at the first group of stations 3, 4, then all of the syringes would be processed at the second group of stations 5, 8, and then all of the syringes would be processed at the third group of stations 7, 9 until all of the syringes are packaged with the specific medication. Then the next medication would be packaged.

Figure 23:
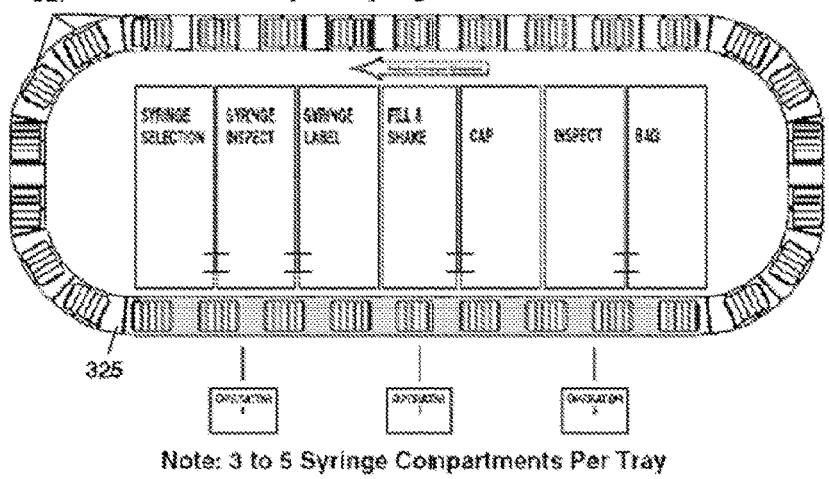
FIG. 23 is a process drawing with three operators and three and three grouped stations (Option 3).

Option 4—Similar to Option 2 but three operators are utilized, one at the first group of stations 3, 4, one at the second group of stations 5, 8, and one at the third group of stations 7, 9. To facilitate this, a carousel conveyor 325 is shown in FIG. 23 with multiple trays 327, each containing 3-5 syringe compartments per tray. The trays 327 rotate around the carousel 325 past three operators positioned one per each group of stations.

Figure 24:
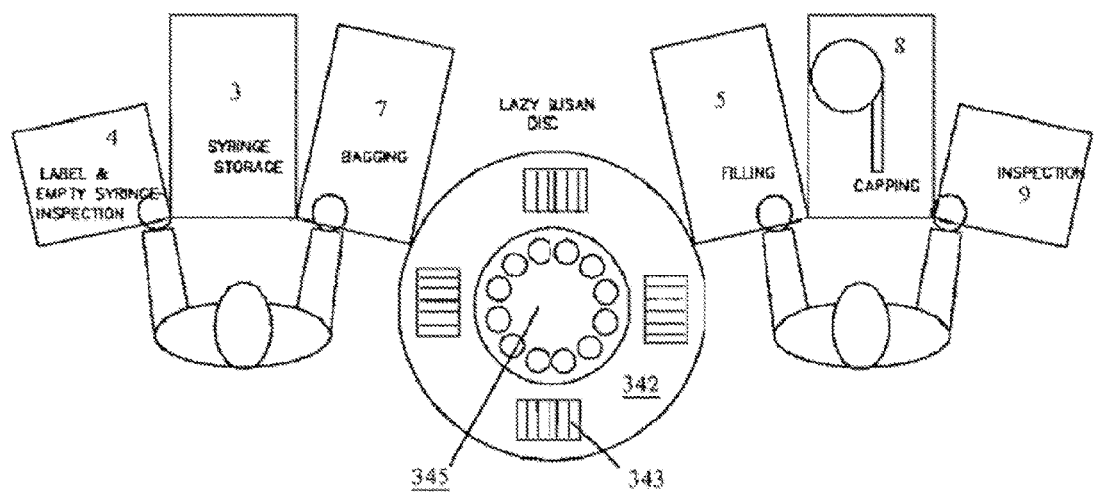
FIG. 24 is a process drawing with two operators situated around a lazy Susan (carousel-like) disc 342.

Option 5—Similar to Options 1, 2 and 3 but two operators are situated around a lazy Susan (carousel-like) disc 342, as shown in FIG. 24. Operator 1 selects, labels and inspects empty syringes S for size and color and places them in trays 343 located radially arranged on the disc 342. Additionally Operator 1 collects the medication bottles and either stages them, or an upper tier 345 of the disc 342 retains them for the second operator.

Operator Two receives the syringes S and medication bottles via the rotating disc 342 and performs the filling and capping at stations 5, 8, respectively. Operator Two may also do the filled syringe inspection at station 9. At this point it may be necessary to opt for an Operator Three to do the filled syringe inspection at station 9. Operator Two or Operator Three may then place the Filled, Capped and Inspected syringe S onto the rotary disc 342 to be indexed back to Operator One for bagging at station 7.

Figure 25:
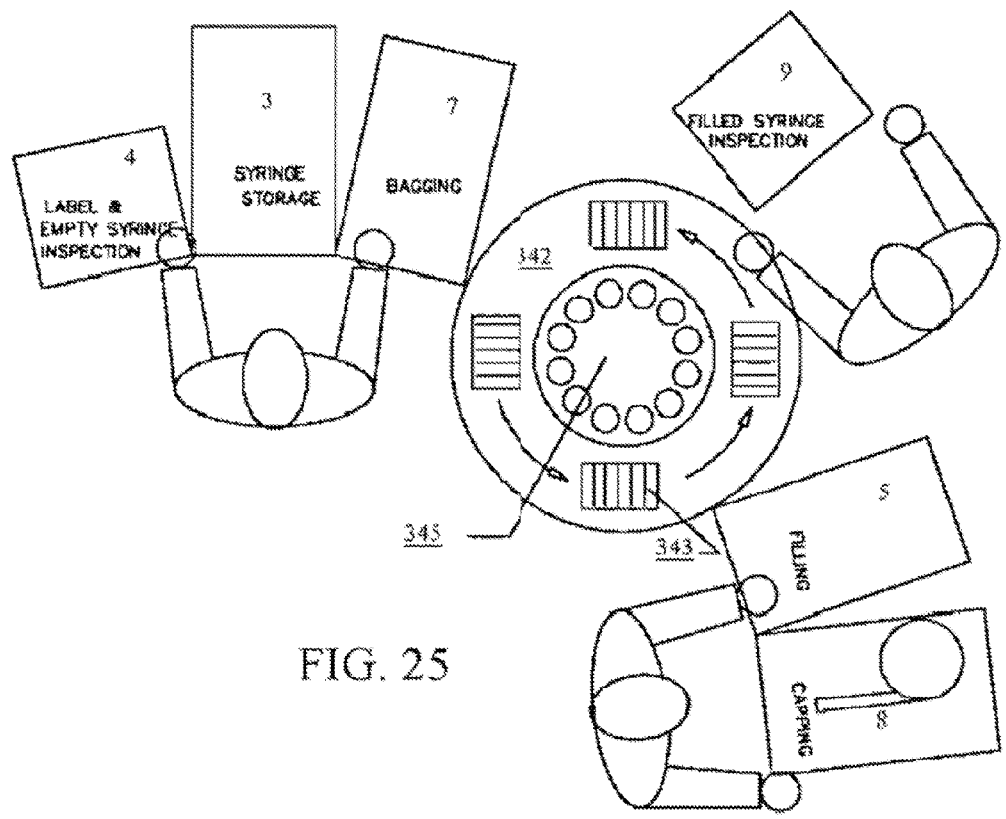
FIG. 25 is a process drawing with three (3) operators situated around a lazy Susan (carousel-like) disc 342.

Option 6—Similar to Option 4 however this system utilizes (3) operators. As seen in FIG. 25, Operator One inspects empty Syringes for size and color, applies a flag label to syringe S and places it on the lazy Susan disc 342 in trays 343. Operator Two, places the empty inspected syringe S into the filling station 5 and fills, caps and places them onto the disc 342 for transport to Operator Three. Operator Three inspects the filled syringe for correct dosage. The syringes S are then conveyed back to Operator One for bagging at station 7.

Referring back to FIG. 2, each station of the pharmacy automation system 100 for oral syringes is described below in more detail.

Medication Container Login & Orientation Station 1

The first station in the process of the present invention is Medication Container Login & Orientation Station 1 (see FIG. 2 I) at which the bulk medicine is prepared for use in the overall system 100. Medication Container Login & Orientation (MCLO) Station 1 is a standalone desk unit that provides a facility for inputting needed information into the OSPS database via scanner 95 and data entry terminal 96, apply barcodes as needed via label printer 97, decap bulk containers 104 at optional capping/decapping station 93, refit and/or retrofit them as necessary with a container/syringe interface (as will be described) at capping/decapping station 93, and optionally photograph them using a label photographing station 98. All of the scanner 95, data entry terminal 96, and label printer 97 are commercially available components. MCLO Station 1 is standalone so that it can be positioned as desired. Medicine for oral syringes is provided in liquid form in a container with a manufacturer-applied safety cap. An object of the present invention is to be able to insert a syringe nozzle into the containers to withdraw a proper dose of medicine into the syringe. To be able to do this, manufacturers must supply a specialized cap or insert, or the pharmacy technician must replace or supplement the manufacturer-supplied cap with a container/syringe interface.

Referring back to FIG. 2 I, at MCLO Station 1 a number of bins 12 are provided for storing various sizes and configurations of container/syringe interfaces 210, 212, 214, 216, 220, 221, 226, and the Baxa™-type or PIBA variations for caps 223 and 224, both integral and separable, (see FIGS. 5, 27-34 and 44) as needed to fit all standard container sizes. As described above in steps 910 through 965 (FIG. 4), OSPS system 100 guidance for the manual container 104 selection process and return process (along with the container/syringe interface 210, 212, 214, 216, 220, 221, 226, 223 and 224 and syringe S selections) may be "system-guided" as described above. Each container/syringe interface storage compartment 12 (see FIG. 2 I) may be enclosed by a magnetically-actuable door so that access to each location may be electronically controlled by the local OSPS computer, or illuminated by an LED light, or equipped with a light curtain so that the local OSPS computer can monitor access to the proper location.

OSPS system 100 guidance for the manual container 104 selection process employs a software module that relies on all three of the information components stored in the OSPS system database: 1) product information from the manufacturer or other external sources describing the medicines and their containers (size, dose, handling requirements, etc.); 2) prescription-specific information from the hospital identifying the prescription details and patient to receive it; and 3) OSPS runtime information such as the amount of medicine previously taken from a given bulk container. The exact container 104 location is provided to the operator via OSPS system 100 guidance who retrieves the container from the Storage facility 2. Again the Storage facility 2 may be fitted with magnetic doors, LED lamps or light curtains either to compel the proper selection, draw the operator's attention to it, or provide an alarm in case of a wrong selection.

In operation, and as described above with regard to FIG. 4 (medication container orientation and log-in process steps 961-963), the OEM caps on medication containers 104 are manually removed and replaced with an applicable adapter cap, i.e., a valved PIBA 212 (see FIG. 5). The OSPS local computer instructs the operator which of the valved adapter cap sizes in storage bins 12 (FIG. 2) to select for insertion into the medication container 104 (step 963). The labeler 97 generates a 2D barcode label which includes the location of Storage facility 2 (see FIG. 2 II) that the medication container 104 (see FIG. 2 I) is to be stored at. The operator places the 2D bar code on the bottom of the medicine container, and the 2D barcode is scanned by scanner 95, and optionally photographed using a label photographing station 98. All general and container specific information derived by scanning or supplemental data entry at data entry station 96 is recorded in the local OSPS computer database, including the storage location of the bulk container 104 in Storage facility 2 and the expiration date of the medication container. The operator then manually stores the container in the Storage facility 2 assigned by the OSPS computer. If the container is to be stored in light protected storage 2 II c or refrigerated storage 2 II b the track-and-trace software ensures compliance. Later, when needed to fulfill a batch of oral syringe prescriptions an operator will select (with system guidance) a container 104 of the desired medicine from the Storage facility 2 with container/syringe interface 210, 212, 214, 216, 220, 221, 226, 223 and 224, (see FIGS. 5, 27-34 and 44) applied and load it into the filling station 5 where the 2D bar code label on its base is automatically scanned by scanner 121 at the filling station 5. The medicine is verified by the scanning as to proper content, available fluid volume and other attributes before being filled at filling station 5.

A second station in the packaging process according to the present invention is a storage bin 3 (see FIG. 2 III) for storage of empty syringes. The syringe storage 3 preferably incorporates a separate syringe compartment for each size of syringe that the system anticipates needing in the course of a production run. Again, this manual selection process (along with other manual selections) is "system-guided" as defined above in respect to syringe S selection as well. As with medicine container 104 selection, the software module ascertains from the patient-specific information the appropriate dose of medicine to determine the specific syringe S size to retrieve. The location of that syringe S is ascertained from the database, and the exact syringe S location in syringe storage 3 is presented to the operator who retrieves it from the syringe storage 3. Again the syringe storage 3 may be fitted with magnetic doors, LED lamps or light curtains either to compel the proper selection, draw the operator's attention to it, or provide an alarm in case of a wrong selection. In still other embodiments the syringe storage 3 selection may be semi-automated so that the appropriate syringe S is ejected to the operator under control of the local OSPS computer. The selection software module calculates the most appropriate syringe S size based on the required prescription information dosage, the known volume of the syringe selections (the following standardized oral syringe sizes: 0.5 ml, 1 ml, 3 ml, 5 ml, 10 ml, 20 ml, 35 ml, 60 ml), identifies the syringe size to accommodate the fill volume of the prescription, and presents the syringe storage 3 location to the operator who retrieves the syringe from the proper magazine (with help of LED indicator, magnetic door, light curtain, ejection mechanism or otherwise).

A third station in the filling and packaging process is the syringe size/color inspection station 11 which verifies that the correct syringe S has been selected. The syringe size/color inspection station 11 is described more fully below with regard to FIG. 15A.

The fourth station is a flag label printer/applicator 4. After determining that the syringe S is the proper size and color, the operator inserts the syringe into syringe label printer/applicator 4. As described above relative to FIG. 3 (step 837), the operator prints a syringe label at syringe label printer 4. The labeler is in communication with the local OSPS computer and automatically prints self-adhesive labels bearing information regarding the prescription such as the eventual contents of the syringe (medicine type, concentration, dosage, expiration, scheduled administration, etc.) and its intended recipient (name, room number, etc.) along with a bar code identifying a central record of this information in the OSPS database. The label includes a 2D barcode though other labels such as RFID may be used. The label is inspected to verify the accuracy of the printed information before it is attached to the syringe S. The label is supported by hinged arms of the applicator and held by vacuum pressure while the applicator advances to envelope the syringe barrel with the hinged arms coming together to join the label as a flag to the barrel of syringe S. Alternatively, the flag label may be applied manually by the operator. A portion of the label around the barrel must be transparent to permit dosage markings of the syringe to be clearly visible.

As an alternative to the flag label printer/applicator 4, an on-demand label printer may be used which prints a patient-specific label on demand. This arrangement would require the operator to manually apply the label to the syringe. After the label is printed, the operator will verify that the syringe was labeled correctly. This option is less expensive than the use of a semi-automatic flag label printer/applicator 4 and will be offered as an option for substitution of same.

Figure 16A:
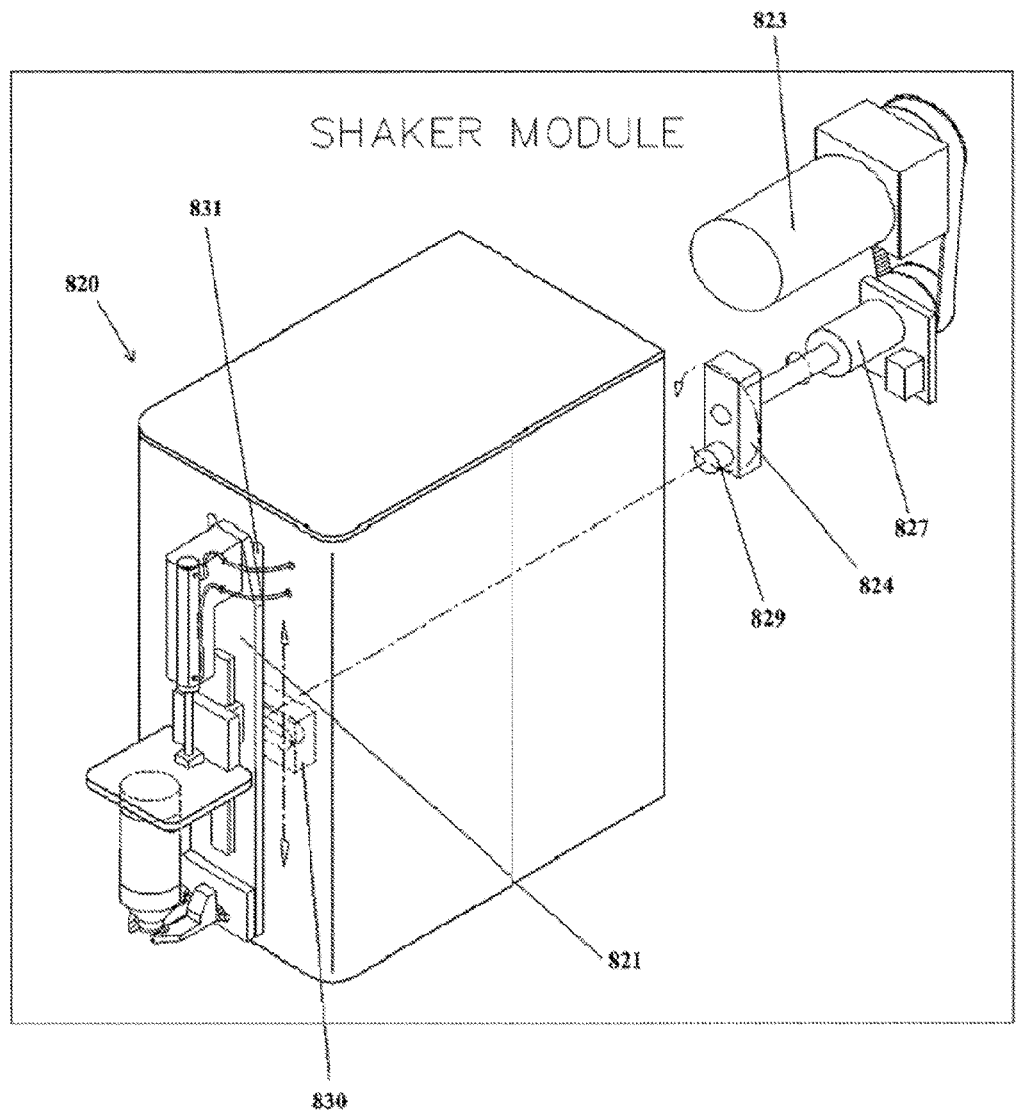
FIG. 16A illustrates an embodiment of a shaking mechanism 820 integral to the filling station 5.

A fifth (optional) station is a medication container shake station for automatically shaking the medicine container when necessary (see FIGS. 16A and 16B). A shaking mechanism 820 integral to the filling station 5 is described below. An alternative, remotely-positioned medication container shake station 6 is described more fully below with regard to FIG. 17 while a standalone or integral shaker module is described more fully below with regard to FIG. 16A.

For certain medications, such as those in the form of emulsions, liquids containing particulates or other non-homogeneous liquids, shaking is required prior to filling to render the mixture homogeneous. Within this category of medications, certain medications need to be shaken at more frequent intervals, and with a greater intensity, than other medications based on the unique characteristics of each medication. Embodiments of the instant invention comprise an electronic medication database accessible by the OSPS-S system. Information about any required shaking protocols for each medication may be stored in the medication database in association with the relevant medication(s). At the Medication Container Orientation and Login Station (FIG. 2 (I)) described herein, the method according to the present invention may involve the printing of a 2D barcode for each medication bottle which, when scanned at the filling station 5, provides the OSPS-S system with the required shaking protocol, if any, for the scanned medication. This will then prompt the OSPS-S system to cause the integral shake station 820 to shake the medication container before or after the filling operation with the frequency, intensity and in the intervals as required for the given medication. This process advantageously prevents medication that is prone to settling or separating from doing so such that each syringe contains the proper composition of medication.

The sixth station is the syringe filling station 5 for filling the syringes S. The operator positions the empty syringe S (step 840) at the syringe filling station 5. A scanner 121 is resident at the syringe filling station 5 to automatically scan the machine readable label on the bottom of the container 104 to again verify that the selected item is correct. The hand-held scanner at the fill station 5 scans the label attached to the syringe to verify that the appropriate syringe is being used. The medicine container 104 and the syringe S are loaded into the filling station 5 in various ways dependent upon the container/syringe interface that is used. The fourteen container/syringe interfaces and associated procedures for use are discussed in more detail above and below. The system automatically fills the syringe S with the medicine by calibrated withdrawal of the plunger.

The seventh station is a visual inspection station 9 which comprises optical inspection to optically determine if the syringe is filled correctly. On this basis the System 100 accepts or rejects the weighed/inspected syringe.

FIG. 6A is a perspective view of an exemplary vision inspection station 9 in which syringe fill volume is inspected by a CCD imager 330 that optically detects by image analysis if the syringe S plunger is at the correct location, the volume above the plunger and below the syringe tip is filled with product, and also checks for bubbles in the product.

With respect to FIGS. 6A and 6B, the illustrated embodiment of the vision inspection station 9 generally comprises a flat base 92 with vertical syringe-mounting plate 93 at one end, caddy-corner to a vertical camera mounting plate 94. CCD imager 330 is mounted overhead on a camera-mounting bracket 95 extending upward from the camera mounting plate 94. A syringe holder 96 protrudes from the vertical syringe-mounting plate 93 and suspends a syringe by its cap (two yoke fingers under the cap). An optional syringe clamp 99 may be provided opposite the syringe holder 96 for clamping the syringe therein. In its simplest form (shown), syringe clamp 99 is a spring-biased jaw that clamps against holder 96 to secure the syringe. A backlight panel 97 resides directly behind the syringe S (beneath syringe holder 96). Two side-mounted lights 98 provide frontal illumination.

In operation, the vision inspection station 9 establishes and maintains a "Reference Point" on each syringe which is consistent for all syringes despite size, nozzle offset and other variables. In accordance with the invention the reference point is selected to be just below the syringe tip at its intersection with the top of the syringe body. Since the syringe cap covers most of the syringe tip, and that tip volume is never dispensed, the tip can be ignored from any vision reading taken. The filled and capped syringe S is preferably held stationary in the spring-loaded yoke fingers of syringe holder 96 by its cap, while the backlit camera CCD 330 measures from a reference point to the seal ring of the syringe S plunger. Since the syringes are hung by their caps within a common yoke they will all have the same zero reference point, despite varying sizes. The reading from the "Reference Point" downward to the seal ring of the plunger comprises a numerical dimension for the specific syringe S size relative to the prescribed dose (the size selected being the next larger size in excess of the dose). Once taken, the OSPS computer compares the reading to a predetermined value associated with that syringe size and every increment on the syringe. For example, if a 10 ml dose is prescribed the OSPS computer will recommend a 20 ml syringe, in which case the distance from the "Reference Point" downward to the seal ring of the plunger (when fully inserted) should be 32.75 mm or 1.289". This way, given knowledge of the prescribed dose and the syringe size, the system can accurately determine if the fill dose is correct. Otherwise it will be rejected. The accuracy of fill should be +−5% of target. In addition, the vision inspection may also include phase-contrast imaging to measure bubbles in the syringe. Phase contrast imaging exploits differences in the refractive index of the contents to differentiate bubbles. Some bubbles are tolerable, but too many are not. The vision inspection may employ phase-contrast imaging as a bubble check. This same process is used to determine if the syringe is "short filled" based on differences in shading. Any voids or bubbles are interpreted as a mixed pixel count in either light or dark depending on the opacity of the medication derived from the OSPS computer database. If the syringe volume inspection device 9 determines that the syringe S is filled to the correct volume with an acceptable amount of bubbles and no voids, it will be accepted. An acceptable bubble/void percentage is +/−2%. Optionally, a digital photograph of the filled syringe may be taken and archived for track and trace purposes. In a preferred embodiment, the color of the light may be changed to give the greatest possible contrast over liquids of different colors and opacities. The lighting color may be determined by the vision inspection station 9 based on a scan of the 2D barcode on the syringe to be inspected.

The illustrated embodiment reduces the footprint (size) of the vision inspection system 9 using a mirror to break up focal distance into shorter lengths (here two, though additional mirrors may be used). Specifically, the overhead camera 330 view is reflected off a mirror 333 mounted to wall 94, and is then focused on the syringe S being inspected.

Figure 6D:
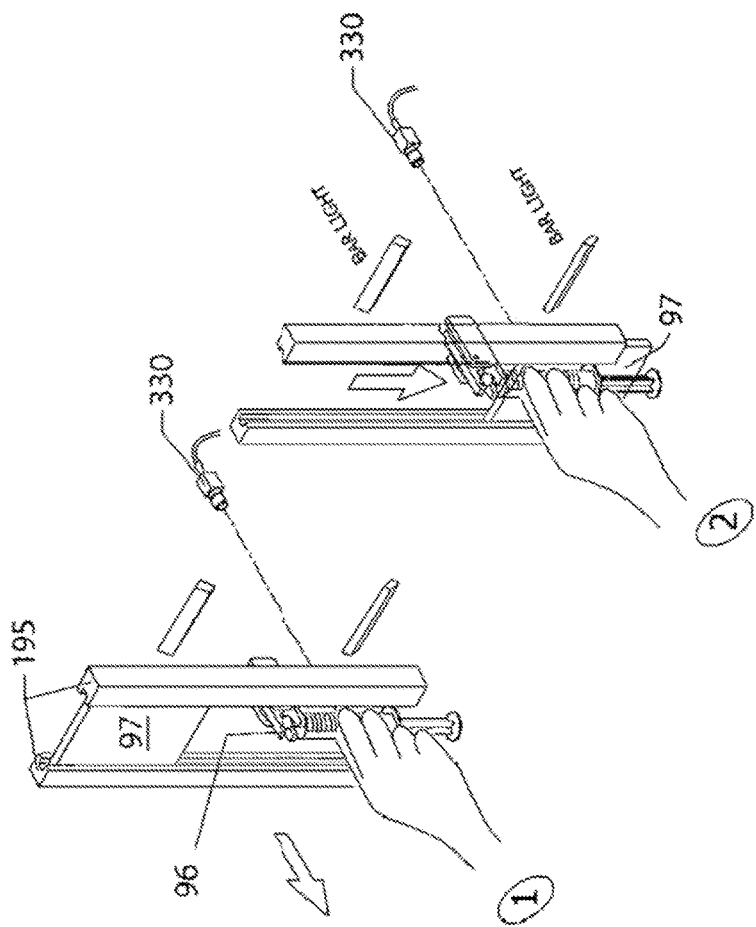
FIG. 6D shows another alternative articulating design for the backlight panel 97.

FIGS. 6C and 6D show two alternative articulating designs for the backlight panel 97 which resides directly behind the syringe S (beneath syringe-holder 96), both perspective sequential views, which facilitate easier loading of the syringe S from behind. In FIG. 6C, the syringe-holder 96 is mounted from a suspension or other non-obtrusive bracket to facilitate rearward access. The backlight panel 97 is mounted behind the syringe-holder 96 on hinges or pivots 198 as shown, to allow the backlight panel 97 to be opened or closed like a door. As shown in the sequence, the operator places the filled, capped syringe S into the syringe-holder 96 at (1), closes the backlight panel 97 at (2), the CCD imager 330 images the syringe S against the backlight panel 97 at (3), and the backlight panel 97 is reopened at (4) and the syringe S removed.

FIG. 6D shows a guillotine-style backlight panel 97 slidably mounted on a pair of spaced-apart vertical rails 195. Backlight panel 97 moves up and/or down within rails 195. As shown in the sequence, the operator places the filled, capped syringe S into the syringe-holder 96 at (1), and closes the backlight panel 97 whereupon the CCD imager 330 images the syringe S against the backlight panel 97 at (2). The backlight panel 97 is then reopened and the syringe S removed.

As still another alternative, the inspection may be accomplished with a check-weigh scale to weigh and/or inspect the filled syringe S to verify the syringe is as labeled. In this case, the OSPS software calculates target weight based on the fill size in cc's and multiplies by the specific gravity to derive weight. The specific gravity of each medication is stored in the OSPS database along with the percentage +/−% deviation that is acceptable for the actual fill weight. If the actual fill weight is in the target range, it is accepted. If not, it is rejected.

The OSPS software calculates the target weight based on the fill size in cc's and multiplies by the specific gravity to derive weight. The specific gravity of each medication is stored in the OSPS database along with the percentage (+/−%) deviation that is acceptable for the actual fill weight. If the actual fill weight is in the target range, it is accepted. If not, it is rejected.

An eighth station 8 is the semi-automatic syringe capping station described below in detail with regard to FIG. 10. The syringe capping station 8 facilitates accurate placement of syringe caps onto filled syringes S.

The ninth station is a bag printing and sealing station 7 (see FIG. 2 III). The bagging station 7 is a commercially available Hand Load Printer/Bagger for hand load labeling and bagging applications. It is networked to the local OSPS computer to automatically print the bag that the syringe S will be packaged in. The bag is printed with information regarding the prescription such as the eventual contents of the syringe (medicine type, concentration, dosage, expiration, scheduled administration, etc.) and its intended recipient (name, room number, etc.) along with a bar code identifying the same content. After printing a bag the system inspects the print on the bag to make sure that it is correct. If so, the operator is permitted to place the filled/capped syringe S in the bag, the system confirms that the syringe was placed in the bag, and the bag is then sealed.

If all the steps are completed correctly the syringes are distributed for administration to the patient.

One skilled in the art will recognize that certain steps may be completed in various alternate sequences to achieve the same result, and features may be modified or eliminated as a matter of design choice.

At initial MCLO Station 1 an operator prepares bulk medicine containers for use at the automated syringe filling station 5. Preparation entails applying one of the above-described container/syringe interfaces. Again, each medicine container is pre-labeled with a unique identifying number, for example, in barcode format adhered to the bottom of the container. Preparation of the container 104 also includes scanning, verification, optional photographing, and recordation of container 104 label information including content information (name, manufacturer, full volume, concentration, etc.), batch or production information, and expiration information with its assigned container 104 in a medication track and trace database. Various other parameters for each medicine can be associated with each record in the database such as the maximum flow rate at which a certain medicine can be withdrawn from its storage container (i.e. to prevent cavitation/inaccurate fills), the storage temperature (ambient or refrigerated), the required frequency of shaking/agitation of each medicine to keep any particulate matter properly suspended/distributed (e.g. between each syringe fill dispense cycle or only at the start of a series of syringe fill dispense cycles).

Each barcode (or possibly RFID tag or other label) preferably references the following information:
Batch number
Expiry date
Storage instructions
Product name
Strength
Name of the active ingredient(s)
Dose form
Warning statements
FDA number
Des product need to be shaken before use? If so, how often?
Does product need to be refrigerated before use? If so, temp?
Does product need to be protected from light?
Volume of original bulk medication container?

The information available from the pharmaceutical manufacturer's barcode on the medication container varies from manufacturer to manufacturer. The operator is prompted to enter any missing data directly into the computer data entry terminal 96 at MCLO Station 1. The information from the pharmaceutical manufacturer's barcode label plus the variable information is stored in the medication container database which is linked to the medication container by the barcode label on the base of the container, which includes the container identifying number assigned to the container 104 in the medication track and trace database. It is also important that each container 104 is marked in both human and machine readable forms (i.e. text, barcode or RFID tag) as to the type and concentration of the medication it contains along with various other information, to enable visual inspection.

The containers/bottles 104 are typically manufacturer-supplied although custom containers/bottles may be used for purposes of the present system. If the storage containers or bottles 104 are provided by the manufacturer, 20 mm, 24 mm, and 28 mm neck diameters are typical. The bulk containers may be provided in a specified, standardized format by the manufacturer, or the medicines may be refilled into standardized containers onsite.

With regard to filling station 5 in FIG. 2, the oral syringe may be entirely evacuated such that its plunger is advanced all the way into its barrel or the oral syringe may have a calibrated amount of a gas (such as air) in front of the plunger in the barrel. The syringe plunger may be withdrawn to draw the fluid into the barrel. Where a gas is present in the syringe, the plunger may be first advanced so as to force the gas into the container 104. The plunger is then withdrawn to draw the fluid into the syringe. Introduction of the gas into the container 104 slightly pressurizes the container initially and prevents the development of negative pressure within the container which would inhibit fluid flow. When the syringe is filled to the proper volume it is withdrawn.

Referring back to FIG. 2, the operator returns the prepared medicine container 104 with its container/syringe interface 210, 212, 214, 216, 220, 221, 226, 223 and 224 in the medicine Storage Facility 2 where it remains until called for. The system software monitors the contents of the medicine Storage facility 2 in terms of both identity of the prepared medicines available to be dispensed and the quantity of each medicine. The content of the Storage facility 2 is continually updated as the medicine is dispensed and the system is able to predict based on current pending prescription and historical dispensing information when the current available container of any given medication will be empty so as to advise the operator to prepare a replacement quantity of such medicine prior to emptying the existing container. Medicines exceeding their expiry dates are also identified by the system to be discarded by the operator.

After retrieving the syringe from syringe store 3 (see FIG. 2 III) of empty syringes S to be filled as described above, the operator inserts the syringe into a station that includes a syringe color/size inspection device 11 and a syringe label printer/applicator 4.

Figure 15A:
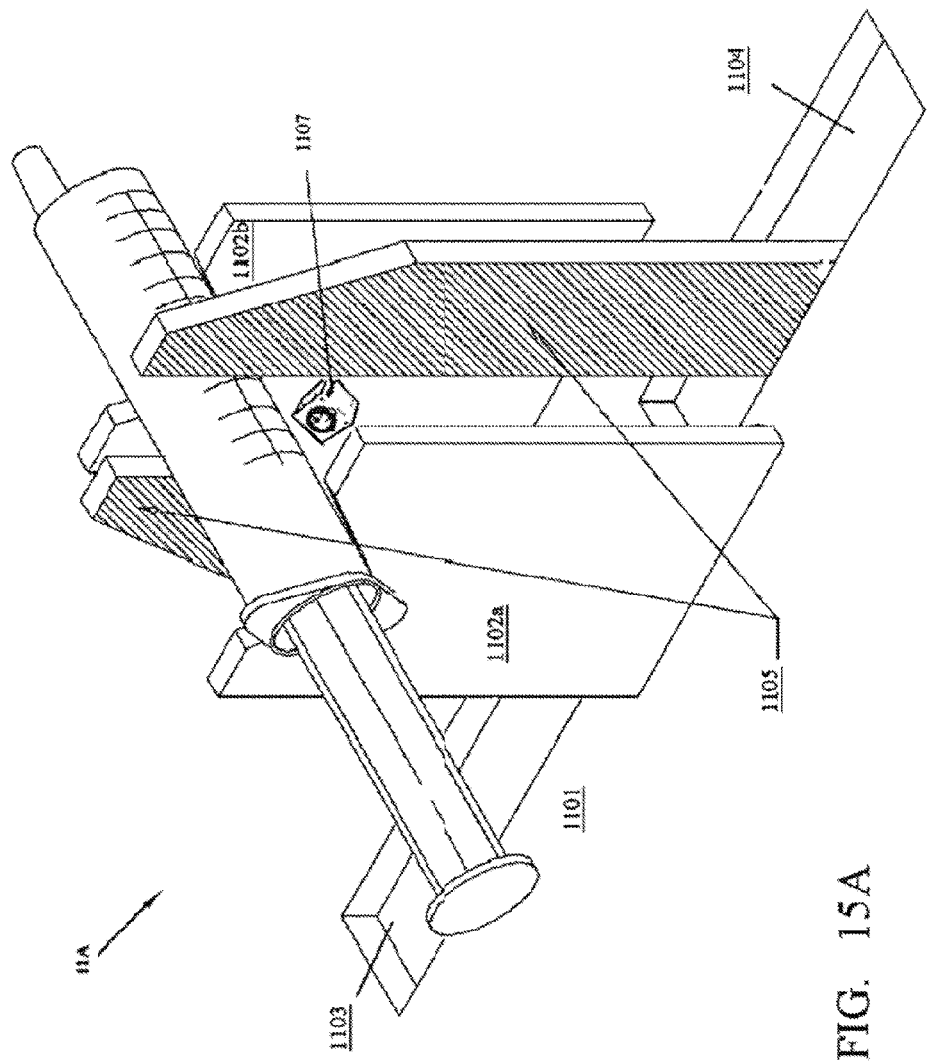
FIG. 15A is a perspective view of an embodiment of the syringe size/color station 11A which verifies that the correct syringe has been selected.

FIG. 15A is a perspective view of an embodiment of the syringe size/color station 11A which verifies that the correct syringe size (0.5 ml, 1 ml, 3 ml, 5 ml, 10 ml, 20 ml, 35 ml, and 60 ml)) has been selected by the operator. One skilled in the art should understand that syringe size/color inspection station 11A may be placed anywhere but is best placed proximate the filling station 5. The illustrated syringe size/color inspection station 11A essentially comprises a set of automatic electronic calipers connected to the OSPS Computer. More specifically, a support surface 1101 is formed with a pair of aligned slots 1103, 1104. A stationary cradle comprises a pair of spaced-apart yokes 1102a, 1102b fixedly mounted on the support surface 1101 on opposite sides of the slots 1103, 1104 for supporting the syringe S in a horizontal position. A pair of articulating caliper fingers 1105 protrude upward through the slots 1103, 1104 to embrace the syringe S on both sides. Caliper fingers 1105 are driven by an underlying caliper drive mechanism connected to the OSPS Computer which moves fingers 1105 into contact with the syringe S after the shuttle 5s has deposited the syringe S onto the yokes 1102a, 1102b. The caliper fingers 1105 rise to a height higher than the center of the largest syringe size, and in operation the fingers 1105 close around the body of the syringe S until a force is sensed (indicating contact with the syringe). At this point a measurement of the syringe body is taken (the distance between fingers 1105 is calculated) to verify that the correct syringe S has been selected. Oral syringes are often color coded in translucent colors for ease of identification. For example, oral syringes may be a highly visible amber color to distinguish its contents as an orally administered medication. To verify color, a color inspection camera 1107 is also connected to the OSPS computer and may be mounted in either of yokes 1102a, 1102b to image the color of the syringe S. A 3-CMOS imager is preferred for this application to capture RGB pixel data, which is compared by OSPS Computer to a color lookup table or subjected to another color-matching algorithm to verify the proper syringe color. If size and/or color are correct, labeling and/or further processing of the syringe S will take place.

Figure 15B:
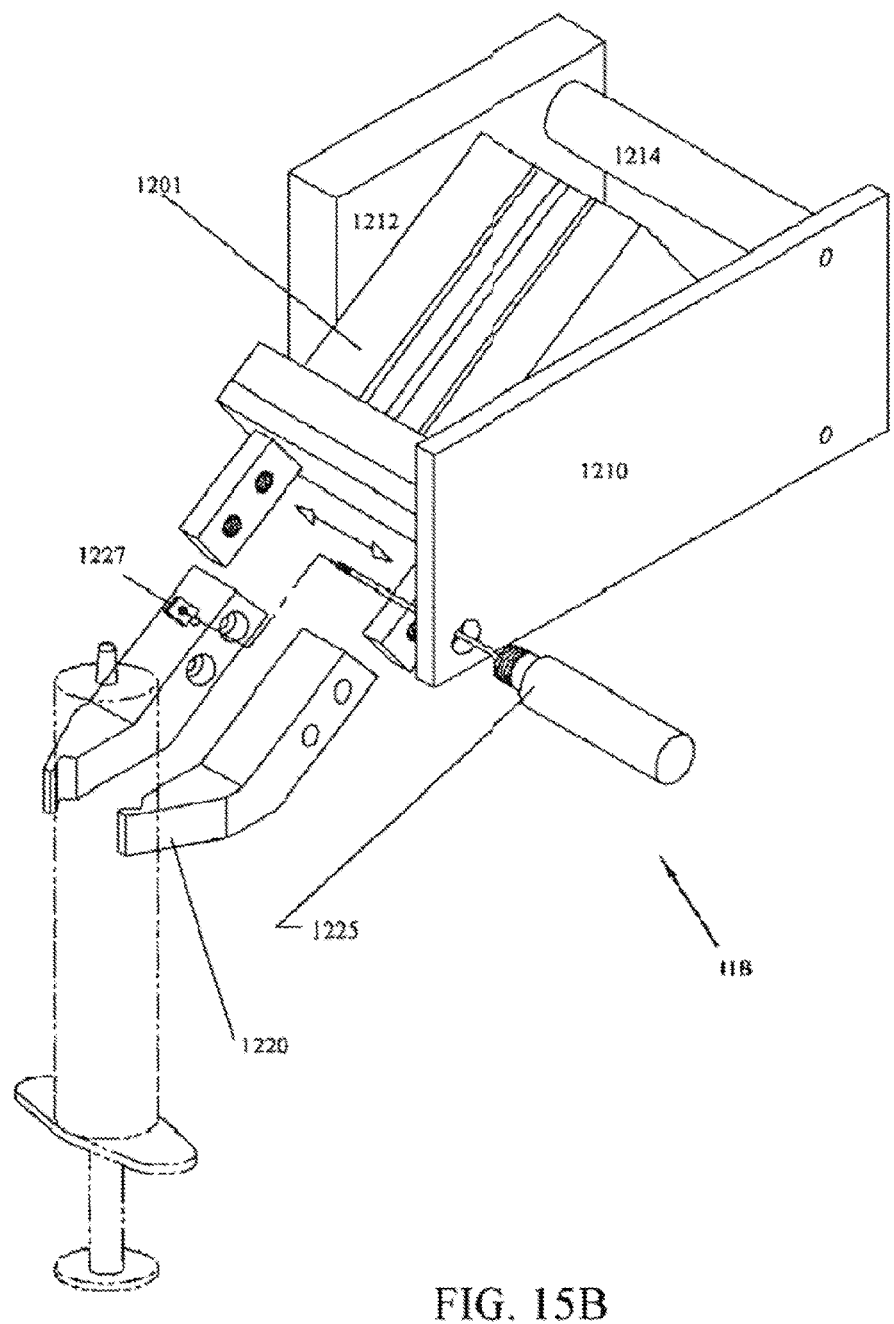
FIG. 15B is a perspective view of an alternate embodiment of the syringe size/color station 11B which verifies that the correct syringe has been selected.

FIG. 15B is a perspective view of an alternate embodiment of a syringe size/color station 11B which verifies that the correct syringe has been selected. Embodiment 11B comprises a parallel pneumatic gripper 1201 fixedly mounted at a downward incline within a supporting structure here comprising opposing vertical plates 1210, 1212 connected by a cross-bar 1214. There are a variety of commercially-available pneumatic grippers available in parallel, angular, radial and concentric versions, and in this instance a parallel version is used, such as a Rexroth™ GSP precision parallel pneumatic gripper. Opposing syringe gripper jaws 1220 are attached to the existing gripper 1210 arms, each jaw 1220 comprising a downward extension to a horizontally-disposed finger. The opposed horizontal fingers 1220 are formed with inwardly-disposed vertical grooves to provide a proper grip on the syringe barrel, while holding it vertically. A linear variable differential transformer (LVDT) 1225 (also called a differential transformer) is mounted in plate 1210, and its sensing piston is threaded into a collar 1227 secured to the opposing jaw 1220 for measuring linear displacement (position). The LVDT 1225 is connected to the OSPS Computer and measures the distance traveled by the jaw 1220 as it closes around a syringe S. The LVDT 1225 takes monitors an input voltage differential from a starting position to a final position after gripping the syringe S, and calculates syringe size from distance traveled by the jaw 1220. As above, to verify color a color inspection camera 1107 may be mounted in either of plates 1210, 1212 to image the color of the syringe S and thereby ensure that size and color are correct, such that labeling and/or further processing of the syringe S may take place. One skilled in the art should understand that the syringe measurement system 11B may be integrated as part of the syringe filling station 5 (see FIG. 2 III) rather than as a standalone station as shown in FIG. 15B, thereby consolidating the size/color inspection function with the filling operation.

The labeler 4 is in communication with the central controller and prints self-adhesive labels bearing information regarding the prescription such as the eventual contents of the syringe (medicine, dosage, scheduled administration, etc.) and its intended recipient (name, room number, etc.) along with a bar code identifying a central record of this information. The label is printed, scanned (inspected) and, if approved, applied to the syringe using known application methods. In one such method the label is supported by the hinged arms of the applicator by vacuum pressure while the applicator advances to envelop the syringe barrel with the hinged arms coming together to join the label as a flag to the barrel. A portion of the label around the barrel must be transparent to permit dosage markings of the syringe to be clearly visible. Alternatively, an on-demand label printer, for manual application of the label to the syringe, may be used in place of labeler 4.

FIG. 7A is an enlarged perspective view of a semi-automated syringe fill station 5 for filling the syringes S. Prior to inserting the syringe into the syringe filling station 5, the operator will have selected from the Storage facility 2 the appropriate, prepared container 104 with a valved PIBA (see FIG. 5) from which to dispense the proper medicine into the syringe S. The operator first inverts and then inserts the prepared container 104 into yoke 82C (see FIG. 7C III). The syringe S is then manually loaded by the operator into the syringe filling station 5, preferably with the plunger partially withdrawn from the barrel. The syringe S/plunger combination is inserted into the medicine container. Several support fixture/yoke variations are envisioned.

Figure 8:
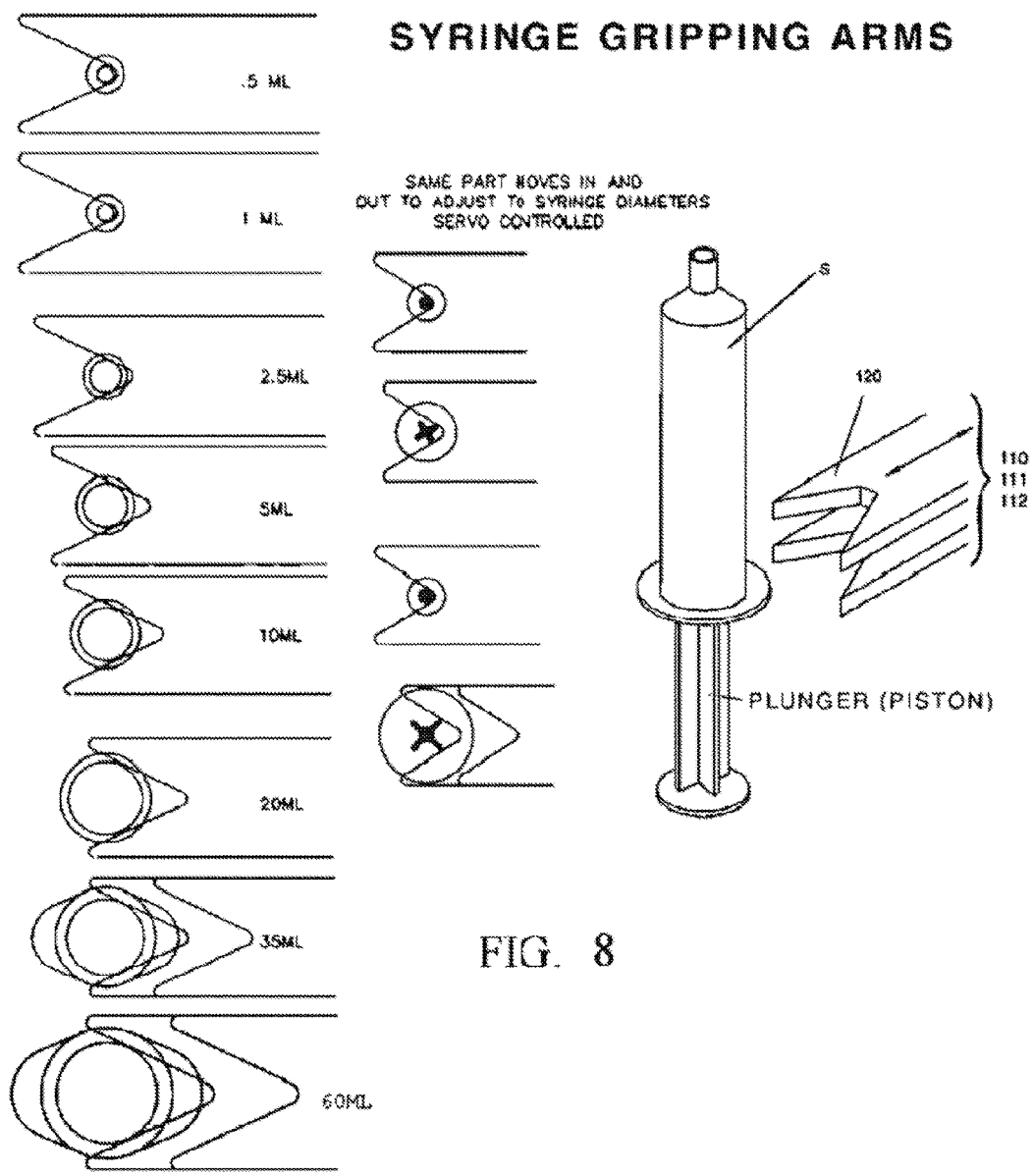
FIG. 8 is a composite view of the syringe gripping arms 110, 111 and 112 terminating in a pair of fork shaped fingers 120 that form a horizontally oriented "V" shaped opening.

As seen in FIG. 8, each arm terminates in a pair of fork shaped fingers 120 that form a horizontally oriented "V" shaped opening to engage the syringe barrel and plunger cross sections regardless of the size of these elements. Each arm is independently servo controlled and slideable in both an up-down direction and a horizontal forward-back direction to facilitate engagement with and operation of the syringe and plunger. The upper and middle arms 110, 111 grip above and below the syringe barrel flange, while the lower arm 112 grips the plunger flange. The local OSPS computer calculates the distance to move the lower arm 112, plunger lifting arm 128 and plunger flange to extract the appropriate dose of medicine based on the prescribed dose volume V and known radius or diameter of the syringe S size retrieved. The linear travel distance H equals $V/\pi r^2$, where the radius r is stored in the database. The linear travel distance H constitutes the distance that the lower arm 112 needs to travel to pull the correct amount of medicine into the syringe S. The local OSPS computer then controls the movement of fill arms 110, 111, 112 and plunger lifting arm 128 in accordance with the calculated distance H, and may also account for other variables such as medicine viscosity, volume of fill, etc. to optimize either the linear travel distance H or the filling force exerted or filling time taken along that distance.

Figure 9:
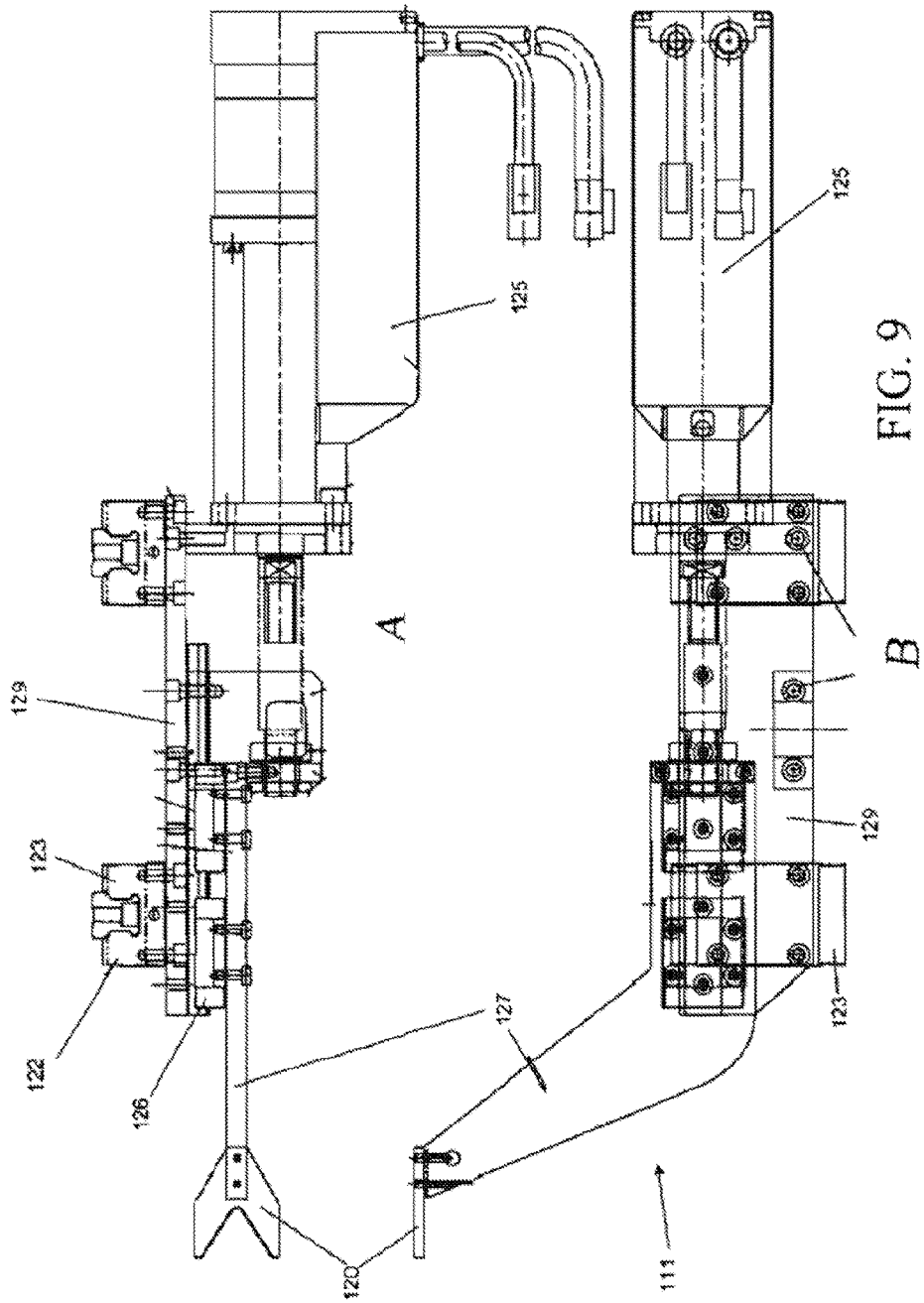
FIG. 9 illustrates an embodiment of the syringe gripping arms 111 and its drive mechanism.

With reference to FIG. 9, a preferred embodiment of the present invention provides the upper, middle and lower arms 110, 111 and 112, respectively, in a single stacked configuration each having a horizontally fixed base member 129 riding on a pair of ball slides 122 on a set of guide rails 123 vertically oriented with the housing 895 (of FIG. 7A). Vertical movement of each base member 129 on the guide rails 123 is controlled by a linear servo 124 situated below and extending into the housing 895. Each arm 110, 111, 112 is also provided with a horizontal reaching element 127 slideably mounted horizontally to each base member 129 so as to ride up or down the guide rails 123 with the base member 129 while being extendable or retractable in the horizontal to engage the syringe S. Horizontal extension and retraction of the reaching members 127 is controlled by a horizontally oriented linear servo 125 fixedly mounted to each base member 129 and engaged to the proximate reaching element 127, each which is itself mounted via a horizontally oriented ball slide assembly 126 affixed to the base member 129. The forked fingers 120 are horizontally disposed at the distal ends of the reaching elements 127. In this way the horizontal and vertical motion of each arm 110, 111, 112 is individually controllable in two dimensions.

Referring back to FIG. 7A, in addition to the upper, middle and lower arms 110, 111, 112, a plunger lifting arm 128 extends upward from below to depress the plunger of the syringe S into the barrel as will be described. The plunger lifting arm 128 is controlled by a linear servo and is vertically oriented. In certain embodiments the lower arm 112 may serve both the plunger pull-down (withdraw) and plunger lift (depress) operations.

Figure 26:
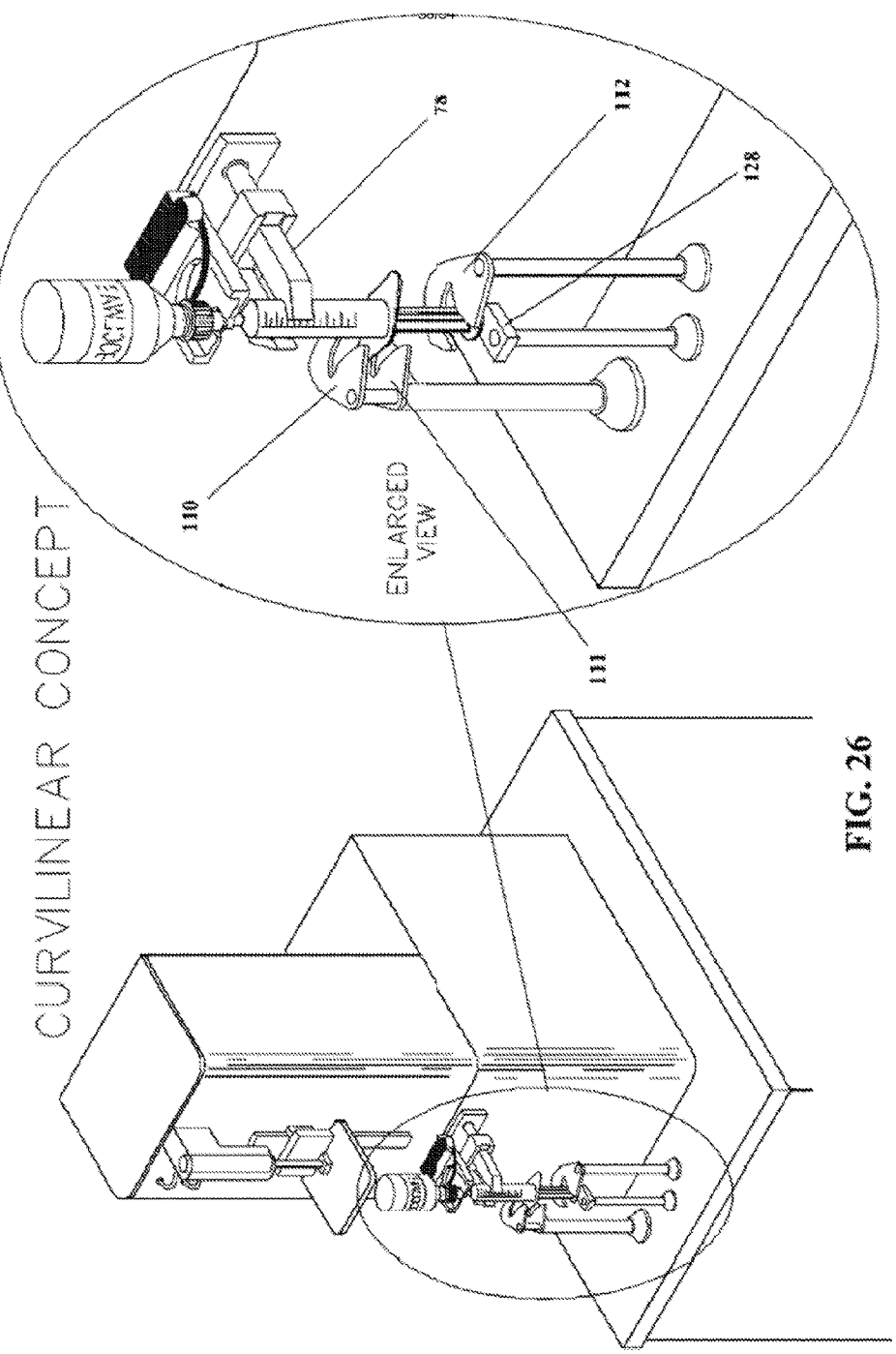
FIG. 26 illustrates an embodiment of a syringe gripping module having curvilinear distal ends.

In an alternate embodiment, as shown in FIGS. 26 and 27, instead of horizontally extending syringe gripping arms with two-dimensional horizontal and vertical motion of each arm 110, 111, 112, vertically extending syringe gripping arms are implemented with vertical and rotational motion of each arm 110, 111, 112. This is made possible by replacing the laterally-extended fork-shaped fingers each with standard "V" shaped openings with one or more right-angle plates each having a transverse curvilinear notch or "curvilinear jaw." This way, each syringe gripping arm 110, 111 and 112 terminates with at least one horizontally-oriented curvilinear jaw, wherein the notch forms an overall curved shape along the horizontal plane of the gripping arms 110, 111 and 112 which lessens in width towards its closed end. The advantage of this configuration is that the syringe gripping arms 110, 111, 112 extend vertically from the horizontal base member of the filling station and may enter the filling station through fluid-sealed bushings, whereas the above-described two-dimensional embodiment requires elongate slots to permit vertical movement of the arms, but which are difficult to seal to prevent liquid medication and other materials from infiltrating into the interior of the filling station. Where the filling station is expected to operate in a clean-room environment, the ability to environmentally seal the external filling area is an absolute requirement, and the use of vertical/rotational syringe gripping arms 110, 111, 112 rotating within sealed rotary bushings makes this possible. Additionally, in this embodiment, the sealed interface between the vertical rotating mounting elements for arms 110, 111, 112 and 128 and the base plate of the filling station prevents any liquids or other materials spilled during the filling process or otherwise from leaking into the interior of the filling station. In this embodiment, arms 110, 111 and 112 may be mounted through a horizontal base member of the filling station, extending through rotary shaft seals, and attached to linear and rotational servo motors mounted underneath the filling station base that control the motion of the arms 110, 111, 112 (as well as plunger lifting arm 128) as will be described. The servo motors thus control vertical position and axial rotation of the vertical mounting elements and therefore the arms 110, 111, 112 and 128 mounted thereon, with plunger lifting arm requiring only the capacity to raise and lower vertically, and not to rotate. Thus, as vertical mounting elements and arms 110, 111 and 112 rotate, they close on the various portions of syringe S corresponding to their vertical orientation. Arms 110, 111 and 112 may rotate as far as possible to grasp syringe S until the curvilinear gap between the fingers matches the width of the portion of syringe S upon which it closes; thus, arms 110, 111 and 112 will rotate under control of the servo motors until syringe S is snugly positioned within the gap between the fingers. In addition, upper and middle arms 110 and 111 may rest on the same vertical mounting element spaced vertically from one another, with a clamping cylinder incorporated there between to control their relative vertical orientation. Clamping cylinder may pull upper arm 110 down on top of middle arm 111 to sandwich the syringe hilt or flange between them as described. Advantageously, the use of a low cost clamping cylinder eliminates a more costly servo motor to independently operate arm 110 and/or 111. In all other respects, arms 110, 111, 112 and 128 may perform the same functions as described herein.

Prior to filling, the scanner 121 at the syringe filling station 5 reads the machine readable label on the bottom surface of the container 104 to again verify that the selected container contains the correct medicine.

Once verified to be the correct, the upper arm 110 lowers to contact the upper surface of the syringe S finger flange, and the middle arm 111 raises to contact the lower surface of the syringe S finger flange. Initially, plunger lifting arm 128 pushes the syringe piston all the way up and the lower arm 112 lowers to clamp the syringe piston downward against the plunger lifting arm 128. Priming of the syringe S takes place as lower arm 112 and plunger lifting arm 128 move up and down in concert with each other to perform the syringe priming sequence. After priming is complete and with the syringe piston fully retracted, the syringe can be filled.

During fill operations the upper, middle and lower arms 110, 111 and 112 are initially in a horizontally retracted state. The lower arm 112 engages the plunger above the plunger flange in a similar manner while the lift arm 128 extends upward to engage the distal end of the plunger. The lower and lift arms 112, 128 are brought together to engage trap the plunger flange between them, and the syringe S is entirely evacuated by fully depressing the plunger within the barrel. If the syringe S is entirely evacuated (i.e. the plunger is fully depressed within the barrel), the lower arm 112 is initially dropped, withdrawing the plunger from the barrel and drawing the medicine into the syringe. As noted, in certain embodiments the syringe may have a predetermined amount of air in the barrel to pre-pressurize the container 104. In such a situation the position of the plunger (and hence the volume of air in the barrel to be injected into the container) is determined by the system based on known parameters of the medicine, the container volume and its current fill level, and the plunger is positioned accordingly prior to insertion into the container/syringe interface by relative movement of the upper, middle, lower and lifting arms 110, 111, 112 and 128. Upon insertion of the tip in the container/syringe interface the plunger is first fully depressed by the lift arm 128 to pressurize the container and subsequently withdrawn by the lower arm 112 at a predetermined rate to fill the syringe S with desired amount of medicine without cavitation.

When the syringe is filled to the desired level, the arms 110, 111, 112 and 128 are lowered in unison and the syringe S is withdrawn from the container/syringe interface 210, 212, 214, 216 and where an elastomeric insert 225 is present it returns to it closed/sealed position. If desired, the syringe plunger may be further withdrawn from the barrel slightly by relative movement of the lower arm 112 as the nozzle is withdrawn to draw in any medicine left in the elastomeric insert 225 so as to avoid drippage.

With reference to FIGS. 40-43, where a push-pull cap 224 is used as the syringe-medication container interface to enable the medication container to interface with a Luer lock oral syringe, syringe filling station 5 additionally comprises a grooved block 400 for actuating slide disc 91 to open and close push-pull cap 224 between each syringe fill. As shown in FIG. 43 (at A), grooved block 400 comprises a horizontal block having a cutout through the entire height thereof to accommodate the exterior diameter of push-pull cap 224 above and below slide disc 91. At a height-wise midpoint of the inner wall of the cutout is a groove corresponding to the outer diameter of slide disc 91 such that slide disc may be captured within the groove when the medication container is properly positioned in yoke 82. Grooved block 400 is positioned a given distance below yoke 82 such that it captures slide disc 91 within its groove when push-pull cap 224 is in a closed position (with slide disc 91 raised and tab 86 in upper groove 87a; see FIG. 29 at B) and is movable vertically relative to stationary yoke 82.

Figure 41:
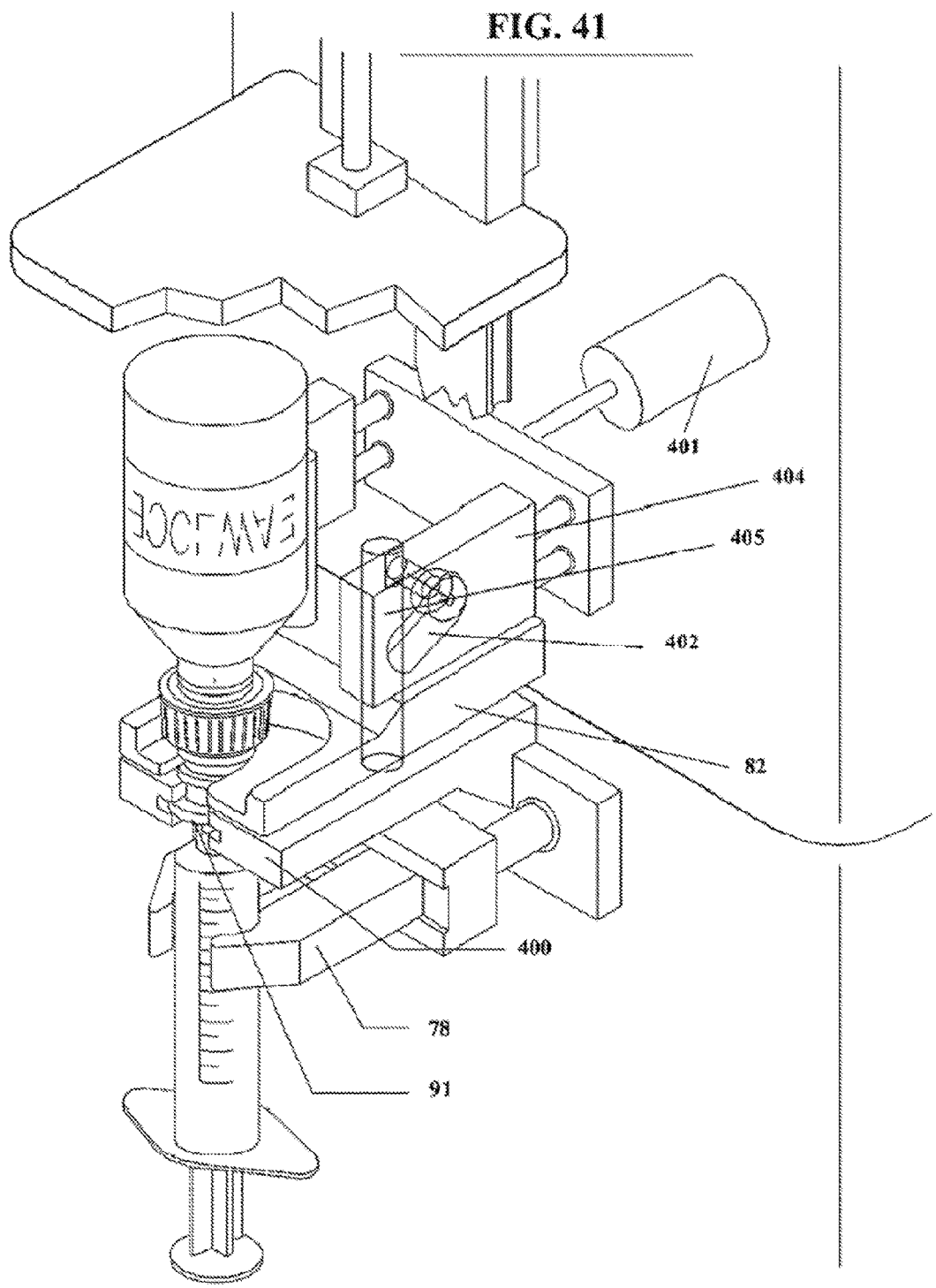
FIG. 41 is an enlarged perspective view of the actuation mechanism for filling station 5 according to the embodiment shown in FIG. 40.

In a first embodiment, shown in FIG. 41, grooved block 400 is operatively connected to a horizontal air cylinder 401 via two cams 404 comprising cam slots 402. Air cylinder 401 is in turn connected to OSPS software for controlling the operation of air cylinder 401 based on one or more programmed syringe filling sequences. When air cylinder 401 is retracted, cams 404 move inward towards air cylinder 401 and away from the syringe and medication container. Two cam followers 405 each have a horizontal arm, a portion of which is disposed in one of the two cam slots, and a vertical arm connected to the horizontal arm and extending downward through yoke 82 to connect to grooved block 400. Cam followers 405 are held stationary within the horizontal plane but movable within the vertical plane, such that when cams 404 move inward, cam followers 405 are pushed downward following the downward incline of the cam slots 402 in the direction opposite that in which cams 404 are moving. By their attachment to grooved block 400, cam followers 405 in turn push grooved block 400 downward which forces the slide disc 91 held within grooved block 400 downward, opening push-pull cap 224. Likewise, when air cylinder 401 is extended, cams 404 move outward away from air cylinder 401, cam followers 405 are pulled upward following the upward incline of the cam slots 402, grooved block 400 is pulled upward and slide disc 91 is pulled upward, closing push-pull cap 224. Syringe gripping arms 78 are also mounted to grooved block 400 such that the syringe body is pulled upward or downward in the same magnitude as slide disc 91 and nozzle 90 of push-pull cap 224 such that a connection between the syringe S and nozzle 90 is constantly maintained until push-pull cap 224 is closed and the syringe S is removed from the filler. For filling operations not involving a push-pull cap 224, grooved block can be articulated out of the way and air cylinder 401 will hold syringe gripping fingers 78 in a stationary position relative to yoke 82.

Figure 42:
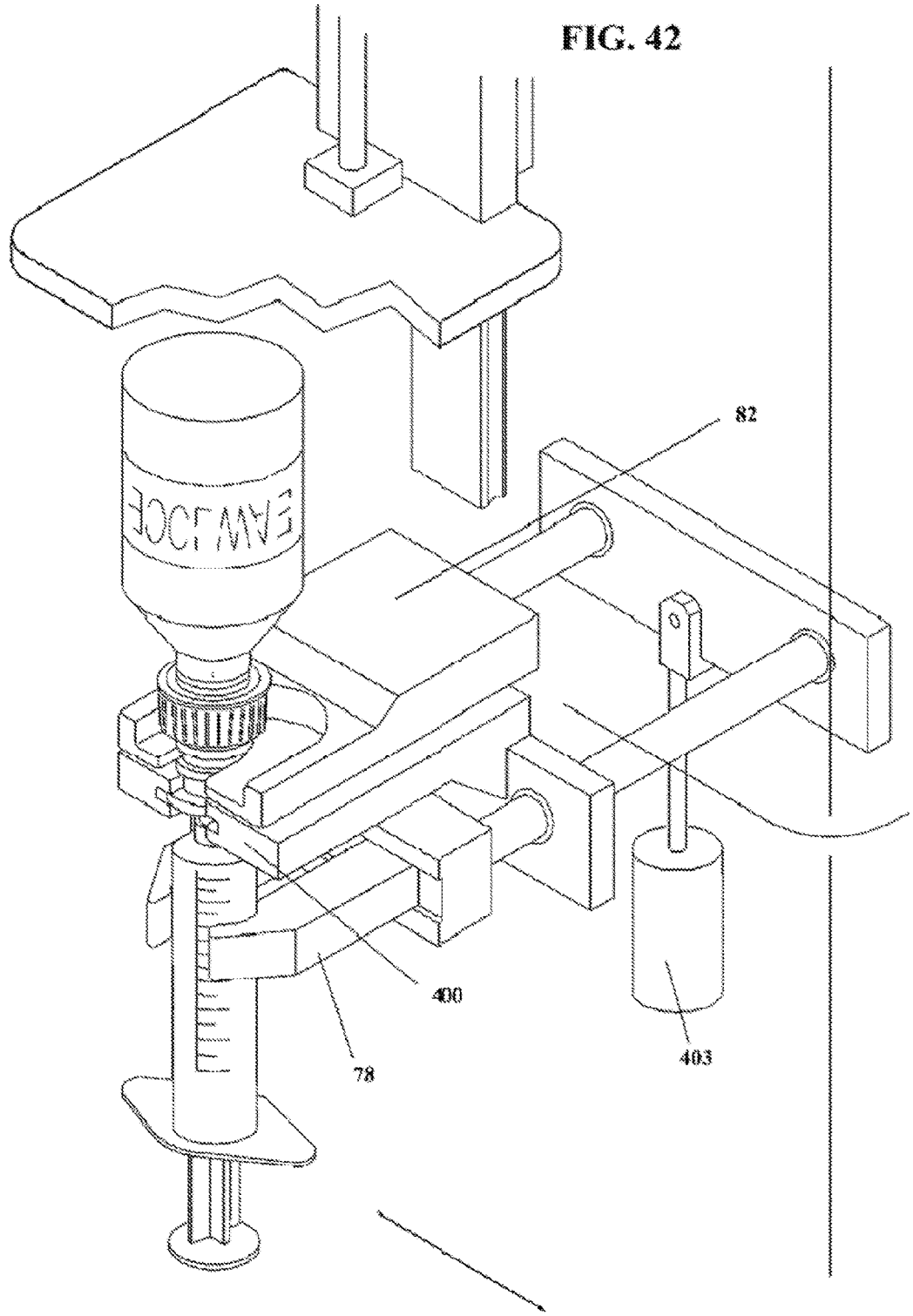
FIG. 42 is an enlarged perspective view of the actuation mechanism for filling station 5 comprising a grooved block 400 for actuating push-pull adapter cap 224 according to another embodiment of the present invention

In a second embodiment, shown in FIG. 42, the operation of grooved block 400 and its interface with slide disc 91 and syringe gripping fingers 78 is the same as described above. However, horizontal air cylinder 401 is replaced by vertical air cylinder 403 which moves grooved block 400 in a vertical direction directly without the need to utilize cam slots 402.

To enable the conversion between the use of tapered tip syringes (FIG. 38) and Luer lock syringes (FIG. 39) as is expected in the future for safety reasons, the entire system described herein may be modular to allow replacement of those modules designed specifically for tapered tip syringes as the Luer lock syringe rollout takes place.

FIG. 16A illustrates an shaker mechanism 820, which may be either integral to filling station 5 or a standalone unit, in which a single-speed motor 823 operates through an electronic clutch 827 to rotate cam wheel 824. In a preferred embodiment, filling station 5 comprises a base module containing syringe gripping fingers and a top module for supporting the medication container in an inverted position for filling the syringe. The top module may be shaker mechanism 820, or may be a module comprising medication container yoke 82A, 82B and/or self-centering jaws 82C and medication container platform 79 without any integral shaking mechanism, such as when a separate shaking mechanism 6 is used. Preferably, either of these top modules may be interchangeable based on design preference to allow for, i.e., an upgrade of the system from comprising an independent shaker mechanism 6 to integral shaking mechanism 820 or to allow the system to be adaptable to different needs. The top module and base module may be connected by a series of screws or any other non-permanent connection means known in the art.

For shaking mechanism 820, an eccentric pin 829 protruding from cam wheel 824 slidably engages a slotted block 830 as shown, and block 830 directly engages plate 821. When the motor 823 is activated it reciprocates plate 821, again shaking it and mixing the contents of medicine container 104 held therein.

FIG. 16B is a composite operational diagram illustrating the operation of the integral shaking mechanism 820 of FIG. 16A external of the syringe filling station 5. The plate 821 which supports the medicine container platform and syringe yoke is mounted on vertical slides 831. A slotted driven block 832 mounted on the plate 821 is engaged by eccentric pin 829. As the pin 829 rotates within the slot of block 832 the block 832 oscillates up and down. A single position clutch is mounted to the motor so that the slotted driven block as well as the entire platform stops at the same downward position all the time. The insets at top illustrate eccentric pin 829 engaging slotted driven plate 832 at top dead center (left), 90 degrees rotation, and bottom dead center.

FIG. 17 is a perspective view of an alternative remote medication container shake station 6 (i.e. not an integral part of the filling station 5 as seen in FIG. 2) for shaking the medicine container when required. The shake station 6 comprises a motor 62 with an offset trough 64 coupled to the rotary shaft 63. The trough 64 is an elongate arched platform for seating and centering medicine containers of various sizes. An upright post 65 abuts the base of the medicine container and self-centers it, allowing tightening of restraining straps 66. The straps 66 secure the medicine container along an oblique offset axis relative to that of the shaft 63. This particular configuration makes loading of the medicine container on the trough 64 very easy as seen in FIG. 17. When the motor 62 is activated the oblique rotation of the medicine container causes a centrifugal force that keeps the container against the stop post 64. Constrained by the bands 66 and post 65 the medicine container is effectively and efficiently shaken.

Figure 10:
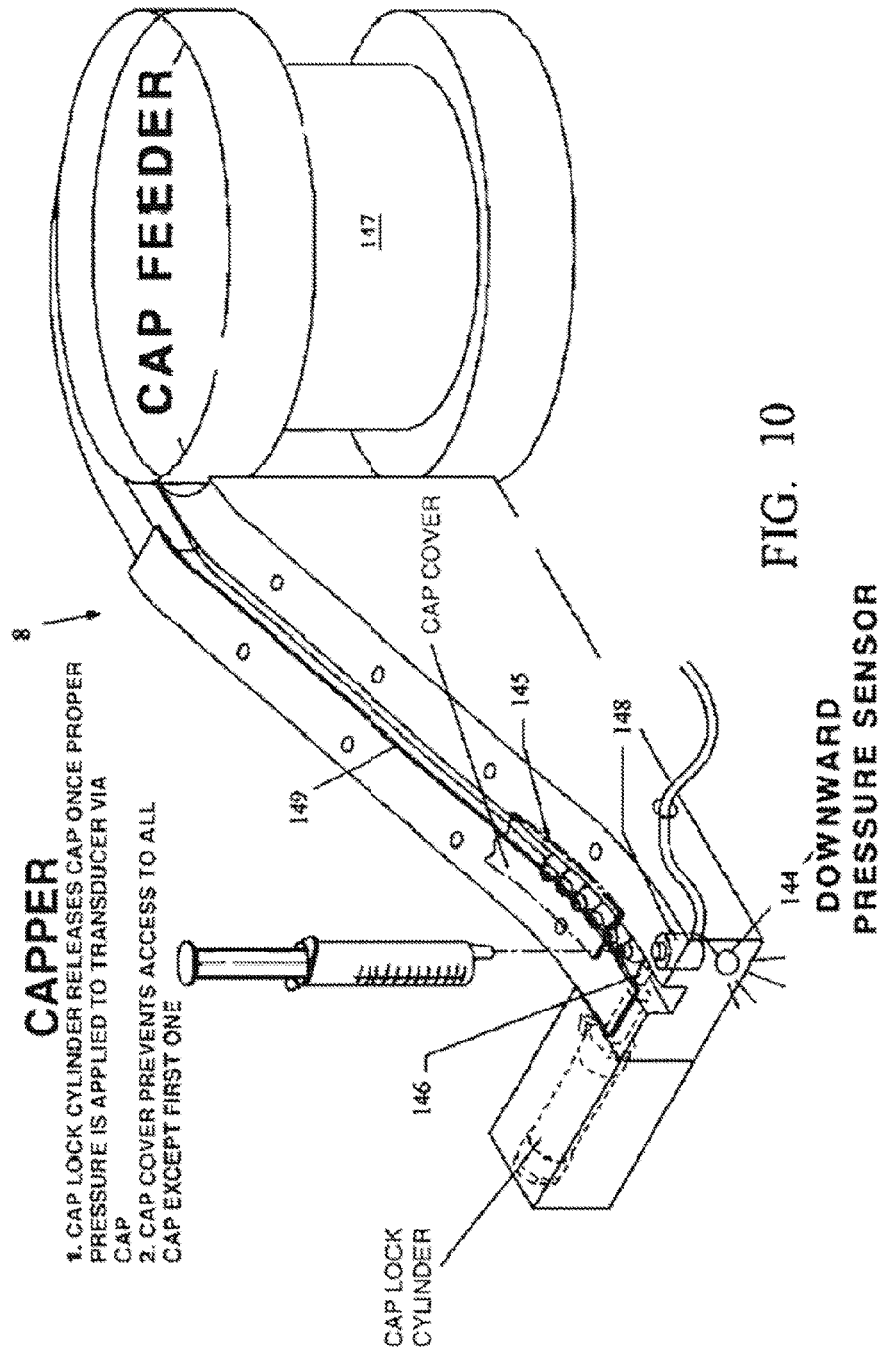
FIG. 10 is an enlarged perspective view of the semi-automated capping station 8.

The (optional) semi-automated capping station 8 (see FIG. 2) facilitates syringe cap placement on the open tip of the filled syringe S, fed from an inclined capping chute 149 (see FIG. 10). Referring back, FIG. 10 is an enlarged perspective view of the semi-automated capping station 8 with feeder bowl 147 and inclined capping chute 149. Feeder bowl 147 may be a centrifugal or vibratory bowl feeder as known in the art, sized for sorting and feeding syringe S caps single-file down inclined chute 149. A transparent plastic chute cover 145 may be provided overtop chute 149 to prevent access to all but the leading syringe S cap. It is rather common for pharmacy technicians to improperly cap filled syringes prior to administration, and this leads to leaking, contamination and other problems. A mechanism is herein provided to prevent this. When the leading syringe caps reach the bottom of chute 149 they come to bear against a cylinder rod 146 in a position directly overhead an electronic pressure transducer 148. Pressure transducer 148 is in communication with the OSPS central controller and registers the pressure of the syringe S nozzle pressing against transducer 148. A threshold pressure indicator LED 144 is mounted proximate transducer 148. To cap a syringe S the operator merely presses it down onto the leading cap until an acceptable threshold pressure is attained, and this is signaled by an LED indicator 144. At this point the cylinder rod 146 retracts allowing the operator to pull the capped syringe S out and free. The OSPS central controller preferably logs this in its track and trace database to provide an audit trail. This mechanism avoids any issues with improperly capped syringes.

During batch operation a series of syringes S to be filled with the same medicine may be queued and loaded in sequence by the operator for filling. When no more syringes are to be filled with the particular medicine, the local container 104 is returned to the medicine Storage facility 2 by the operator, who may retrieve another medicine and replace it in the syringe filling station 5 for the next medicine to be dispensed.

In a preferred embodiment, a 2D barcode on the syringe, medication container or cap may be scanned at each station described herein, and red/green lights or another visual or audible alert may indicate to the operator and/or to the software that a required protocol has not been followed for a given syringe, medication, or the like. For instance, a red light may be used to indicate, when a medication container is scanned at filling station 5, that the medication has expired, or to indicate, at the visual inspection station 9, that syringe S has not been filled to the proper fill volume as required for a given prescription. Scanning a 2D barcode at each station described herein would also permit the pharmacist or other operator to process medication or syringe/cap/container recalls more promptly and prevent any recalled items or medication from being provided to a patient. Recall information may be entered directly into the OSPS system when received by the hospital or pharmacy and the software may check every scanned item against the database of recalled medications and/or devices.

The 2D barcode described herein is preferably generated for syringe S at the syringe labeling station, and for the medication container at the Medication Container Orientation and Login Station (FIG. 2 (I)). Thus, in a preferred embodiment, the 2D barcode on the medication container is scanned at the Medication Container Orientation and Login Station (after it is generated) and the filling station 5, and the 2D barcode on the syringe S is scanned at the syringe labeling station (after it is generated), the filling station 5, syringe capping station 8, filled syringe inspection station 9, and bagging station 7.

Referring back to FIG. 2, after retrieval from the syringe filling station 5 and capping at syringe capping station 8, the operator places the syringe on inspection system 9 to cross check the weight and/or volume of the filled syringe against the expected weight/volume. The tare weight check is based on the known weight of the empty syringe and the volume of the prescribed medicine. The vision inspection entails an optical inspection (described above) based on the location of the syringe S plunger, the volume above the plunger and below the syringe tip, and bubble check. If the inspection station 9 determines that the syringe is filled to the correct volume and/or weight with an acceptable amount of bubbles, it will be accepted. Otherwise it will be rejected.

The labeled, filled and capped syringe is then bagged at bagger 7 for distribution to the patient, the bag itself being labeled in a similar manner as to the syringe. Bagger 7 may be any suitable commercially-available bagger with a network-capable bag printer, bag storage/dispenser, and heat seal assembly. A variety of automatic "tabletop bagger/printers" are available for this purpose.

Figure 11:
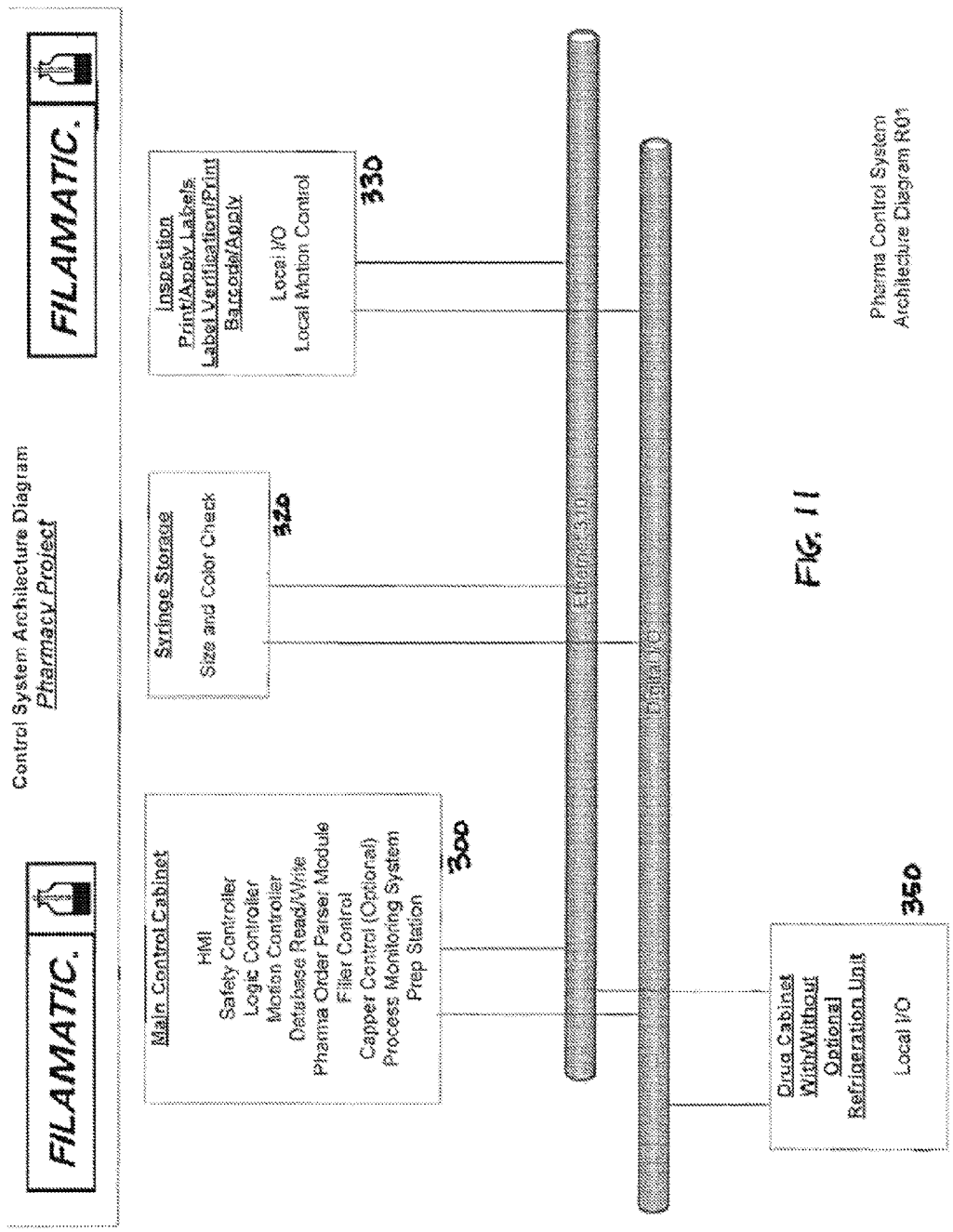
FIGS. 11 and 12 illustrate an exemplary control system architecture for the system 100 of FIGS. 2-10.
Figure 12:
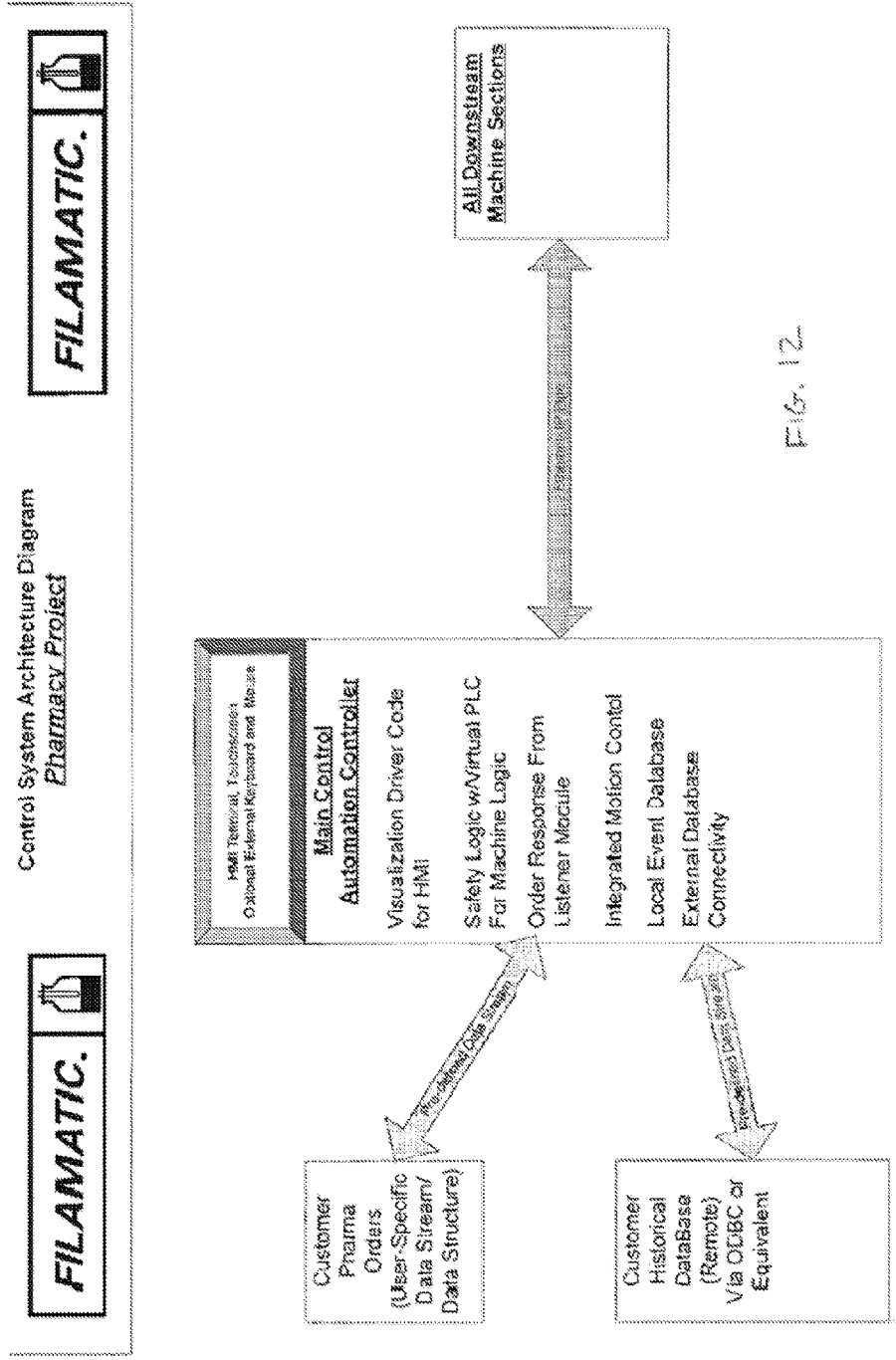

With reference to FIGS. 11 and 12, a control system architecture for the system 100 is disclosed in which a main controller 300 is provided in communication with a series of sub-controllers for one or more station steps via a communications backbone 310, in the depicted case, via Ethernet and local digital inputs and outputs. The main controller 300 is preferably a microprocessor based microcontroller or PC containing a processor core, memory, and programmable input/output peripherals. The controller contains a system safety controller, logic controller, top level motion controller and human-machine interface for interaction with a system operator. The main controller 300 further incorporates a database read/write module for interaction with a local or remote customer (patient) records database and local event database for managing downstream component operation. An order listener/parser module is provided for receiving orders from an external pharmacy/prescription entry and management system maintained by the institution. The parser can be custom formatted to discern and populate order information based on a user specified data stream and structure.

Sub-controllers are provided for all downstream machine sections such as Syringe Storage 320, Inspector/Labeler/verifier 330, and Medicine Library 350. The sub-controllers are each provided with a local input/output system and local motion controller integrated with the main controller 300 via the communications backbone 310. The main controller orchestrates the integration and operation of the downstream machine elements as described above and controls the overall operational mode of the system 100.

The local OSPS Computer may incorporate fill weight/volume adjustment software. Specifically, the vision inspection station 9 (FIG. 2) is networked to the Local OSPS Computer and may provide weight or volume feedback to automatically adjust the amount of liquid transferred into the oral syringe at servo-operated syringe filling station 5. The software determines if a syringe has too much or too little medicine in it. Any out-of-spec syringe will be rejected and the system will automatically queue a replacement utilizing information from the previously-rejected syringe.

Figure 13:
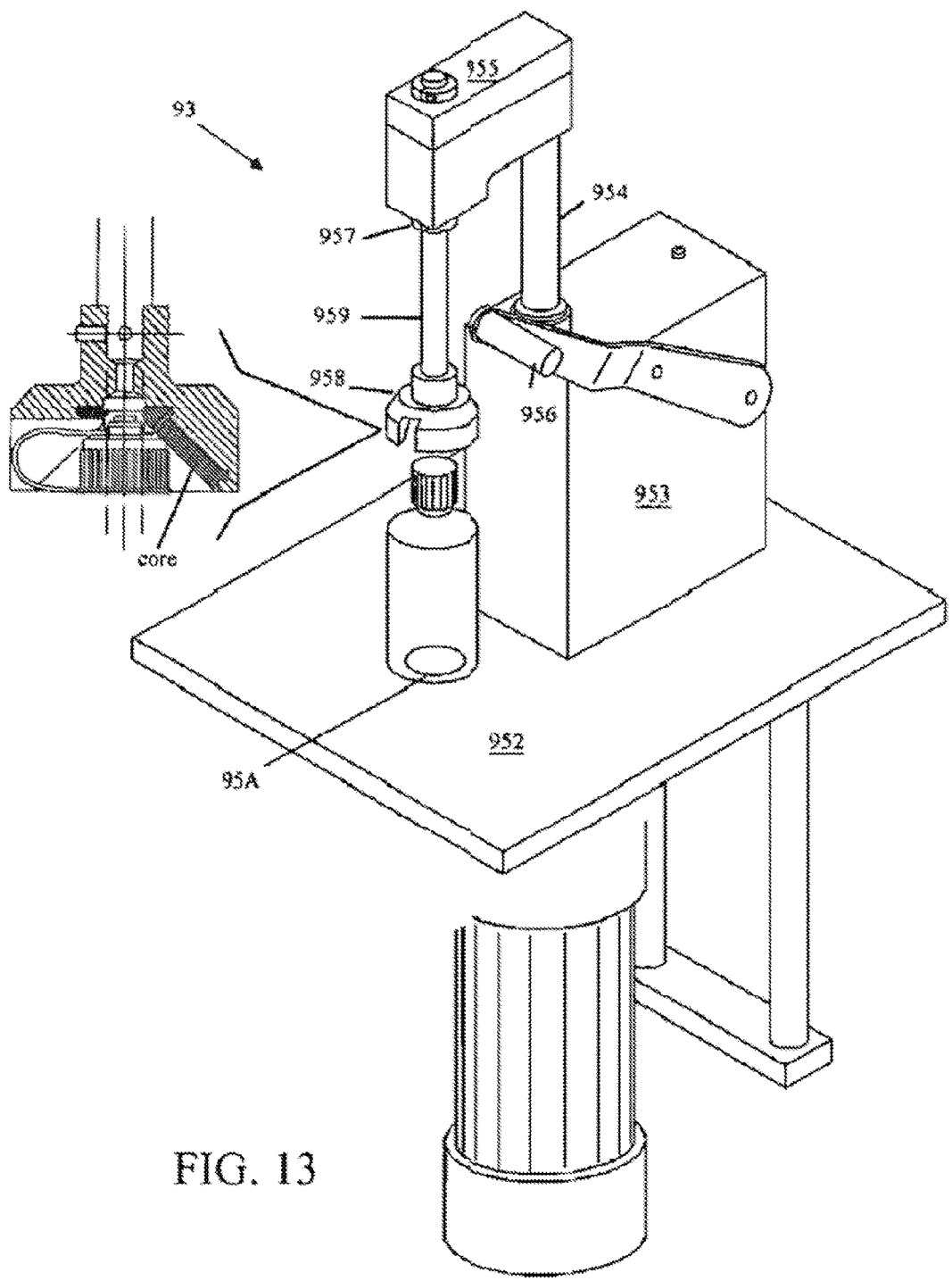
FIG. 13 is a perspective view of an exemplary capping/decapping station 93 resident at the Medication Container Orientation and Log-In Station.

FIG. 13 is a perspective view of an exemplary capping/decapping station 93, which comprises an elevated platform support surface 952 for stabilizing the medicine container. An optional container clamp (not shown) may be mounted on the support surface 952 for centering and constraining the medicine container. The container clamp may comprise a pair of opposing V-shaped clamps. An operator presses a "clamp" button and the opposing V-shaped clamps close around the container bottle. The V-shaped clamps may be mounted on low-friction slides so that any size bottle can be slid toward the center of the chuck. Although the clamps are mounted on low friction slides, they remain stationary to rotation. An articulating spindle assembly extends upward from a base 953 mounted on the support surface 952, the spindle assembly including a vertical piston 954 extendable/retractable from base 953 and a horizontal mast 955 extending from piston 954. The mast 955 contains a motor which drives a vertical spindle 959. A manual lowering arm 956 is geared to the piston 954 for piston extension/retraction from base 953, thereby allowing an operator to raise or lower spindle 959 manually. A pressure sensor 957 is mounted to the spindle 959 (or internal to the mast 955 for sensing the downward pressure. A chuck 958 is mounted at the lower end of the spindle 959. As seen in the inset (at left), the chuck 958 is preferably formed with a hard outer shell (e.g., stainless steel) and a molded plastic core placed inside, the core defined by a conical interior surface with an elastomeric inner lining. An elastomer such as polyurethane or equivalent resin can be poured around the interior of the core to form the elastomeric lining. A lateral slot enters the interior of the chuck 958. This chuck 958 is designed to fit all caps ranging from 18 mm to 38 mm in diameter. Due to its conical interior and elastomeric inner lining, downward pressure onto the container cap causes a non-slip, gripping action. The slot accommodates certain container caps which have a tethered closure feature. The tether is free to protrude and will not cause interference between the chuck 958 and cap. This capping/decapping station 93 enables the medicine caps to be loosened from their containers mechanically without the need for an operator to exert strong hand pressure. The system is capable of loosening caps as well as applying torque to seat them. In operation, the medicine container is placed on the support surface 952, and the operator centers the container either with the optional holding clamp or by hand, and if to cap a pre-labeled container/syringe interface is placed on the container. Upon moving the manual lowering arm 956 forward, the piston 954 extends from base 953, thereby a lowering spindle 959. The chuck 958 descends into contact with the container/syringe interface to tighten it, or into contact with the manufacturer cap if decapping is desired. Once the chuck 958 descends onto the cap and downward force is applied the pressure sensor 957 begins to compress and in doing so, signals the motor to start. This avoids inadvertent rotation of the elastomeric chuck 958 in advance of contacting the cap which may cause abrasion and emit particles of the elastomer in the vicinity of the work area. The scanner 95A may be mounted beneath the platform support 952 to read the medicine container's 2D barcode from beneath. Preferably, the scanner 95A is synchronized via the OSPS computer such that the first time it reads a particular barcode the spindle 959/motor turn in the counter-clockwise (cap removal) direction. Conversely, the second time scanner 95A reads that particular barcode the spindle 959/motor turn in the clockwise (cap tightening) direction. The assembled medicine container and container/syringe interface can be slid out and removed.

Figure 14:
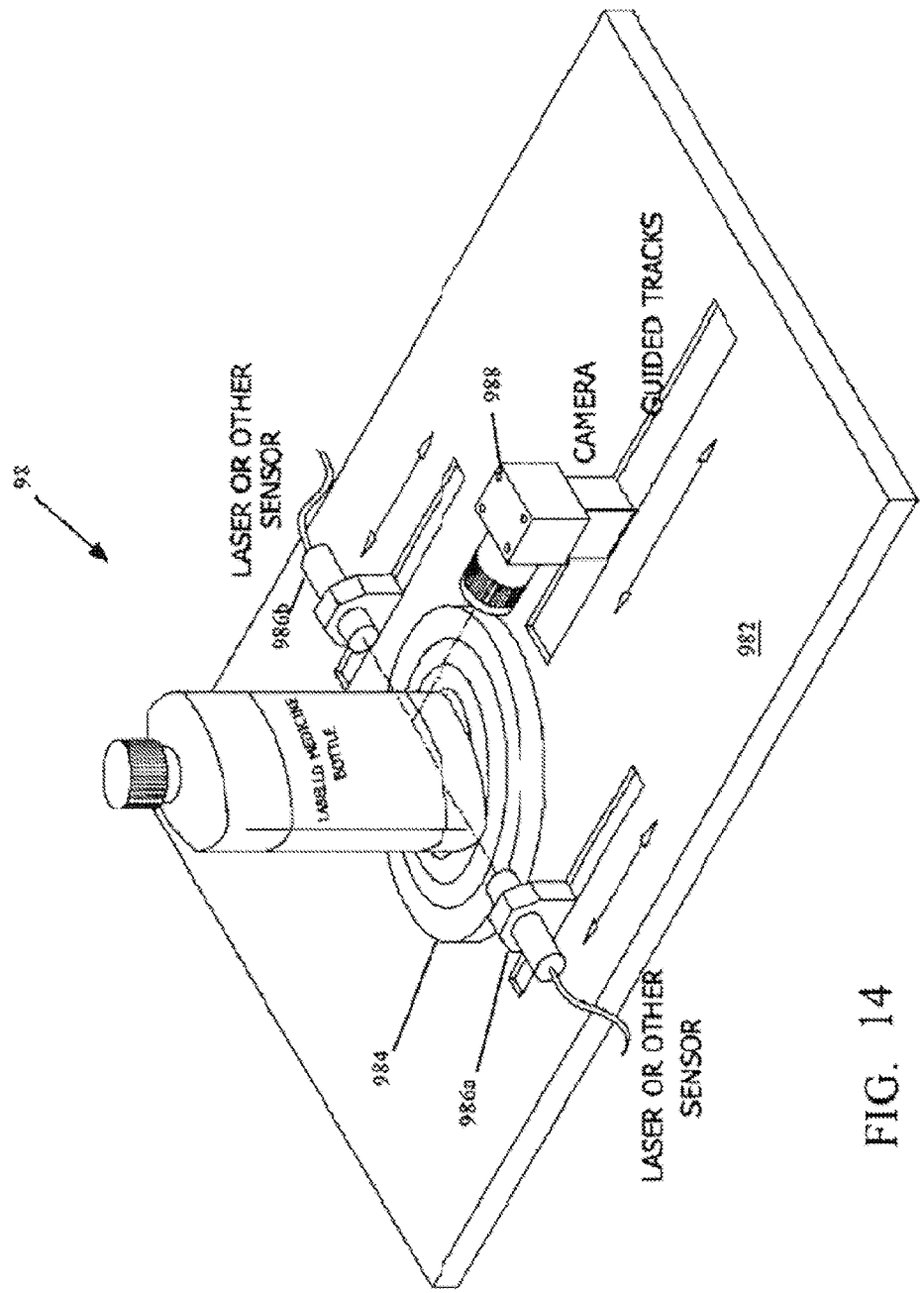
FIG. 14 is a perspective view of the optional label photographing station 98 resident at the Medication Container Orientation and Log-In Station.

FIG. 14 is a perspective view of the label photographing station 98 resident at the Medication Container Orientation and Log-In Station. The label photographing station 98 is employed for the purpose of photographing the entire medicine container's label for archival purposes (to retain a record of the medication used to fill a specific prescription). In some cases, the barcode scan from scanner 95A alone will be insufficient to identify details such as medicine concentration, expiration, handling and other precautions relative to the medication. The label photographing station 98 comprises a circular table 984 rotatably seated atop a support surface 982. A camera 988 is oriented directly toward a focal point centrally atop the table 984, and a pair of opposing sensors 986*a*. 986*b* is indirectly aimed from the sides toward that same focal point. The camera 988 and sensors 986*a*, 986*b* are all mounted on a common undercarriage via struts that pass through tracks in the table 984. This allows the camera 988 and sensors 986*a*, 986*b* to translate in unison along the tracks in the table 984. The undercarriage is servo-driven (or otherwise adapted for controlled translation) under control on the OSPS Computer, in accordance with feedback from sensors 986*a*, 986*b*. The medicine container may be manually placed anywhere atop the table 984, and the OSPS Computer will drive the undercarriage until the sensors 986*a*, 986*b* align with the surface of the medicine container. The sensors 986*a*, 986*b* track the surface of the container and travel with that focal surface, along with the camera 988. This positions the camera 988 at exactly the proper focal distance regardless of container position, and maintains the optimum focal distance from label to camera 988 despite a variety of sizes and shapes of medicine containers.

Process and System Configuration Variations Specific to Container/Syringe Interfaces Filling a Syringe Using a Standard Commercially Available "Baxa" Cap 214 (See FIG. 5)

The standard commercially available Baxa™ cap 214 comprises a female threaded cap to fit over medication containers and is available in sizes to accommodate most medication containers. Baxa™ cap 214 enables an oral syringe to enter its center hole and withdraw an amount of liquid from the medication container while the medication container is positioned upside down. For the syringe to be removed from the medication, both syringe and medication container must be up-righted. Once up-righted, the syringe S can be removed from the up-righted medication bottle with no leakage. If the medication bottle requires shaking at any given time, it can be done manually or in a separate shaker (FIG. 17) by closing the tethered cap and fastening the bottle into the shaker tray. The sequence of operation is as follows:

a. Remove original cap (FIG. 18A).
b. The Baxa™_cap 214 is applied onto the neck of the container (FIG. 18B).
c. The syringe S is inserted into the Baxa™ cap 214. (FIG. 18C).
d. The medication container and the syringe S combination are rotated up-side-down. (FIG. 18D).
e. Both the medication container and the inserted syringe S are then inverted and placed into the yoke 82A (FIG. 18E) of the filling station 5 (see FIG. 7A).
f. The Syringe is clamped by the filler finger grippers 78 and a platform 79 (FIG. 18F) lowers to the bottom of the over turned medication bottle and applies downward pressure to the bottle as it is supported by the yoke 82 (see FIG. 7D).
g. Now the syringe gripping arms 110, 111 and 112 engage the syringe S plunger, prime and pull the plunger to the exact fill dose (see FIG. 7A).
h. Remove medication container and the syringe S combination and extract syringe S.

Filling an Oral Syringe Using an OEM-Baxa™ Cap with Self Sealing Valve 216 (See FIG. 5)

As described above the standard Baxa™ cap is modified to incorporate a self-sealing valve 216 which enables an oral syringe S to enter its center hole while the medication container is positioned upside down without leaking. The Baxa™ Cap with Self Sealing Valve 216 also allows for syringes to be removed after filling without removing the medication container from the filing station 5 (see FIG. 2 III) and repeat the filling of subsequent syringes S when a quantity of syringes are to be filled with the same medication. In the event of a scheduled shaking requirement, after a specified amount of time, the system can shake the medication without removing it from the filling station (see FIG. 16A). Frequency and strokes per minute are preprogrammed into the system. The sequence of operation is as follows:

a. Remove original cap (FIG. 19A).
b. Baxa™ Cap with Self Sealing Valve 216 is tightened onto the neck of the container (FIG. 19B).
c. Medication container is turned upside down (see FIG. 19C). The neck of the container is placed into a slotted yoke 82B or the self-centering spring loaded jaws 82C (FIG. 7B). Since the neck of the container is held on center by the slotted yoke 82B, or the self-centering spring loaded jaws 82C the opening to the Baxa Cap with Self Sealing valve 216 will be properly aligned with the syringe S and the mechanism for filling the syringe S by pulling the syringe plunger downward. (see FIG. 19C).
d. The medication container platform 79 is lowered to securely hold the medication container in place onto either the Yoke 82A (see FIG. 19C).
e. If the medication container needs to be shaken, it is shaken at the programmed speed, duration and frequency (see FIG. 16A).
f. The syringe S tip is inserted up, into the Baxa Cap with Self Sealing Valve opening 216.
g. The syringe S is filled by the syringe gripping arms 110, 111 and 112 which engage the syringe S plunger, prime and pull the plunger to the exact fill dose (see FIG. 19D).
h. The syringe is unclamped by the filler finger grippers 78 and the syringe is removed from the Medication container (FIG. 19D).
i. If additional syringes S need to be filled with the same medication, the process is repeated.
j. When all syringes have been filled with the medication, the platform 79 rises and the medication bottle is removed.
k. This process continues until all syringes for that prescription production run have been filled.

Filling a Syringe Using a PIBA (No Valve) 210 (See FIG. 5)

Figure 20:
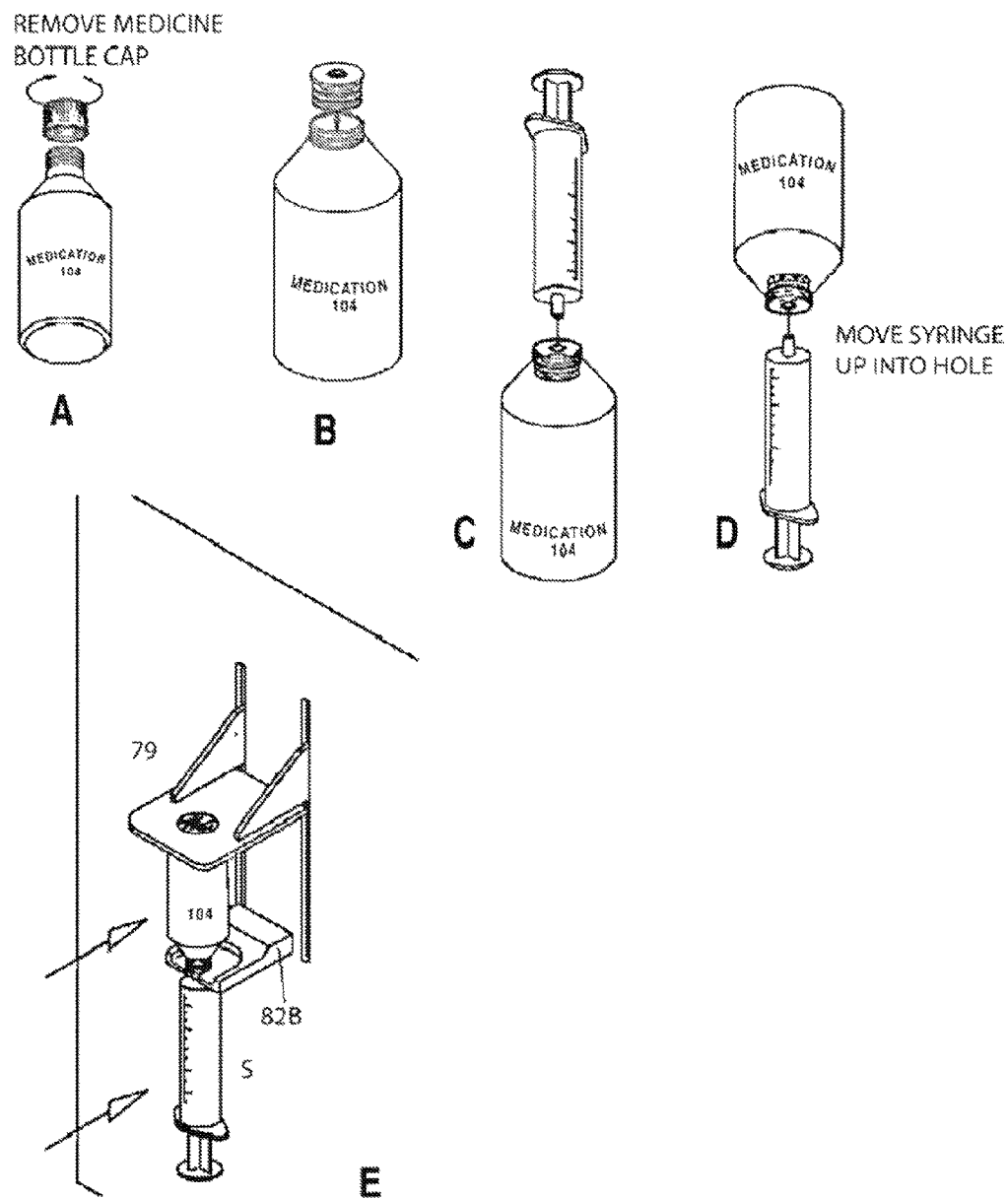
FIG. 20 is a sequential illustration of the process for filling a syringe S using a press in bottle adapter (PIBA) (no valve) 210.

If a medication container with valveless PIBA 210 requires shaking, this must be done either manually or with the optional free standing shaker (FIG. 17). This must be repeated every time shaking is required regardless of whether the same medication is being filled into multiple syringes. The original cap must be placed over the Medication bottle and its press-in insert, during storage, to ensure cleanliness. The sequence of operation is as follows:

a. Remove medicine bottle cap (FIG. 20A).
b. The valveless PIBA 210 is inserted into the neck of the container (FIG. 20B).
c. The syringe S is inserted into the valveless PIBA 210 (FIG. 20C).
d. The medication container and the syringe S combination are rotated up-side-down. (FIG. 20D).
e. The medication container and syringe S combination are placed into the filling station 5 via Yoke 82B or Self-Centering jaws 82C (FIG. 20E).
f. After filling, the medication container and syringe S combination are removed from the filling station 5.
g. The medication container and syringe S combination are then up-righted (FIG. 20C), and the filled syringe is then removed from the medication container.

Filling a Syringe S Using a PIBA (with Valve) 212/225 (See FIGS. 5 and 44)

The Self Sealing PIBA Insert 212 is pressed into the neck opening of a medication container and enables an oral syringe S to enter its center hole and withdraw an amount of liquid from the medication container while the medication container is positioned upside down. In addition, it also enables the syringe to be removed without leaking and the medication container to be shaken at the fill station 5 (FIG. 2 III), while it is positioned upside down and without leaking. The self sealing PIBA insert 212 also allows for syringes S to be removed after filling without removing the medication bottle and repeat the filling of subsequent syringes S in cases where a quantity of syringes S are to be filled with the same medication. In the event of a scheduled shaking requirement, after a specified amount of time, the system can shake the medication without removing it from the filling station (see FIG. 16A). Frequency and strokes per minute are pre-programmed into the system. The sequence of operation is as follows:

a. Remove medicine bottle cap (FIG. 21A).
b. The self sealing PIBA insert 212 is inserted into the neck of the container (FIG. 21B).
c. The medication container is turned upside down (FIG. 21C).
d. The neck of the container is placed into the Self Centering Jaws 82C or Yoke 82B (FIG. 21D) Since the neck of the container is held on center by the yoke 82B or Self Centering Jaws 82C, the opening to the self sealing PIBA insert 212 will be properly aligned with the syringe S and the mechanism for filling the syringe.
e. The medication container platform 79 is lowered to securely hold the medication container in place on the Self Centering Jaws 82C (see FIG. 21D).
f. If the medication container needs to be shaken, it is shaken at the programmed speed, duration and frequency (see FIG. 16A) while still held in the filling station 5.
g. The syringe S is inserted into the self sealing PIBA insert 212 opening (FIG. 21E).
h. The syringe is filled.
i. The syringe is removed from the medication container.
j. If additional syringes need to be filled with the same medication, the process is repeated while the medication bottle remains held within the filler.
k. When all syringes S have been filled with the medication, the medication container is removed.
l. This process continues until all syringes for that prescription production run have been filled.

Filling an Oral Swine Using a Valved Self-Sealing Two Piece Cap with Common Outer Diameter 220, 221 (See FIG. 5)

As described above, the cap comprises a common outer diameter portion and either an insertable or integrally-formed self-sealing insert which enables an oral syringe S to enter its center hole while the Medication container is positioned upside down without leaking. The valved self-sealing one or two-piece cap 220, 221 also allow syringes to be removed after filling without removing the medication container from the filing station 5 (see FIG. 2 III) and repeat the filling of subsequent syringes S when a quantity of syringes are to be filled with the same medication. In the event of a scheduled shaking requirement, after a specified amount of time, the system can shake the medication without removing it from the filling station (see FIG. 16A). Frequency and strokes per minute are pre-programmed into the system. The sequence of operation is as follows:

a. Remove original cap (FIG. 19A).
b. Valved self-sealing one or two piece cap 220, 221 is tightened onto the neck of the container (FIG. 19B).

c. Medication container is turned upside down (see FIG. 19C). The neck of the container is placed into a slotted yoke 82B or the self-centering spring loaded jaws 82C (FIG. 7B). Since the neck of the container is held on center by the slotted yoke 82B, or the self-centering spring loaded jaws 82C the opening to the cap 220, 221 will be properly aligned with the syringe S and the mechanism for filling the syringe S by pulling the syringe plunger downward (see FIG. 19C).
d. The medication container platform 79 is lowered to securely hold the medication container in place onto either the Yoke 82A (see FIG. 19C).
e. If the medication container needs to be shaken, it is shaken at the programmed speed, duration and frequency (see FIG. 16A).
f. The syringe S tip is inserted up, into the cap opening 220, 221.
g. The syringe S is filled by the syringe gripping arms 110, 111 and 112 which, in concert with arm 128, engage the syringe S plunger, prime and pull the plunger to the exact fill dose (see FIG. 19D).
h. The syringe is unclamped by the filler finger grippers 78 and the syringe is removed from the Medication container (FIG. 19D).
i. If additional syringes S need to be filled with the same medication, the process is repeated.
j. When all syringes have been filled with the medication, the platform 79 rises and the medication bottle is removed.
k. This process continues until all syringes for that prescription production run have been filled.

Filling a Syringe S Using a Push-in Tip 223 for Interfacing with Luer Lock Oral Syringes (See FIGS. 27-28)

The push-in tip 223 is pressed into the nozzle opening of a Baxa™ or Baxa™-equivalent manufacturer-supplied medication container cap (FIG. 27) or PIBA cap (FIG. 28). If a medication container with push-in tip 223 requires shaking, this must be done either manually or with the optional free standing shaker (FIG. 17). This must be repeated every time shaking is required regardless of whether the same medication is being filled into multiple syringes. A protective cap 223C must be placed over the Medication bottle during storage, to ensure cleanliness. The sequence of operation is as follows:
a. The push-in tip 223 is inserted into the nozzle opening of a Baxa™ or Baxa™-equivalent manufacturer-supplied medication container cap (FIG. 27) or PIBA cap (FIG. 28).
b. The syringe S is inserted into the push-in tip 223 (FIGS. 27C and 28C).
c. The medication container and the syringe S combination are rotated up-side-down.
d. The medication container and syringe S combination are placed into the filling station 5 via Yoke 82A, Yoke 82B or Self-Centering jaws 82C.
e. After filling, the medication container and syringe S combination are removed from the filling station 5.
f. The medication container and syringe S combination are then up-righted and the filled syringe is then removed from the medication container.

Filling a Syringe S Using a Push-Pull Cap 224 for Use with a PIBA or Baxa™ or Baxa™-Equivalent Medication Container Cap and Luer Lock Oral Syringe (FIGS. 29-32)

The push-pull cap 224 is inserted over the nozzle of a Baxa™ or Baxa™-equivalent manufacturer-supplied medication container cap (FIG. 29) or into the nozzle of a PIBA (FIG. 31). Alternately, push-pull cap 224 is made integral with either a Baxa™ or Baxa™-equivalent manufacturer-supplied medication container cap (FIG. 30) or a PIBA (FIG. 32) enabling the integral cap to be screwed directly onto or pushed directly into the neck opening of a medication container, respectively. All of these arrangements enable an oral syringe S to enter the center hole of cap 224 and withdraw an amount of liquid from the medication container while the medication container is positioned upside down. In addition, they also enables the syringe to be removed without leaking and the medication container to be shaken at the fill station 5, while it is positioned upside down and without leaking. The push-pull cap 224 also allows for syringes S to be removed after filling without removing the medication bottle and repeat the filling of subsequent syringes S in cases where a quantity of syringes S are to be filled with the same medication. In the event of a scheduled shaking requirement, after a specified amount of time, the system can shake the medication without removing it from the filling station (see FIG. 16A). Frequency and strokes per minute are pre-programmed into the system. The sequence of operation is as follows:
a. For integral push-pull caps 224, remove medicine bottle cap; for separable push-pull caps 224, insert push-pull cap 224 directly over or into a Baxa™ or Baxa™-equivalent manufacturer-supplied medication container cap, respectively.
b. The medication container is turned upside down.
c. The neck of the container is placed into the filling station.
d. The medication container platform 79 is lowered to securely hold the medication container in place at the filling station 5.
e. If the medication container needs to be shaken, it is shaken at the programmed speed, duration and frequency (see FIG. 16A) while still held in the filling station 5.
f. The syringe S is inserted into the nozzle 90 of push-pull cap 224.
g. The syringe is filled.
h. The syringe is removed from the medication container.
i. If additional syringes need to be filled with the same medication, the process is repeated while the medication bottle remains held within the filler.
j. When all syringes S have been filled with the medication, the medication container is removed.
k. This process continues until all syringes for that prescription production run have been filled.

In the future, for drug anti-counterfeiting purposes, medication containers may include 2D barcodes applied to them by the manufacturers with unique ID numbers and other data. Consequently, medication containers may be supplied to the pharmacies with a pre-applied 2D barcode providing a unique ID number and other medication-related data. When this is the case, the system does not require that a special barcode label with information on the medication be generated and attached to the base of the medicine container. The medication Container Login & Orientation Station 1 may be bypassed and/or omitted entirely, and the manufacturer's barcode on the container is utilized. A track, trace and control system is similar to the OSPS previously described is provided. The objective of the simplified syringe filling and labeling system is to ensure that the proper medication is filled into the syringe and that the syringe is labeled correctly. If an optional weight check or volume check station is utilized, the proper amount of fill can be verified. The system minimizes downtime as well as processing time to take and fill orders, and is easy to clean and capable of maintaining an environment free from cross contamination. The system is open and accessible and allows interaction and oversight by a human operator at multiple points in the operation. Moreover, it is modular and permits a differing and upgradeable level of operator participation (from a syringe filling device only to a semi-automated combination of labeling, filling, inspection, capping, and/or bagging functionality) based on the need of the individual institution.

It should now be apparent that the above-described system is driven by prescription orders in a just-in-time environment, manages all the various prescription containers containing the pharmaceuticals to be dispensed, as well as variously-sized oral syringes, to automatically converge them and orient, fill, label and cap each syringe and fully verify its work as it proceeds in order to avoid medication errors in the process. The pharmacy automation system for oral syringes substantially improves the pharmacist and technician productivity and maintains an environment free from cross contamination.

In all the above-described embodiments, the entire system is modular and permits an upgradeable core based on the need of the individual institution. Optional system components such as the label photographing station 98 resident at the Medication Container Orientation and Log-In Station may be purchase and added to the system subsequent to the original purchase.

Having now fully set forth the preferred embodiment and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims and may be used with a variety of materials and components. This application is therefore intended to cover any variations, uses, or adaptations of the invention using its general principles. Further, this application is intended to cover such departures from the present disclosure as come within known or customary practice in the art to which this invention pertains.

STATEMENT OF INDUSTRIAL APPLICABILITY

In hospitals around the world, many types of liquid medications are necessarily administered orally to patients who cannot or are unwilling to receive the same medications by injection. Thus, for a typical hospital, it may be necessary to fill hundreds or thousands of oral prescriptions each year by removing the prescribed amount of liquid medication from a bulk liquid medication container and placing it into an oral syringe in a clean environment. Filling an oral syringe prescription incorrectly, by placing the wrong medication, the wrong dosage, by mislabeling the syringe such that it is received by the wrong patient, etc., can be harmful or even fatal to the patient who receives the medication (and to the patient who does not receive the proper medication). In addition, it is often necessary to rapidly fill prescriptions for oral syringes to promptly treat patients needing the liquid medication. A system for quickly and accurately filling several oral syringes in a hospital setting would greatly increase patient safety and treatment quality. The present invention is a system and methods for the semi-automated filling, bagging, and labeling of several oral syringe prescriptions, wherein each step in the filling, bagging and labeling procedure is performed at least in part by, and monitored and tracked by, a device controlled by a programmable controller which may interface with a hospital prescription database to further eliminate errors in filling oral syringes.

We claim:

1. A system for semi-automated filling of syringes with medicines from containers, said syringes being of various sizes and types all having a barrel, an annular flange encircling said barrel, a plunger slideably engaged in said barrel, and a flange at distal end of said plunger, and said plurality of containers of medicines being of various sizes and types, the system comprising:
   a programmable controller including software for controlling said system;
   a container of medicine having an annular body and an aperture into said body for accepting a syringe nozzle;
   a filling station, comprising:
      a syringe loading station for loading of a syringe,
      a container loading station for manual loading said container, said container loading station including a gripper for gripping said container; and
      a plurality of arms for manipulating said syringe when in said filling position, said plurality of arms including at least a first arm and second arm both terminating in a forked end for engaging the syringe, each arm being independently servo-controlled and articulating along an axis, said first arm and said second arm being adapted to withdraw the plunger of said syringe to fill said syringe with medicine;
      wherein said second arm terminates in one or more right-angle plates each having a transverse curvilinear notch defining said forked-end terminus.

2. The system for semi-automated filling of syringes according to claim 1, further comprising:
   an extended bit located beneath said fixture for mounting one of said bulk medicine containers in an inverted filling position, said bit containing an annular cutout through its entire height, said cutout being defined by an inner wall, said inner wall comprising an annular groove sized to hold a slide ring of
   a push-pull medication container cap; and
   an actuator operatively connected to said bit for controlling the vertical movement of said bit;
      wherein said operation of said actuator controls the opening and closing of said push-pull valve.

3. The system for semi-automated filling of syringes according to claim 1, wherein said second arm extends vertically from a horizontal base member of said filling station.

4. The system for semi-automated filling of syringes according to claim 3, wherein said second arm extends through fluid-sealed bushings at an attachment point between said horizontal base member and said second arm.

5. The system for semi-automated filling of syringes according to claim 3, wherein:
   said first arm comprises two right-angle plates each having a transverse curvilinear notch for gripping a top and a bottom of said annular flange encircling said barrel of said syringe; and said second arm comprises one right-angle plate having a transverse curvilinear notch for gripping said flange at said distal end of said plunger of said syringe.

6. The system for semi-automated filling of syringes according to claim 1, wherein said gripper for gripping said container is a pair of self-centering jaws, said jaws comprising a pair of spring-loaded jaws slidably mounted on a ball-slide track for slidable separation.

7. The system for semi-automated filling of syringes according to claim 1, wherein said programmable controller is in communication with a hospital computer system so that when an electronic prescription is entered into in said hospital computer system for a dose of prescription medicine to be administered via an syringe, data is transmitted from said electronic prescription to said system for automatically filling an syringe with said dose of prescription medicine.

8. The system for semi-automated filling of syringes according to claim 1, wherein said filling station comprises a container holding yoke mounted to said filling station.

9. The system for semi-automated filling of syringes according to claim 8, wherein said container holding yoke is removably mounted.

10. The system for semi-automated filling of syringes according to claim 8, further comprising a plurality of differently-sized container holding yokes selectably mounted to said filling station.

11. The system for semi-automated filling of syringes according to claim 8, further comprising a pusher platform opposed to said container holding yoke for bearing against a bottom side of a medicine container to hold it captive.

12. The system for semi-automated filling of syringes according to claim 11, wherein said pusher platform has a window through it.

13. The system for semi-automated filling of syringes according to claim 12, further comprising a scanner at said filling station.

14. The system for semi-automated filling of syringes according to claim 13, wherein said scanner is mounted at said filling station proximate said window for scanning a label on said medicine container through the window of said pusher platform.

15. The system for semi-automated filling of syringes according to claim 1, further comprising a shaker for shaking said medicine container.

16. The system for semi-automated filling of syringes according to claim 15, wherein said shaker is integral to the gripper of said container loading station and is operatively connected to said programmable controller for receiving instructions from said controller regarding shake duration, intensity, and intervals.

17. The system for semi-automated filling of syringes according to claim 15, wherein said shaker is a stand-alone shaking station.

18. The system for semi-automated filling of syringes according to claim 15, wherein said shaker is integral to said filling station.

19. The system for semi-automated filling of syringes according to claim 1, wherein said container of medicine is configured with a cap having a push-pull valve.

20. A system for semi-automated filling of syringes with medicines from containers, said syringes being of various sizes and types all having a barrel, an annular flange encircling said barrel, a plunger slideably engaged in said barrel, and a flange at distal end of said plunger, and said plurality of containers of medicines being of various sizes and types, the system comprising:
  a container loading station for manual loading of said medication container; and
  a syringe loading station for loading of said syringe;
  wherein said syringe loading station comprises a plurality of arms for manipulating said syringe when in said filling position, said plurality of arms including at least a first arm and second arm, said first arm comprising two right-angle plates each having a transverse curvilinear notch for gripping a top and a bottom of said annular flange encircling said barrel of said syringe, and said second arm comprising one right-angle plate having a transverse curvilinear notch for gripping said flange at said distal end of said plunger of said syringe.

21. A method for semi-automated filling of syringes with medicines from containers, said syringes being of various sizes and types all having a barrel, an annular flange encircling said barrel, a plunger slideably engaged in said barrel, and a flange at distal end of said plunger, and said plurality of containers of medicines being of various sizes and types and bearing a manufacturer barcode label, the method comprising the steps of:
  logging a plurality of bulk medicines in containers by the substeps of,
    adapting a selected container of medicine for insertion of a nozzle of a syringe;
    scanning the manufacturer barcode label for medicine information, and
    automatically printing a new unique barcode label and attaching said barcode label to said medicine container;
  compiling a plurality of syringe prescriptions to be filled;
  sorting said plurality of syringe prescriptions into batches, each batch comprising a specified type of medicine;
  retrieving a medicine container containing said specified type of medicine;
  scanning the attached new unique barcode label to confirm that said retrieved medicine container contains said specified type of medicine;
  guiding an operator to retrieve a syringe;
  automatically printing a label for the syringe and attaching said label to the syringe;
  scanning said printed syringe label;
  loading said retrieved syringe and said retrieved medicine container into said fill station;
  automatically filling the syringe from medicine in said medication container by withdrawing a plunger of said syringe.

22. The method for semi-automated filling of syringes according to claim 21, further comprising a step of inspecting the filled syringe for one of fill weight or volume.

23. The method for semi-automated filling of syringes according to claim 21, further comprising a step of automatically labelling a package for packaging of said filled syringe.

24. The method for semi-automated filling of syringes according to claim 23, wherein said step of automatically labelling a package comprises printing an indicia on said package.

25. The method for semi-automated filling of syringes according to claim 24, further comprising a step of scanning the indicia for integrity.

26. The method for semi-automated filling of syringes according to claim 23, further comprising a step of placing the filled syringe in the package and sealing the package.

27. The method for semi-automated filling of syringes according to claim 21, wherein said step of automatically filling the syringe comprises automatically shaking said container for a prescribed duration and intensity at prescribed intervals.

28. The method for semi-automated filling of syringes according to claim 21, wherein said step of automatically filling the syringe with medicine in said medication container by withdrawing a plunger of said syringe comprises automatically withdrawing a plunger of said syringe with a servo-controlled arm for manipulating said plunger.

29. The method for semi-automated filling of syringes according to claim 28, wherein said servo-controlled arm further comprises a plurality of servo-controlled arms further including at least a first arm and second arm both terminating in a forked end for engaging the syringe, each arm being independently servo-controlled and articulating along at least one axis.

30. The method of claim 21, wherein each step in the method further comprises scanning said unique barcode label on said medication container and said syringe label to confirm that the syringe and medication container are handled according to said plurality of syringe prescriptions.

31. The method for semi-automated filling of syringes according to claim 21, wherein said step of adapting a selected container of medicine for insertion of a nozzle of a syringe comprises a step of replacing the manufacturer-supplied cap with a push-pull cap.

\* \* \* \* \*